United States Patent
Sexton et al.

(10) Patent No.: US 10,152,575 B2
(45) Date of Patent: Dec. 11, 2018

(54) ADHERENCE MEASUREMENT FOR CAREPATH PROTOCOL COMPLIANCE

(71) Applicant: Ayasdi, Inc., Menlo Park, CA (US)

(72) Inventors: Harlan Sexton, Palo Alto, CA (US); Tzu-Wei Powers, Mountain View, CA (US); Cindy Xin Zhang, San Jose, CA (US); Diljit Singh, Dublin, CA (US); Andrea Trave, Alameda, CA (US); Rishabh Sonthalia, Mountain View, CA (US)

(73) Assignee: Ayasdi, Inc., Menlo Park, CA (US)

( * ) Notice: Subject to any disclaimer, the term of this patent is extended or adjusted under 35 U.S.C. 154(b) by 0 days.

(21) Appl. No.: 15/795,202

(22) Filed: Oct. 26, 2017

(65) Prior Publication Data

US 2018/0113994 A1    Apr. 26, 2018

Related U.S. Application Data

(60) Provisional application No. 62/413,391, filed on Oct. 26, 2016.

(51) Int. Cl.
*G16H 10/60* (2018.01)
*G06F 19/00* (2018.01)

(52) U.S. Cl.
CPC ......... *G06F 19/3456* (2013.01); *G16H 10/60* (2018.01)

(58) Field of Classification Search
CPC ................. G06F 19/3456; G16H 10/60
See application file for complete search history.

(56) References Cited

U.S. PATENT DOCUMENTS

2002/0188182 A1    12/2002   Haines
2010/0274182 A1*   10/2010   Lafferty ............ A61M 5/14546
                                                    604/67

(Continued)

OTHER PUBLICATIONS

Konrad, R. et al., "Monitoring Adherence to Evidence-Based Practices: A Method to Utilize HL7 Messages from Hospital Information Systems," Applied Clinical Informatics, vol. 4, No. 1, pp. 126-143, Mar. 20, 2013.

(Continued)

*Primary Examiner* — Neal Sereboff
(74) *Attorney, Agent, or Firm* — Sheppard, Mullin, Richter & Hampton LLP

(57) ABSTRACT

An example method comprises receiving a protocol associated with a particular medical condition, selecting a subset of the events of the protocol to be adherence objects of an adherence path, determine a time frame predicate for each adherence object, determine an object predicate for each adherence object, retrieving patient information from medical records of patients of the medical entity, determining for each adherence object if each particular adherence object was performed as a part of that patient's treatment related to the medical condition including determining if the time frame predicate and object predicate are satisfied, and generating patient adherence object score for each adherence object of the adherence path, generating a medical entity adherence score based on the patient adherence object scores, the medical entity adherence score indicating that medical entity's compliance with the adherence path, and generating a report indicating the medical entity adherence score.

21 Claims, 49 Drawing Sheets

(56) References Cited

U.S. PATENT DOCUMENTS

2010/0293496 A1* 11/2010 Lafferty ............ A61M 5/14546
                                                      715/772
2014/0303092 A1* 10/2014 Painter ................. A61K 31/675
                                                      514/20.5
2015/0088628 A1    3/2015 Alhimiri
2016/0026706 A1    1/2016 Lum

OTHER PUBLICATIONS

International Application No. PCT/US2017/058618, International Search Report and Written Opinion dated Jan. 12, 2018.

* cited by examiner

|  | LAB | XR | ... | PAIN |
|---|---|---|---|---|
| LAB123 | 0.213 | 0.00012 | ... | 0.5 |
| ... | ... | ... | ... | ... |
| GENERIC LAB | 0.647 | 0.12 | ... | 0.01 |
| XR1107 | 0.476 | 0.066 | ... | 0.0003 |
| ... | ... | ... | ... | ... |

G1: LAB123, LAB665, LAB012, GENERIC XR

G2: LAB123, LAB665, LAB013, XR1107

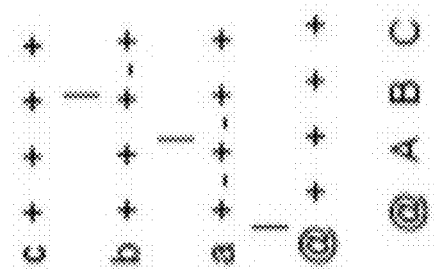
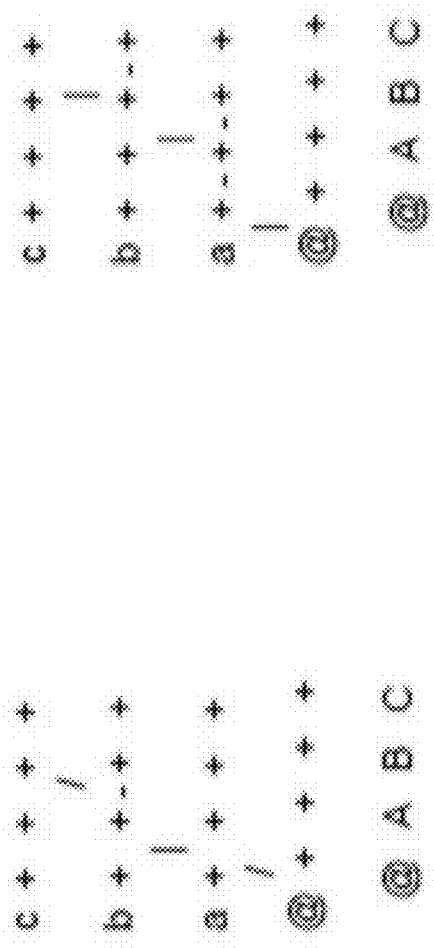
FIG. 7a
FIG. 7b

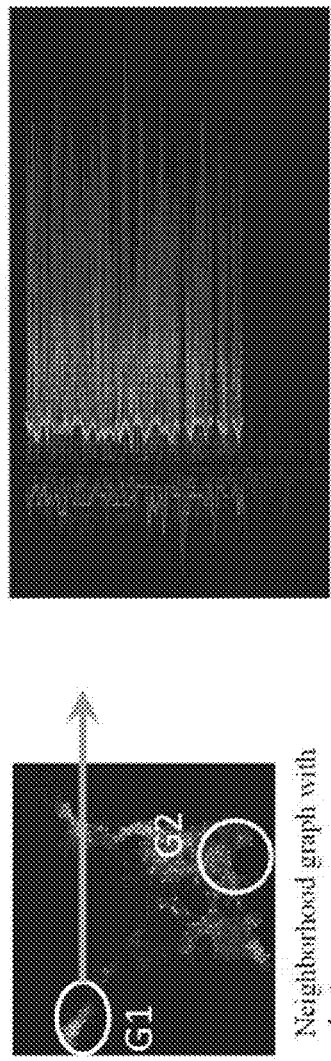
FIG. 8a — Neighborhood graph with clusters
FIG. 8b — Aligned event sets in cluster core
FIG. 8c — Consensus episode for cluster core
| Median Time | Action |
|---|---|
| 5 mins | LAB123 |
| 5 mins | LAB665 |
| 5 mins | XR1107 |
| 7 mins | NUR104 |
| ... | ... |

| Time (minutes) relative to surgery | Parent Category | Category | Code | Interval | Description |
|---|---|---|---|---|---|
| -27114 | Orders | EKG | EKG1 | unknown | EKG 12-LEAD |
| -27114 | Labs | LAB | LAB1725 | unknown | CBC WITH DIFFERENTIAL |
| -27114 | Labs | LAB | LAB276 | unknown | TYPE AND SCREEN |
| -27114 | Labs | LAB | LAB2638 | unknown | URINALYSIS WITH REFLEX CULTURE |
| -27114 | Labs | LAB | LAB15 | unknown | BASIC METABOLIC PANEL |
| -27114 | Labs | LAB | LAB847 | unknown | URINALYSIS |
| -27114 | Labs | LAB | LAB3330 | unknown | MRSA ACTIVE SURVEILLANCE |
| -27114 | Labs | LAB | LAB20 | unknown | PROTIME-INR |
| -27114 | Labs | LAB | LAB835 | unknown | FT3 |
| -149 | Orders | DIET | DIET40 | unknown | DIET NPO |
| -149 | Orders | IVF | IVF3 | unknown | INSERT PERIPHERAL IV |
| -149 | Orders | NUR | NUR542 | unknown | VERIFY INFORMED CONSENT |
| -149 | Orders | COD | COD3 | unknown | FULL CODE |
| -149 | Orders | NUR | NUR2007 | unknown | VITAL SIGNS PER PROTOCOL |
| -149 | Orders | NUR | NUR455 | unknown | NURSING COMMUNICATION |
| -149 | Orders | NUR | NUR5016 | unknown | PREP SURGICAL SITE |
| -149 | Orders | ADT | ADT1 | unknown | ADMIT TO INPATIENT |
| -149 | Orders | LAB | LAB2776 | unknown | BLOOD BANK DRAW ONLY |
| -111 | Meds | ELECT/CAL/OSM/H2O | LACTATED RINGERS IV | unknown | LACTATED RINGERS IV |
| -111 | Meds | ANTIARTHRITICS | CELECOXIB 200 MG CAPSULE | unknown | CELECOXIB 200 MG CAPSULE |
| -111 | Meds | ANALGESIC | OXYCODONE ER 10 MG CAP | unknown | OXYCODONE CR (OXYCONTIN) tablet 10 mg |
| -111 | Meds | CNS DRUGS | PREGABALIN 75 MG CAP | unknown | PREGABALIN 75 MG CAPSULE |
| -111 | Meds | ELECT/CAL/OSM/H2O | LACTATED RINGERS IV | unknown | LACTATED RINGERS IV |
| -111 | Meds | ANESTHETICS | MIDAZOLAM 1 MG/ML | unknown | MIDAZOLAM 1 MG/ML INJECTION |
| -60 | Orders | ADT | ADT7 | unknown | TRANSFER PATIENT |
| -42 | Labs | LAB | LAB2638 | unknown | URINALYSIS WITH REFLEX CULTURE |
| -41 | Meds | ANTIBIOTICS | CEFAZOLIN 2000 MG INF | unknown | CEFAZOLIN 2000 MG INFUSION 50 |
| -34 | Labs | LAB | LAB39 | unknown | URINE CULTURE |
| -14 | Labs | LAB | LAB847 | unknown | URINALYSIS |
| 82 | Orders | NUR | NUR2007 | unknown | VITAL SIGNS PER PROTOCOL |
| 32 | Orders | NUR | NUR502 | unknown | EDUCATION, SMOKING CESSATION AND SECO |

FIG. 9

FIG. 39

ADHERENCE MEASUREMENT FOR CAREPATH PROTOCOL COMPLIANCE

CROSS REFERENCE TO RELATED APPLICATION

This application seeks benefit of U.S. Provisional Patent Application Ser. No. 62/413,391, filed Oct. 26, 2016, entitled "Adherence Measurement and Variable Timing," which is hereby incorporated by reference herein.

TECHNICAL FIELD

The present disclosure generally relates to determining a consensus sequence from historical information and, more particularly, to techniques for copying content from applications when the applications are configured to different application states identifying consensus temporal patterns from past records of sequences of actions according to some quality metric(s) of interest.

BACKGROUND

As computers grow in both storage capacity and processing power, the collection of data has exploded. Unfortunately, as the amount and complexity of stored data grows, the ability to derive meaningful information from the stored data has been limited.

Data scientists have traditionally collected previously stored data and attempted to derive meaningful information through a query-based approach whereby a corpus of data is queried. Unfortunately, query-based approaches requires data scientists to guess at relationships in the stored data and then craft a meaningful query. Such an approach has limited value particularly as the amount and complexity of the data expands. Further, mistakes in formation of the query may lead to misleading results.

SUMMARY

An example method comprises receiving a protocol associated with a particular medical condition, the protocol comprising a set of events to occur in treatment of the medical condition, selecting a subset of the events of the protocol to be adherence objects of an adherence path, determine a time frame predicate for each adherence object of the adherence path, the time frame predicate indicating a time frame during which an event related to the adherence object is to be performed, determine an object predicate for each adherence object of the adherence path, the object predicate indicating one or more codes of an electronic health record system associated with an event related to the adherence object, the electronic health record system storing medical information related to a medical entity, receiving a medical condition identifier indicating a medical condition, treatment time frame identifier indicating a time frame during which treatment is to be performed, and a medical entity identifier identifying the medical entity, retrieving patient information from medical records of patients of the medical entity, the patients having received treatment related to the medical condition during the treatment time frame, the patient information indicating events related to treatment, for each patient, using that patient's patient information, determining for each adherence object of the adherence path if each particular adherence object was performed as a part of that patient's treatment related to the medical condition, the determining if each particular adherence object was performed including determining if the particular adherence object was performed during the time frame indicated in the time frame predicate and determining if at least one code from the patient's patient information is indicated in the object predicate, and generating patient adherence object score for each adherence object of the adherence path, the patient adherence object score indicating if the adherence object was performed, generating a medical entity adherence score for the medical entity based on the patient adherence object scores, the medical entity adherence score indicating that medical entity's compliance with the adherence path, and generating a report indicating the medical entity adherence score.

In some embodiments, the medical entity is a medical professional, group of medical professionals, facility, or system. The method may further comprise generating, for each patient, an patient adherence path score based on a number of adherence objects that were performed relative to that particular patient in comparison to all adherence objects of the adherence path, wherein the medical entity adherence score for the medical entity is based on an average of the adherence path scores. The medical entity may be a group of medical professionals and the method further comprises, for each medical professional of the group, generating, for each patient of that particular medical professional of the group, an patient adherence path score based on a number of adherence objects that were performed relative to that particular patient in comparison to all adherence objects of the adherence path, wherein the medical entity adherence score for the medical entity is based on an average of the adherence path scores.

In some embodiments, the medical entity is a group of medical professionals and the medical entity adherence score for the medical entity is based on the patient adherence object scores of patients of any of the group of medical professionals. The object predicate of a particular adherence object may indicate two or more codes that are equivalents, wherein the object predicate of the particular adherence object may be satisfied by events corresponding to any of the two or more codes. The object predicate of a particular adherence object may indicates two or more codes that must be completed to satisfy the object predicate, wherein the object predicate of the particular adherence object may be satisfied by all events corresponding to each of the two or more codes.

In some embodiments, the method may further comprise generating an interactive carepath interface enabling a user to view add adherence objects to the adherence path or change the object predicate or time frame predicate to at least one adherence object of the adherence path. In various embodiments, the method may further comprise, based on the patient adherence object scores, identifying a particular adherence object, and comparing outcomes of patients with treatments that did not comply with the particular adherence object with outcomes of patients with treatments that did comply with the particular adherence object. The method may further comprise removing the particular adherence object from the adherence path based on the comparison.

An example computer readable medium may comprise executable instructions that are executable by a processor to perform a method. The method may comprise receiving a protocol associated with a particular medical condition, the protocol comprising a set of events to occur in treatment of the medical condition, selecting a subset of the events of the protocol to be adherence objects of an adherence path, determine a time frame predicate for each adherence object of the adherence path, the time frame predicate indicating a time frame during which an event related to the adherence object is to be performed, determine an object predicate for each adherence object of the adherence path, the object predicate indicating one or more codes of an electronic health record system associated with an event related to the adherence object, the electronic health record system storing medical information related to a medical entity, receiving a medical condition identifier indicating a medical condition, treatment time frame identifier indicating a time frame during which treatment is to be performed, and a medical entity identifier identifying the medical entity, retrieving patient information from medical records of patients of the medical entity, the patients having received treatment related to the medical condition during the treatment time frame, the patient information indicating events related to treatment, for each patient, using that patient's patient information, determining for each adherence object of the adherence path if each particular adherence object was performed as a part of that patient's treatment related to the medical condition, the determining if each particular adherence object was performed including determining if the particular adherence object was performed during the time frame indicated in the time frame predicate and determining if at least one code from the patient's patient information is indicated in the object predicate, and generating patient adherence object score for each adherence object of the adherence path, the patient adherence object score indicating if the adherence object was performed, generating a medical entity adherence score for the medical entity based on the patient adherence object scores, the medical entity adherence score indicating that medical entity's compliance with the adherence path, and generating a report indicating the medical entity adherence score.

An example system may comprise one or more processors and memory. The memory may comprise instructions to configure the one or more processors to: receive a protocol associated with a particular medical condition, the protocol comprising a set of events to occur in treatment of the medical condition, select a subset of the events of the protocol to be adherence objects of an adherence path, determine a time frame predicate for each adherence object of the adherence path, the time frame predicate indicating a time frame during which an event related to the adherence object is to be performed, determine an object predicate for each adherence object of the adherence path, the object predicate indicating one or more codes of an electronic health record system associated with an event related to the adherence object, the electronic health record system storing medical information related to a medical entity, receive a medical condition identifier indicating a medical condition, treatment time frame identifier indicating a time frame during which treatment is to be performed, and a medical entity identifier identifying the medical entity, retrieve patient information from medical records of patients of the medical entity, the patients having received treatment related to the medical condition during the treatment time frame, the patient information indicating events related to treatment, for each patient, using that patient's patient information, determine for each adherence object of the adherence path if each particular adherence object was performed as a part of that patient's treatment related to the medical condition, the determining if each particular adherence object was performed including determining if the particular adherence object was performed during the time frame indicated in the time frame predicate and determining if at least one code from the patient's patient information is indicated in the object predicate, and generate a patient adherence object score for each adherence object of the adherence path, the patient adherence object score indicating if the adherence object was performed, generate a medical entity adherence score for the medical entity based on the patient adherence object scores, the medical entity adherence score indicating that medical entity's compliance with the adherence path, and generating a report indicating the medical entity adherence score.

An example method comprises receiving historical information of episodes, constructing event sets from the historical information, categorizing each event with general labels and synthetic labels, learning an event metric on the events by using the general and synthetic labels to perform dimensionality reduction to associate a vector with each event and to determine an angle between every two vectors, determining an event set metric using distances between each pair of event sets, deriving a sequence metric on the episodes, the sequence metric obtaining a preferred match between two episodes, deriving a subsequence metric on the episodes, the subsequence metric is a function of the event set metric on subsequences of each episode, grouping episodes into subgroups based on distances, for at least one subgroup, generating a consensus sequence by finding a preferred sequence of events, and the episodes of the subgroup, and generating a report indicating the consensus sequence.

Categorizing each event with general event category labels may comprise retrieving an ontology in the historical information and using the ontology to determine the general event category labels. In some embodiments, the preferred match between two episodes is an optimal match. The sequence metric may be a CP metric. The subsequence metric may be an ESCP metric.

In various embodiments, the function of the event set metric is a weighted sum. Each subsequence may be defined relative to one or more anchor points in the related episode. In some embodiments, each event includes a plurality of events. An order of the plurality of actions of at least one of the events is not distinguishable. Constructing event sets from the historical information may comprise constructing sets of events separated by no more than a predetermined period of time. The method may further comprise filtering the events to remove events that happen infrequently.

An example system may comprise an event set construction module, a categorization module, a categorization module, a metric construction module, a distance module, an episode metric assembly module, an autogroup module, and a consensus module. The event set construction module may be configured to receive historical information of episodes, each episode including at least one sequence of events taken over a period of time, and to construct event sets from the historical information, each of the event sets including at least one sequence of events. The categorization module may be configured to categorize each event from the historical information with general event category labels and synthetic event category labels. The metric construction module may be configured to learn an event metric on the events by using the general event category labels and synthetic event category labels to perform dimensionality reduction to associate a vector with each event and to determine an angle between every two vectors. The distance module may be configured to determine an event set metric using distances between each pair of event sets using the event metric. The episode metric assembly module may be configured to derive a sequence metric on the episodes to compute distances between episodes, the sequence metric obtaining a preferred match between two episodes with respect to a cost function describing a weighting for the event set metric, and to deriving a subsequence metric on the episodes to compute distances between episodes, the subsequence metric is a function of the event set metric on subsequences of each episode. The autogroup module may be configured to group episodes into subgroups based on distances obtained using the sequence metric and the subsequence metric. The consensus module configured to, for at least one subgroup, generate a consensus sequence by finding a preferred sequence of events with respect to a function of the sequence metric and the subsequence metric between the preferred sequence and the episodes of the subgroup and to generate a report indicating the consensus sequence.

An example computer readable medium may comprise executable instructions. The executable instructions being executable by a processor to perform a method. The method may comprise receiving historical information of episodes, constructing event sets from the historical information, categorizing each event with general labels and synthetic labels, learning an event metric on the events by using the general and synthetic labels to perform dimensionality reduction to associate a vector with each event and to determine an angle between every two vectors, determining an event set metric using distances between each pair of event sets, deriving a sequence metric on the episodes, the sequence metric obtaining a preferred match between two episodes, deriving a subsequence metric on the episodes, the subsequence metric is a function of the event set metric on subsequences of each episode, grouping episodes into subgroups based on distances, for at least one subgroup, generating a consensus sequence by finding a preferred sequence of events, and the episodes of the subgroup, and generating a report indicating the consensus sequence.

BRIEF DESCRIPTION OF THE DRAWINGS

FIGS. 7a and 7b are example illustrations of pairings and paths in a grid in some embodiments.

FIG. 8a is an example illustration of neighborhood graph with clusters in some embodiments.

FIG. 8b is an example illustration of aligned event sets in a cluster core in some embodiments.

FIG. 8c is an example illustration of a consensus episode for cluster core in some embodiments.

FIG. 9 is an example event set with one anchor point event showing numbered groups in some embodiments.

FIG. 39 depicts a physician operational dashboard for a total knee replacement in some embodiments.

Like reference symbols in the various drawings indicate like elements.

DETAILED DESCRIPTION

Example techniques to identify beneficial consensus temporal patterns from past records of sequences of actions is described herein. By selecting sets of past sequences of actions that were generally successful according to some quality metric(s) of interest, the consensus sequence produced may form a template for beneficial future actions.

In various embodiments, a sequence of actions taken over a finite period of time (an "episode") comprises sequences of sets of one or more "events." An event includes complex actions of some sort including, but not limited to, giving a patient medication, drilling an oil well, or issuing an order to buy stock. By establishing a measure of similarity between episodes, we can partition them into clusters and derive a consensus (e.g., an average) sequence of events for each cluster, which will form a consensus sequence.

Various embodiments include construction of an appropriate sequences of event sets, one or more metric(s) on events, one or more metric(s) on event sets, and one or more metric(s) on episodes. A procedure may subsequently be formulated for deriving consensus sequences from clusters of episodes. Example systems and methods are also described herein for predicting an outcome of episodes that were previously not observed.

Although systems and methods described herein demonstrate an application in health care (e.g., constructing carepaths that are sequences of interactions between care providers and patients) and a reduction to practice in the same domain, it will be appreciated that the same and/or similar techniques may be applied to any number of fields (e.g., oil and gas, finance, biotechnology, and/or the like).

Figure 1:
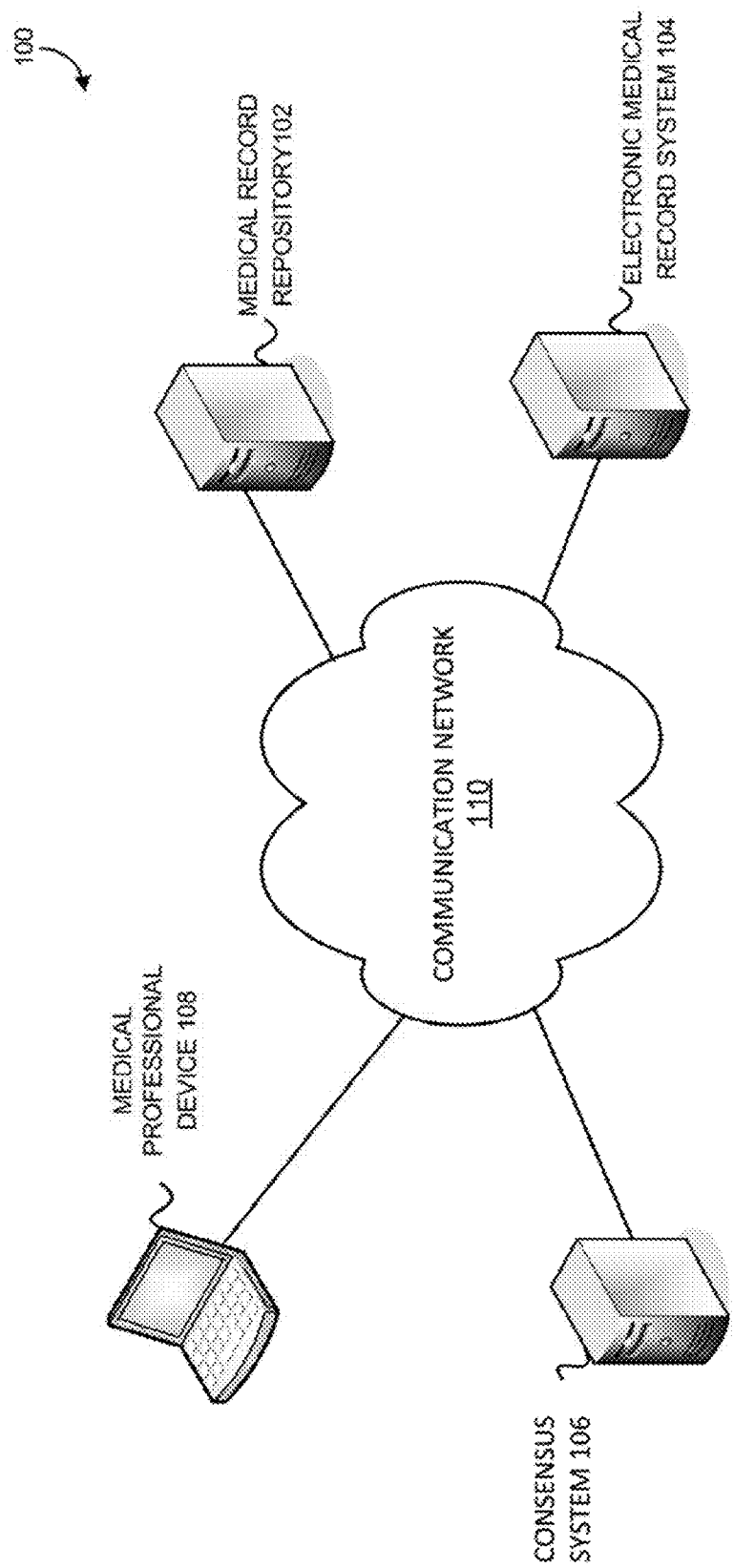
FIG. 1 is an example environment in which embodiments may be practiced.

FIG. 1 is an example environment 100 in which embodiments may be practiced. In various embodiments, data analysis for consensus sequence generation and/or outcome prediction may be performed locally (e.g., with software and/or hardware on a local digital device), across a network (e.g., via cloud computing), or a combination of both. There are many advantages between performing all or some activities locally and many advantages of performing all or some activities over a network. Although FIG. 1 is described regarding medical systems and devices, as discussed herein, it will be appreciated that there embodiments described herein may be used in any number of fields.

Environment 100 comprises a medical record repository 102, electronic medical record system 104, a consensus system 106, and a medical professional device 108 in communication over a communication network 110. Environment 100 depicts an embodiment wherein functions are performed across the communication network 110. In this example, a physician or patient may take advantage of cloud computing by storing data in a data storage server over a communication network 110. The consensus system 106 may perform analysis and generation of an consensus sequence report and/or prediction based on consensus sequences.

The medical record repository 102, electronic medical record system 104, consensus system 106, and medical professional device 108 may be or include any number of digital devices. A digital device is any device that comprises memory and a processor. Digital devices are further described in FIG. 18. A system may be any number of digital devices.

In various embodiments, the medical record repository 102 may include any amount of historical information (e.g., historical patient data). The medical record repository 102 may include, for example, an Electronic Medical Record (EMR) database. In one example, the medical record repository 102 may collect information from any number of medical professionals and related professionals (e.g., information from insurance companies) regarding any number of patients. For example, the medical record repository 102 may include medical records indicating treatment, labs, testing, operations, medicines, and/or the like related to any number of patients.

In various embodiments, the medical record repository 102 may include any amount of information regarding patients at multiple medical facilities and/or associated with any number of medical personnel. In some embodiments, the historical data of the medical record repository 102 may include historical information regarding any number of patients.

The electronic medical record system 104 may include any number of patient records (e.g., patient data) for any number of patients. In one example, the electronic medical record system 104 may receive and provide medical information regarding any number of patients for any number of physicians. In one example, the electronic medical record system 104 may include local patient information (e.g., patient information for any number of patients of a hospital or the like) and/or current information (e.g., labs to be performed and/or the like).

The medical professional device 108 is any device associated with a medical professional. In various embodiments, a physician may utilize the medical professional device 108. In various embodiments, the medical professional device 108 may provide patient information to the medical record repository 102 and/or the electronic medical record system 104. The medical professional device 108 may receive consensus sequence report (e.g., carepaths) based on patient historical data and/or provide predictions based on the consensus sequences discovered and current patient information. The medical professional and/or the medical professional device 108 may assess the consensus sequence report in view of a patient to determine a preferred course of action.

The communication network 110 may be any network that allows digital devices to communicate. The communication network 110 may be the Internet and/or include LAN and WANs. The communication network 110 may support wireless and/or wired communication.

The consensus system 106 is a digital device that may be configured to analyze data (e.g., historical patient information from the electronic medical record system 104) to generate the consensus sequence report (e.g., a report indicating a consensus temporal patterns from past records of sequences of actions performed).

The consensus system 106 may also receive patient information from the medical professional device 108 and provide a course of action or assessment based on the received patient information and the consensus sequences discovered. An example consensus system 106 is described with regard to FIG. 2.

Figure 2:
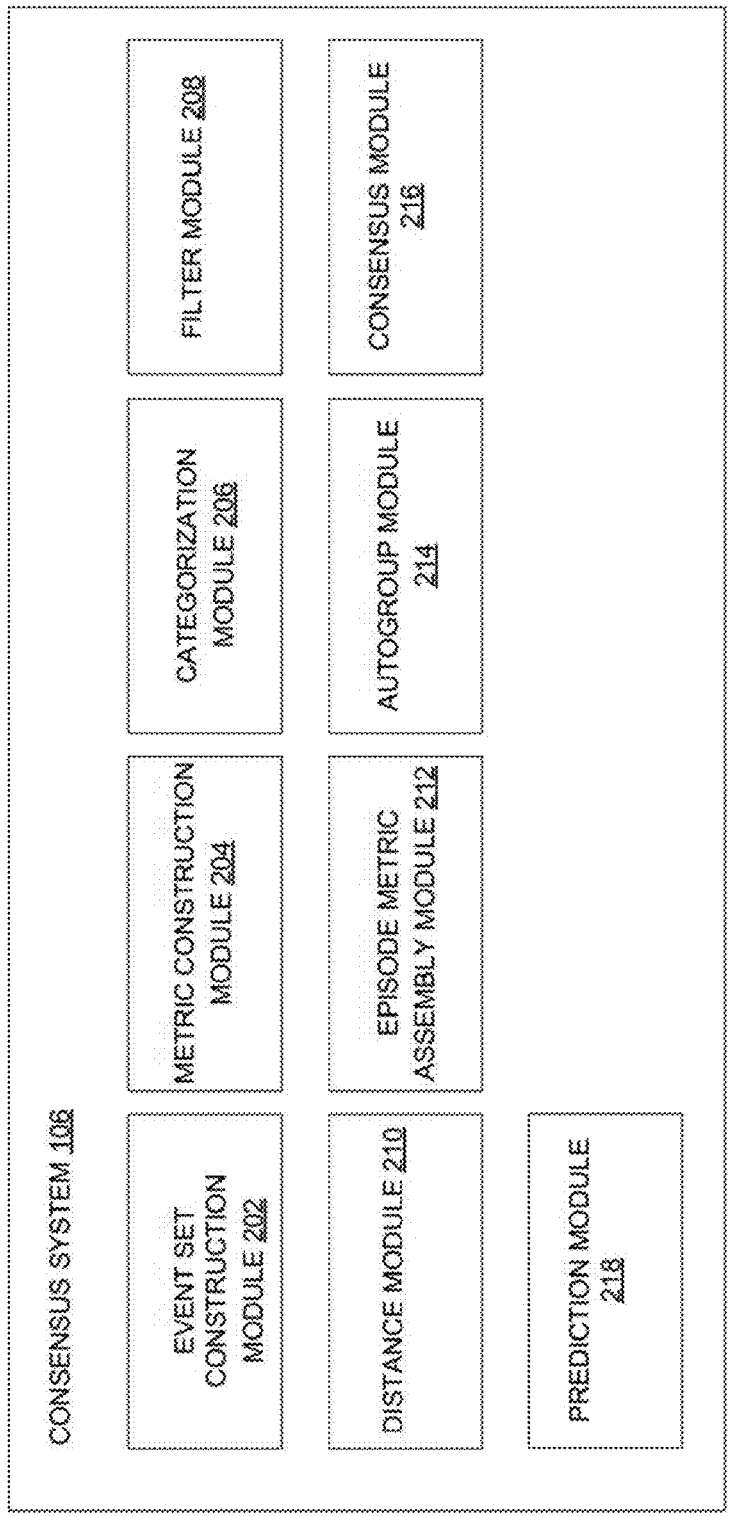
FIG. 2 is a block diagram of an example consensus system in some embodiments.

FIG. 2 is a block diagram of an example consensus system 106 in some embodiments. The consensus system 106 may comprise an event set construction module 202, a metric construction module 204, a categorization module 206, a filter module 208, a distance module 210, an episode metric assembly module 212, an autogroup module 214, a consensus module 216, and a prediction module 218. Each module is described herein with a more detailed example discussed with regard to the flowchart of FIG. 3.

In various embodiments, the event set construction module 202 is configured to construct event sets and episodes from events. Events in an event set are actions (e.g., interactions) whose order may be indistinguishable (e.g., a collection of tests ordered by a doctor at one time). An episode is then a sequence of these event sets.

For example, the event set construction module 202 may receive data from any number of sources, such as, for example, a medical record repository 102 and/or an electronic medical record system 104. The data may, for example, include medical information regarding any number of patients. The data may include, in some embodiments, a patient identifier and any amount of information for that patient including for example, medical tests, when medical tests were assigned, medical procedures (e.g., X-rays, surgeries, or the like, application of medicines), when the medical procedures were assigned and/or performed, outcome assessment, prognosis, symptomology, and/or the like.

Data may come from any number of databases. A database may be any data structure containing data (e.g., a very large dataset of multidimensional data). In some embodiments, the database may be a relational database. In some examples, the relational database may be used with MySQL, Oracle, Micosoft SQL Server, Aster nCluster, Teradata, and/or Vertica. Those skilled in the art will appreciate that the database may not be a relational database.

In some embodiments, a user identifies a data structure and then identifies ID and data fields. Data S may be based on the information within the ID and data fields. Those skilled in the art will appreciate that data S may be a finite metric space, or a generalization thereof, such as a graph or weighted graph. In some embodiments, data S may be specified by a formula, an algorithm, or by a distance matrix which specifies explicitly every pairwise distance.

In various embodiments, a metric is constructed on episodes which allows a quantitative attribution of a degree of difference (or equivalently, similarity) between at least two episodes by (e.g., optimally) pairing event sets, and then using a metric on a plurality (e.g., a pair) event sets. In some embodiments, a carepath metric (CP) (e.g., a sequence metric) uses both of these steps, and an event set carepath metric (ESCP) (e.g., a subsequence metric) utilizes only the latter step. The construction of both these metrics is will be described at length below.

In what follows, we show how to construct appropriate sequences of event sets, a metric on events, a metric on event sets, and finally a metric on episodes. We then formulate a procedure for deriving consensus sequences from clusters of episodes. We also describe a method for predicting the outcome of episodes that were previously not observed.

Finally, we demonstrate an application in health care (constructing carepaths, i.e. sequences of interactions between care providers and patients) and a reduction to practice in the same domain.

The metric construction module 204 is configured to learn a metric on the events from the data. In some embodiments, the metric construction module 204 constructs available episodes (e.g., sequences of event sets) from the received data as described herein. The metric construction module 204 may utilize the categorization module 206. The categorization module 206 may categorize events in the received data. In some embodiments, the categorization module 206 may receive tags or other categories from another source. For example, all or some of the events identified by the received data may be assigned categories (e.g., the all or some of the events in the received data may be associated with metadata that may be used to categorize the events). In one example, the categorization module 206 may receive an ontology that may be used to categorize events. In one example, various events performed in a hospital may be assigned a category (e.g., LABS). The received data may include, for example, descriptions of events and categories.

In various embodiments, the categorization module 206 may generate or receive categories (e.g., "general categories") of events. The categorization module 206 may, for example, generate categories based on metadata or other information associated with the received data. For example, the categorization module 206 may generate categories of events from the received data by using some of the data associated with the events to generate categories (e.g., based on natural language processing, semantic analysis, times of events relative to other events, available metadata describing the event, type of patient involved in the event, type of doctor or medical professional involved in the event, and/or the like).

The categorization module 206 may generate synthetic categories for events as well as general categories of events. A synthetic category may be, for example, a more generic or broader category that the general category (e.g., the synthetic category may be broader or more abstract than the categories provided as a part of the ontology). It will be appreciated that an event may be assigned two or more categories (e.g., a general and a synthetic category).

The filter module 208 may optionally filter (e.g., prune) events that occur too infrequently to be discriminated. In some embodiments, the filter module 208 utilizes one or more aggregation function(s) to identify and/or filter events (e.g., eliminate infrequent events). For example, the filter module 208 may aggregate frequencies of events across multiple patients to determine relative frequency for any number of events. Utilizing the aggregation, the filter module 208 may generate a frequency threshold (e.g., lowest 5%) to filter out events that fall below the generated frequency threshold.

In various embodiments, the filter module 208 identifies events that are to be filtered (e.g., removed) by utilizing the frequency threshold and subsequently replaces the events to be filtered with an instance of a synthetic category associated with the general category. In some embodiments, the filter module 208 replaces events to be filtered with an instance of a synthetic event (e.g., another event associated with the synthetic category). It will be appreciated that replacing events to be filtered with synthetic events or maintaining the event and changing the assigned category (e.g., to the synthetic category) may reduce noise.

Returning to the metric construction module 204, the metric construction module 204 may learn a metric on events using the categorization(s). The following discusses metric learning at a high level. A more detailed description may be found in the discussion regarding flow chart 3.

In various embodiments, the metric construction module 204 utilizes dimensionality reduction to make a metric on the events. A "context" may be defined from the event set. The context may be the collection of categories present on the set which may be vectorized by assigning a dimension to each category and further normalize to a norm value (e.g., a Euclidean norm value equal to one).

For each event, the metric construction module 204 may sum the contexts of all the event sets to which the event belongs. As a result, each event may be associated with a unit vector and the angle between such vectors may be used as the basis for a metric on the events.

The distance module 210 may compute a distance between event sets (e.g., using a greedy algorithm on the pairs of elements of each group). For example, the distance module 210 may determine the distances from all pairs of the two sets, removing exact matches.

The episode metric assembly module 212 may be configured to generate two metrics on episodes including, for example, a CarePath (CP) metric and an Event Set Care Path (EPSC) metric. Both rely on event "anchoring," the idea behind which is that the events and event sets in a pair of episodes have some intrinsic relationship due to their relative episodes, not just due to the precise events themselves. For example, there may be a difference between events which occur before surgery and those which occur after, and making this explicit may be significant. There is some sense in which this might be called an optimization (in the divide-and-conquer sense) but the improvement is not just in speed: using anchoring may also greatly reduce noise.

With one anchor point event, groups may be numbered with decreasing negative numbers before surgery and increasing positive numbers after surgery. With multiple anchor points, event-groups before the earliest anchor point may be numbered with decreasing negative values, and after each anchor point multi-indices (one for the anchor index and one for the event-group ordinal). Rules may be established (including penalties) for pairings between different anchor groups—for example, for surgical treatments an example rule is no pairing between pre- and post-surgical groups.

FIG. 9 is an example event set with one anchor point event showing numbered groups in some embodiments. Time 902 depicts events being numbered with decreasing negative numbers before surgery and increasing positive numbers after surgery. The parent category 904 may be a synthetic category and the category 906 may be a general category provided in the received data. The code 908 may be codes associated with events while the interval 910 may be a duration of the event. The description 912 may provide additional information regarding the event.

In various embodiments, the episode metric assembly module 212 may construct the CP metric using a modified version of dynamic time warping (DTW). DTW is a well known algorithm for measuring similarity between two temporal sequences which may vary in time or speed. The episode metric assembly module 212 may use DTW to match event groups in a pair of episodes to define a distance.

In computing the ESCP metric, the episode metric assembly module 212 may match (e.g., unconditionally) events by anchor value. This matching may identify subset(s) with substantial overlap in events to aid in the construction of a consensus.

The autogroup module 214 may autogroup subgroups using the CP metric. In various embodiments, data points of a data set or nodes in a graph are automatically grouped (i.e., "auto-grouped"). The groupings may be approximations of a possible maxima (e.g., a best maxima) of a given scoring function (e.g., the CP metric) that scores possible partitions of the original object (i.e., a collection of data points or a collection of nodes of a graph).

Auto-grouping may be utilized to automatically find a collection of subsets of some set Y that share one or more given properties. In one example, auto-grouping may be utilized to find a collection of subsets that is a partition of Y where Y is a subset of a finite metric space X or nodes in a graph. However, it will be appreciated, based on the disclosure, that the methodology described herein has no such requirement.

In various embodiments, a selection of possible partitions of a data set (e.g., original data set or nodes in a visualization) may be identified and scored. A partition is a collection of disjoint subsets of a given set. The union of the subsets of each partition equal the entire original set. A hierarchical clustering method may be utilized on the original object Y to create a family of partitions of Y.

Auto-grouping is the process in which this highest scoring partition is identified. The highest scoring partition may be the maximum of the given scoring function(s). In some embodiments, a limited number of partitions of possible partitions may be generated. In fact, in some cases, the result may be better if the scorer is imperfect, as at least some hierarchical clustering algorithms generally avoid partitions with large numbers of miscellaneous singletons or other ugly sets which might actually be the global extreme for such a scoring function. It will be appreciated that the hierarchical clustering process may serve to condition data to only present "good alternatives," and so can improve the effectiveness of some scorers.

Since the number of partitions for a data set is high (e.g., $(N/\log(N))^N$), it may be impractical to generate every possible partition. Unfortunately, most local improvement methods can easily get stuck. Some techniques to generate a subset of partitions involve attempting to maximize a modularity score over graph partitions by making an initial partition and then making local changes (e.g., moving nodes from one partition to another). Modularity is the fraction of edges that fall within given groups minus the expected such fraction if edges were distributed at random. Unfortunately, the modularity measure Q score typically exhibits extreme degeneracies because it admits an exponential number of distinct high-scoring solutions and typically lacks a clear global maximum. Another approach to maximizing functions on partitions by local methods is to use probabilistic techniques such as simulated annealing. At least some embodiments described herein offer a deterministic alternative that is applicable to a wide range of scoring functions.

Subsets in one or more different partitions of those generated may be selected based, at least in part, on the CP metric values. A new partition including the selected subsets may be generated or, if all of the selected subsets are already part of a generated partition, then the preexisting partition may be selected.

An example of autogrouping using scoring functions is discussed regarding FIGS. 14-17. It will be appreciated that autogrouping may be performed using any scoring function such as, for example, CP metric values.

The consensus module 216 may be configured to find a core of the autogrouped subsets (e.g., from the selected partition of the autogroup module 214). For example, given a subset of episodes S, the consensus module 216 may compute the points x in S such that the sum(y in S) CP(x,y) is smallest: we refer to such points as those of "maximum centrality" in S under CP. Given this most central subset using CP (call this M), the consensus module 216 then finds the most central subset of M using ESCP, and it is this subset the consensus module 216 denotes as the core C of S.

In various embodiments, having computed the core, the consensus construction is an optimization problem: we are looking for a candidate sequence of event-sets c such that Q(c, S)=sum(y in C) CP(c,y) is minimized, subject to a "believability" constraint: the events in c cannot be unrealistic. Specifically, in one example, this means that the consensus module 216 may start with an actual episode, and then edits it conservatively, keeping edits such that Q(c,S) improves. The consensus module 216 may use any optimization techniques (one level backtracking with a greedy algorithm).

The prediction module 218 is configured to predict outcomes of novel episodes (i.e., proposed courses of action) using the distance measures described herein. Using a linear combination of one or more such distance matrices, and values of dependent outcome variables, the prediction module 218 may construct a predictor that can predict the values of dependent outcome variables given input of new entity states, episodes, or a combination of both.

Modules, engines, and data stores included in the consensus system 106 and elsewhere in the description, represent features. The modules and data stores described herein may be embodied by electronic hardware (e.g., an ASIC), software, firmware, or any combination thereof. Depiction of different features as separate modules and data stores does not necessarily imply whether the modules and data stores are embodied by common or separate electronic hardware or software components. In some implementations, the features associated with the one or more modules and data stores depicted herein may be realized by common electronic hardware and software components. In some implementations, the features associated with the one or more modules and data stores depicted herein may be realized by separate electronic hardware and software components.

The modules and data stores may be embodied by electronic hardware and software components including, but not limited to, one or more processing units, one or more memory components, one or more input/output (I/O) components, and interconnect components. Interconnect components may be configured to provide communication between the one or more processing units, the one or more memory components, and the one or more I/O components. For example, the interconnect components may include one or more buses that are configured to transfer data between electronic components. The interconnect components may also include control circuits (e.g., a memory controller and/or an I/O controller) that are configured to control communication between electronic components.

Figure 3:
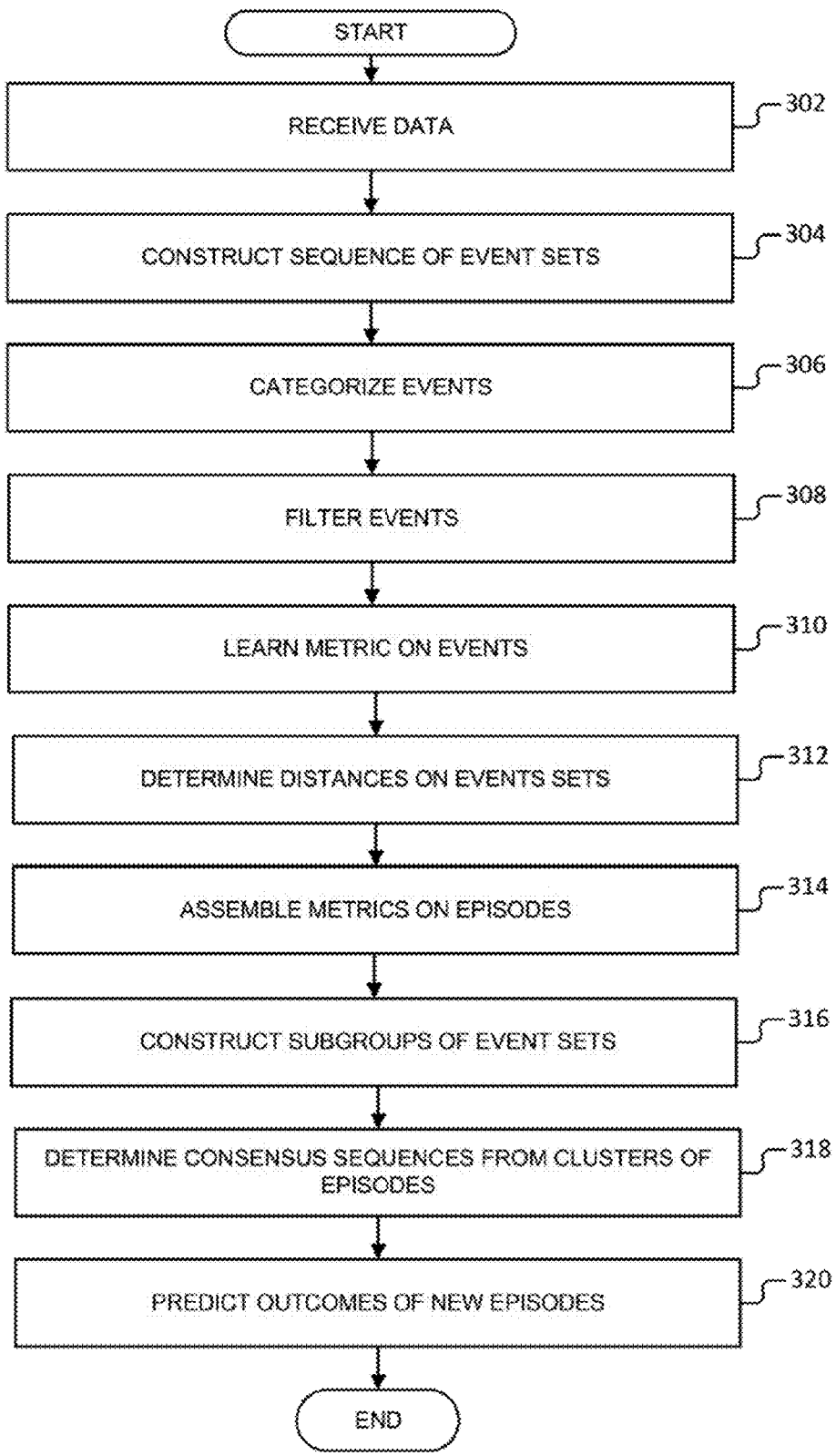
FIG. 3 is a flowchart of a method for generating consensus temporal patterns in some embodiments.

FIG. 3 is a flowchart of a method for generating consensus temporal patterns in some embodiments. In step 302, historical information is received. For example, the event set construction module 202 may receive historical information (e.g., historical medical information) regarding any number of patients.

In various embodiments, the event set construction module 202 is configured to construct event sets from the received data and episodes from events. The events in an event set are actions (e.g., interactions) whose order may be indistinguishable (e.g., a collection of tests ordered by a doctor at one time). An episode is then a sequence of these event sets.

In various embodiments, a metric is constructed on episodes to allow quantitative attribution of a degree of difference (or equivalently, similarity) between at least two episodes by (e.g., optimally) pairing their event sets, and then using a metric on pairs of event sets. In some embodiments, a carepath metric (CP) uses both of these steps, and a event set carepath metric (ESCP) utilizes only the latter step.

Figures 4, 5, 6:
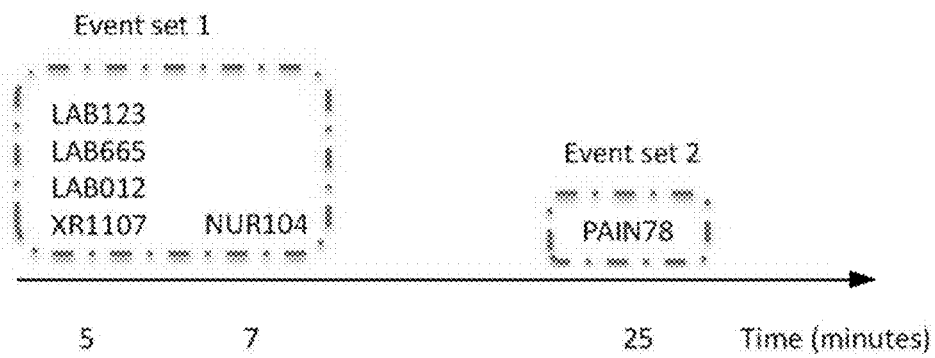
FIG. 4 is an example illustration of events in received data in some embodiments.
FIG. 5 is an example illustration of unit vectors in a Euclidean space of moderate dimensionality in some embodiments.
FIG. 6 is an example illustration of unmatched pairs are paired with generic events in some embodiments.

In step 304, the event set construction module 202 constructs sequences of event sets. To construct the event sets, the event set construction module 202 may utilize one or more heuristic(s) that specifies which events belong to a set. Here, sets may be constructed that are separated by small amounts of time (See FIG. 4). It will be appreciated that any amount of time may be used (e.g., ranging from 30 seconds up to 2 hours). In some testing, we found that the resulting metric on events was the least noisy at 5 minutes. Given that the time scales of actions for other problems are quite different, we are fairly certain this number would need to be revised for such occasions.

The metric construction module 204 may be configured to learn a metric on the events from the data. In some embodiments, the metric construction module 204 constructs all or some of the available episodes (e.g., sequences of event sets) from the received data. The metric construction module 204 may require categorization and/or filtering on the events.

In step 306, the categorization module 206 assigns events categories. For example, the categorization module 206 may assign events to higher-level groups (e.g., categories) by a supplied ontology. For example, various lab tests in a hospital may belong to the category LABS. These categories are utilized in the metric construction example described herein.

In some embodiments, the categorization module 206 creates a synthetic event category for any number of categories (e.g., for any number of categories provided by the supplied ontology). As discussed herein, a synthetic category may be, for example, a more generic or broader category that the general category (e.g., the synthetic category may be broader or more abstract than the categories provided as a part of the ontology). It will be appreciated that an event may be assigned two or more categories (e.g., a general and a synthetic category).

For example, the synthetic event category for LABS may be labeled "GENERIC LAB," and be understood to be a placeholder for some as yet unknown lab. Note that the category of a generic event may be defined to be a category for which that generic event was created.

In some embodiments, the metrics on the event-groups depend on having a metric on the events. If a metric on the event-groups is not given, the metric construction module 204 may construct a metric on the event-groups using the data. As discussed herein, events may be grouped in categories. The categories may be used to construct a metric on the events.

In step 308, the filter module 208 optionally filters events which occur too infrequently to be discriminated. In some embodiments, the filter module 208 utilizes one or more aggregation function(s) and to identify and/or filter (e.g., eliminate infrequent events). In one example, the filter module 208 generates a cumulative distribution using a cumulative distribution function for event frequencies and filter (e.g., "throw out") the 5% tail. In some embodiments, the filter module labels events 0 for the most common event, 1 for the next most common, and so on. The filter module 208 may then filter or (e.g., remove or eliminate) every event beginning with the number such that the total count of events from that number on is <=5% of the total number of events. In various embodiments, the filter module 208 utilizes a filter process that replaces the event with an instance of the synthetic event for that same category. It will be appreciated that this step may noticeably reduce noise in the resulting event metric space.

In step 310, the metric construction module 204 learns a metric on events using the categories and/or filtered events. In various embodiments, there may be an order of magnitude more types of events than categories (i.e., the dimensionality of the category space is much lower than that of the event space). We use this dimensionality reduction to make a metric on events. We define a "context" from an event set to be the collection of categories present in that set. For example, if a surgeon orders three lab tests and chest-x-ray at one time, this forms a set which looks like:

{ "COMPREHENSIVE METABOLIC PANEL,"
"CBC WITH DIFFERENTIAL,"
"LIPASE, "
"XR CHEST PA AND LATERAL"}

What this does is generate a "context" {LAB, LAB, LAB, XRAY}. The metric construction module 204 may vectorize these contexts by assigning each category a "dimension" in a Euclidean Space. If we suppose that XRAY is given dimension 2 and LAB dimension 4, then the vectorized context above would look like {0, 0, 1, 0, 3, . . . } where all the other entries are 0. We further normalize these contexts so that they have Euclidean norm=1, which means the context becomes {0, 0, 1/sqrt(10), 0, 3/sqrt(10), . . . }.

Now for each event, the metric construction module 204 may take the sum of the contexts of all the event sets to which that event belongs, and for synthetic events the metric construction module 204 may sum all the contexts for any event which has the same category as the synthetic event. After vector normalization, this may give every event (including synthetics) a unit vector in a Euclidean space of moderate dimensionality, and the angle between such vectors is used as the basis for a metric on the events (See FIG. 5 for example).

It will be appreciated that there may be a large number of event sets which are singletons. This lack of "additional information" (i.e., no context) means that the metric may not resolve these actions effectively. In various embodiments, the operation may be changed to add a value (e.g., 0.01) times the context before and/or after the event-set containing an event (including synthetics), assuming such event-sets exist. This small change may have the desired result without perturbing the rest of the metric. And second, because synthetic events were by their very definition indefinite, distance between a generic event and any other event may be defined in terms of the "dispersion" for real events of that category.

The dispersion of a category may be defined in any number of ways. For example, dispersion of a category may be defined to be square-root of the average of the squares of the angle distance between the synthetic vectorization and all the vectorizations of real events. This gives a measure of how "smeared out" the vectorizations for events in a category are, and may be a reasonable measure of the distance between a synthetic and non-synthetic event. For a pair of synthetic events, the distance is the dispersion if they have the same category, else it is the sum of their individual dispersions plus the angle distance between their respective vectorizations. The dispersion for any real event may be defined to be 0.

As an optimization, since there are not a very large number of distinct events, the metric construction module 204 may pre-compute and cache the distance matrix for the event space.

If events are not equipped a priori with an ontology that produces a categorization on the events, the categorization may be inferred from the data using a simple iterative algorithm. For example, the categorization module 206 may produce the full N×N co-occurrence matrix for all events, and use standard clustering algorithms to define clusters in that space (producing M<N clusters). The metric construction module 204 may take those clusters to be the categories described above, and re-learn the event metric in M-dimensional space. The metric construction module 204 may cluster again in this space, producing M'<M clusters, and re-learn the event metric in M'-dimensional space. The metric construction module 204 may iterate until the procedure converges and take the final clustering as the correct categorization.

In step 312, the distance module 210 computes a distance between event sets G1 and G2. In one example, the distance module 210 computes a distance between event sets G1 and G2 by using a greedy algorithm on the pairs of elements from each group. For example, the distance module 210 may remove exact matches (adding their distances—which will be 0 unless some synthetic events are present), and then the distance module 210 may compute the distances for all (remaining) pairs in the two sets. The distance module 210 may remove pairs greedily (shortest distances first, if both events are still in their respective sets), and then any left-over unmatched pairs are paired with generic events (See FIG. 6). It will be appreciated that this may be a straightforward extension of the typical solution to the pairing problem in dynamic time warping (which may be utilized herein) where a single type of "no match" event exists. However, it will be appreciated that there are any number of other pairings (e.g., using the Hungarian algorithm) which the distance module 210 might apply.

When pairing events A and B two different event-groups, the distance module 210 may consider two cases: the event distance between A and B, and the sum of the distances between A the synthetic version of A and B and the synthetic version of B. The distance module 210 may take the smaller of these two values as the pairing distance for A and B. As part of this process the distance module 210 may sometimes save the explicit match between event groups. In one example, the distance module 210 may incorporate this code in the distance computation under the control of a Boolean flag.

To be more specific, in some embodiments, if we let eva stand for the array of event objects sorted by integer event codes for the "A group" and evb for the "B group" we can use a zipper algorithm to copy the arrays of events into temporary integer stacks sa and sb containing the indices into eva and evb respectively (excepting any exact matches). We increment the return value by the distance between these exact matches, which are zero unless the matching events are generic. If we are preserving the explicit match, we save the pairs which matched exactly at this point in a separate stack of event pairs.

We then store all pairs of unmatched events as float/int/int triples f/i/j as a packed 64-bit Java long integer: here the float is the minimum of the event distance between the events eva[sa(i)], evb[sb(j)] and the sum of the event distances between the events eva[sa(i)] and evb[sb(j)] and their generics. We can use regular 'long sorting' in Java to sort these triples as f is in IEEE 32-bit format and >=0.0f.

We iterate over the sorted triples removing any pair we encounter when both elements are still present (clearing the respective entries in sa/sb so we know they were removed), and incrementing the return value by f. When we have emptied one of sa/sb, we stop and process any remaining sb/sa entries, incrementing the return value by the distance between that entry and its generic. If we are saving the pairs for the exact match we also use the indices to extract the event pair from eva and evb. We then return the cumulative matching value.

In step 314, the episode metric assembly module 212 assembles metrics on episodes. As discussed herein, we introduced two metrics on episodes: the Care Path (CP) metric and the ESCP (Event Set Care Path) metric.

In some embodiments, to construct the CP metric, the episode metric assembly module 212 may use a modified version of dynamic time warping (DTW, also known as sequence alignment) to match event-groups in a pair of episodes to define a distance. Here, an event set is a sequence of events (possibly including synthetic events) and a "synthetic" set is an event set composed entirely of synthetic events. If A is an event set, we define synth(A) to be the set formed by replacing every code in A by its generic form: for A={NUR1, CT5, GENERIC_XR}, then synth(A) is {GENERIC_NUR, GENERIC_CT, GENERIC_XR}

Suppose we have a metric $d(A,b) \geq 0$ defined on pairs of event sets which also has the property that d(A,*), for * synthetic, is minimized by d(A,synth(A)). Then we can define a metric on pairs of sequences of events even if the sequences are of different lengths. Given two sequences of sets AB ... and ab ... of the same length, we can define a "base metric" bd(AB ..., ab ...) as d(A,a)+d(B,b)+ ... We then extend this to two sequences of possibly different lengths ABC ... and abc ... by "editing" the sequences with insertions of "synthetic sets" to get pairs of sequences of the same length, and then taking the minimum value. If we denote any synthetic set by *, then we can define a distance between AB and abc as the min {bd(AB*,abc), bd(A*B*, a*bc), ... }, over all possible equal length pairs of edits. This is well-defined because any possible pair of edits which have corresponding *'s can be edited to remove those matching synthetic sets (the value of sum of bd( )'s will not increase), and we know that every * can be replaced by the matching synth( ) event in the other sequence. From this we see that we are taking the minimum over a finite set of edits, and these edits can be thought of as pairs sequences of "pairings" of the form A<->x, Y<->*, or *<->z, which we call "diagonal," "horizontal," respectively "vertical" pairings, for reasons that will shortly become clear.

Let @ be a special code that is otherwise unused. There is a natural correspondence between such pairings and paths (going to the right and up) in the grid with nodes labeled by pairs (x,y) where x ranges over {@,A,B,C, ... } and y ranges over {@,a,b, ... }. Going, up diagonally corresponds to diagonal pairing, while a vertical edge is a vertical pairing and a horizontal edge is a horizontal pairing. As examples, the matching ABC with abc of A*BC<->ab*c is shown in FIG. 7a; matching ABC with abc by AB*C*<->a**b*c is show in FIG. 7b.

Intuitively a path has a "component in the direction of a sequence element being consumed." The paths must begin in the lower left and go up and/or to the right to the upper right corner. Additionally, since we are looking for consensus on episodes, we probably can count on not being interested in paths with "sufficiently many" synthetic sets, so if the sequences are too different in length or too far from the diagonal, we probably can return a "large value" and quit. This suggests matching at the set level might be linear in the number of sets—and at least less than quadratic—as interesting paths would be constrained to be around the diagonal. To find the cost of the optimal path we only need a matrix of the same size as the grid in which all the paths lie. We assign to every grid point the minimum path cost to get to that point.

We can only get to a point (C,b) from (B,a), (C,a), or (B,b)), and there is only one way from each of these points to (C,b), so knowing those 3 values means we can compute the fourth—a perfect situation for dynamic programming (Note, in fact, that we only need the values for the current column and the previous one, which cuts down on the intermediate state required although not on the number of computations). We will denote this minimal cost state by the table MinCost(,)—that is a properly initialized MinCost(M, n) will be cost of the best pairing of the elements A, ..., M with a, ..., n, where MinCost(@,b) means pair *,* with a,b, (i.e. bd((*,*),(a,b)), and and so forth. Naturally MinCost(@, @) is 0. Let us now denote the events A,B,C, ... by g[0],g[1], etc. and a,b,c, ... by the elements of the array h[]. Instead of MinCost( ) we will use a matrix DTW[i][j] defined to be MinCost(g[i-1],h[j-1])—that is, DTW[i][j] is the cost of the best path aligning the first i entries of g with the first j entries of h. (This reserves the index 0 for @.) DTW is M×N where M=g.length+1 and N=h.length+1, and the cost of the best path is DTW[g.length,h.length]. In pseudocode the matching is performed as per DIST( ) below, where synth(set) is the synthetic version of an event set and d(group,otherSet) is the non-negative symmetric distance between event sets:

```
DIST(g: sets [0..N-1], h: sets [0..M-1]) {
// DTW[x][y] is the cost of the minimal PATH which 'consumes' the first
// x elements of g and the first y elements of h - that is, the cost of
// the best path from (0,0) to (x,y) in the plane.
DTW := double[N+1][M+1]
// Fill in the values for the bottom row of the grid
for i := 0 to N-1
    DTW[i+1][0] := d(g[i],synth(g[i])) + DTW[i][0]) // horizontal
// Fill in the values for the left column of the grid
for j := 0 to M-1
    DTW[0][j] := d(synth(h[j]), h[j]) + DTW[0][j]) // vertical
for i := 0 to N-1
    for j := 0 to M-1
        DTW[i+1][j+1] :=
            min(d(g[i], h[j]) + DTW[i][j],          // diagonal
                d(g[i], synth(g[i])) + DTW[i][j+1], // horizontal
                d(synth(h[j]), h[j]) + DTW[i+1][j]) // vertical
return DTW[N, M]
}
DTW[0][j+1] = d(synth(h[j]), h[j]) + DTW[0][j] for all j>=0, because the
only possible path to (0,j) has the first j+1 entries matched with
synthetics. Similarly for DTW[i][0].
```

The event group distance may works as shown in pseudocode below. The idea is to penalize matchings of event sets whose indices are too far off from one another, so pairs of episodes may be rejected that are "too different."

```
public double eventSetDistance(Episode pA, EventSet a,
        Episode pB, EventSet b) {
    // Bail if the anchorCode's don't match - we can use this to avoid
    // splitting the anchor segments and doing DTW individually on them,
    // but the complexity of that is outweighed by the performance gain
    of
```

-continued

```
    // making the 'sides of the grid' smaller.
    if (a.anchorCode != b.anchorCode)
        return HUGE;
    // We take 2/3's of the 'average synthetic error' as the scale to make
    // the error 'slightly weaker' than the average synthetic
    // error.
    double sdError = (a.distanceToSynthetic +
    b.distanceToSynthetic)/3.0;
    double indexError = (a.zbIndex - b.zbIndex)/2.0;
    double incr = sdError * indexError * indexError;
    // The error is always included since even an exact match between
    // groups of widely different 'times' is still undesirable.
    return eventSetPairing(pA, a.events, pB, b.events, null) + incr;
}
```

The method eventSetPairing( ) does an unconditional matching of the pairs of events in the respective anchor sets from Episodes A and B and returns the resulting distance.

Finally, in computing the ESCP metric (used in the for the second step of consensus core computation below), the episode metric assembly module 212 may perform only the unconditional matching of events by anchor value (e.g., for surgical episodes we make positive and negative groups out of the events in each episodes and pair them and return the total error). In some embodiments, the set of episodes may have been reduced once to those which match up well as "time series" of event sets. This step tries to find a subset with substantial overlap in the actual events, to aid in the construction of a consensus.

The consensus module 216 may determine consensus sequences from clusters of episodes. Having learned the CP and ESCP metrics from the data, we now describe a clustering/portioning of episodes in the data source and a process for computing a consensus sequence from the partitions.

In step 316, subgroups of events sets are constructed. In various embodiments, the autogroup module 214 automatically constructs coherent subgroups using the carepath metric CP. In one example, the autogroup module 214 constructs a graph of the metric space using the 5 nearest neighbors for each point where the additive edge strength between points p and q is 1/(ordinalDistance(p,q)), where the ordinalDistance(p,q) is j if q is the jth nearest neighbor of p. Having constructed the graph, the autogroup module 214 autogroups using 95% as the "clustering cutoff" The autogroup module 214 then generates a partition of the nodes in the graph, and as those nodes are episodes, this partition gives rise to a collection of "related subsets" on which to search for a consensus (See FIGS. 8a-8b). It will be appreciated that any number of nearest neighbors may be utilized (e.g., not only five) and that the clustering cutoff may be any threshold (e.g., any percentage, discrete value, or the like).

As discussed herein, the process of autogrouping is described with regards to FIGS. 14-17.

Having reduced the problem to searching for a consensus carepath on a given subset, the consensus module 216 may find the "core" of the subset, and then the consensus module 216 processes the core to produce a consensus in step 318. Given a subset of episodes S, the consensus module 216 computes the points x in S such that the sum(y in S) CP(x,y) is smallest: we refer to such points as those of "maximum centrality" in S under CP. Given this most central subset using CP (call this M), the consensus module 216 then finds the most central subset of M using ESCP, and it is this subset the consensus module 216 denotes as the core C of S. We reject any input subset of length less than 40, since 20 is the minimum core size we have found usable, and we prefer sets with at least 100 points. To increase the probability that that these size constraints are satisfied, in the first step the consensus module 216 finds an M whose size is the minimum of 150 and (1/sqrt(2.0)) times the size of S. The size of C is taken to be the minimum of 100 and (1/sqrt(2.0)) times the size of M. These values would be adjusted for different data types (See FIG. 8b).

Having computed the core, the consensus construction may be an optimization problem: we are looking for a candidate sequence of event-sets c such that Q(c, S)=sum(y in C) CP(c,y) is minimized, subject to a "believability" constraint: the events in c cannot be unrealistic. Specifically, in one example, this means that the consensus module 216 may start with an actual episode, and then edits it conservatively, keeping edits such that Q(c,S) improves. The consensus module 216 may use standard optimization techniques (one level backtracking with a greedy algorithm) with two non-standard heuristics described below.

The first non-standard optimization step is when to begin the optimization without inferring the times of individual events by spreading out the times so everything in an event set has precisely the same time, and the event set are kept apart by a fixed delta. After adding or removing events, the consensus module 216 reruns this process. It is only at the end (e.g., once we feel comfortable with the constituent event-groups) that the consensus module 216 adjusts the event times in the consensus by taking the median time of matching events in the episodes in the core set (See FIG. 8c).

In some embodiments, the second non-standard optimization step is a rule in the editing process such that an event cannot be removed if its count would fall below some minimum number, which we take to be the floor of the average of the first and second quartiles for the counts of that event in the core set; this prevents common events from disappearing but does allow us to reduce the number when this improves CP centrality. We also try to add entire groups, but this rarely succeeds as the starting point for consensus tends not to be missing groups—instead groups are missing occasional individual events found in most other event-groups in the core.

In step 320, the prediction module 218 may predict outcomes of novel episodes (i.e., proposed courses of action) using the distance measures discussed herein, and optionally one or more additional distances representing the state of the entity of interest before the episode commences. Each such distance may give rise to a distance matrix between entities. Using a linear combination of one or more such distance matrices, and values of dependent outcome variables, the prediction module 218 constructs a predictor that can predict the values of dependent outcome variables given input of new entity states, episodes, or a combination of both. With such predictions, one may, for example, optimize the entity states, the episodes, or both, with respect to the outcome variable(s) of interest; forecast outcomes based on said inputs; or similar tasks.

Figure 10:
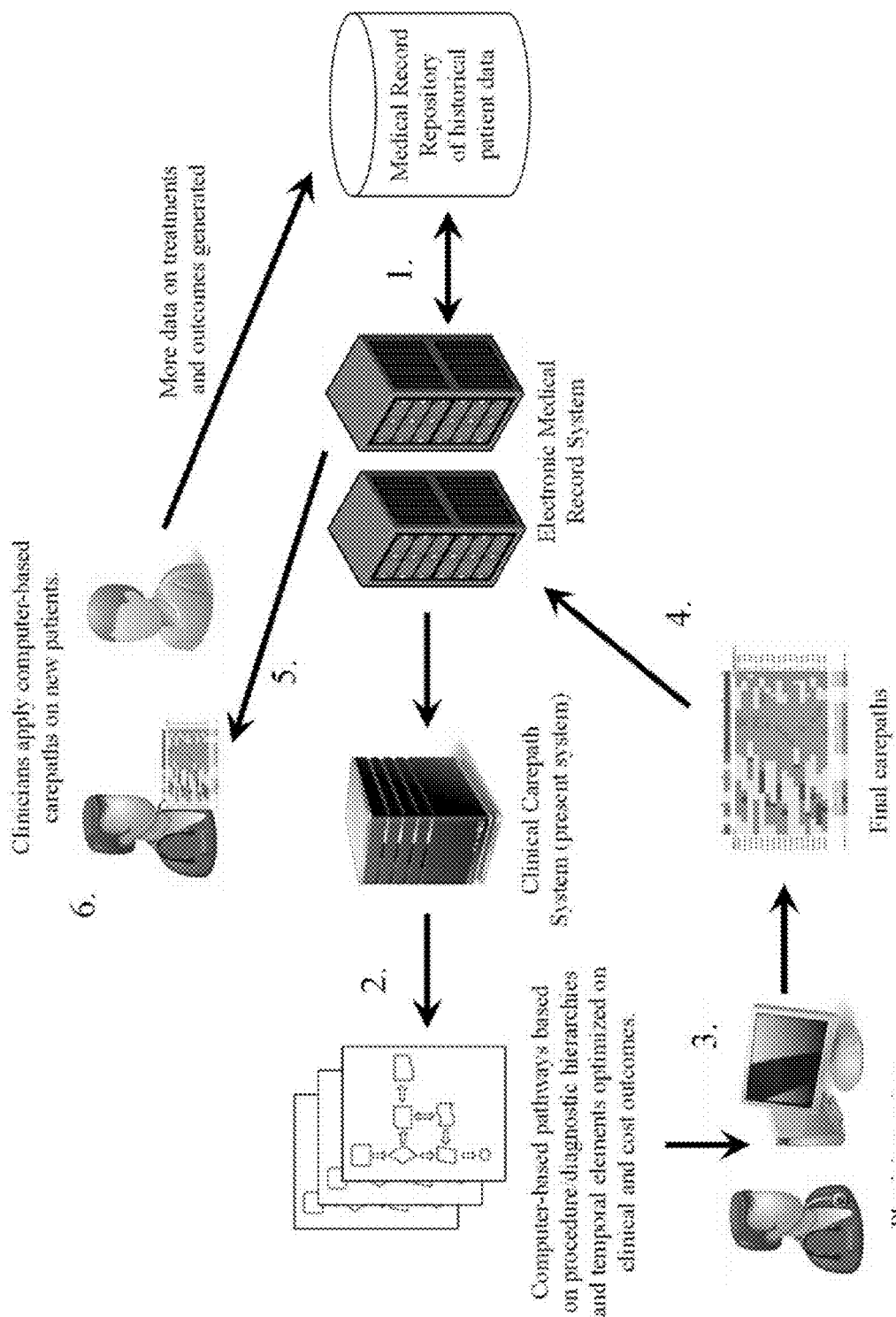
FIG. 10 is a flow diagram of a health care example in some embodiments.

FIG. 10 is a flow diagram of a health care example in some embodiments. In the health care example, a problem being solved is that of perioperative surgical care. In other words, a problem being solved is the determination of which treatment should be provided before and after surgery, inside the hospital, to maximize the chance of a good outcome. Events in this case are various interactions between care providers and patients: lab tests, doctor's orders, and medications administered. Events are considered relative to the time of surgery (the anchor point). In this example, the events are categorized by an ontology present in the data source itself (e.g., an Electronic Medical Record (EMR)

database). Event sets map loosely to the notion of order sets: the bundle of one or more actions ordered and/or administered that a care provider specifies during an interaction with the patient.

In this example, episodes are the sequences of such sets over some specified period pre- and post-operatively (e.g., 30 days before and after surgery). Example consensus episodes (in the medical case, "carepaths") are derived using the method(s) described herein, reviewed and modified by physician staff into final form (with support from predictive capabilities), and then built into the EMR system itself. When physicians interact with patients, the EMR system may recommend the carepath to the physician, who then treats the patient and records the treatments along with the outcome. The system then feeds back on itself and continuously improves the carepath over time.

See FIG. 10 for an overview. In step 1, Medical record data repository passes historical patient information to the electronic medical record (EMR) system, which shares this data with the Data-Driven Clinical Carepath System (DDCC) (e.g., the consensus system 106). In step 2, DDCC generates draft clinical carepaths based on clinical outcomes and cost reduction goals. These drafts may be made available to physicians. In step 3, physicians review the draft carepaths and generate the final versions. In step 4, final carepaths are uploaded to the EMR, allowing them to be activated automatically as patients enter the medical system. In step 5, the patient has a new medical encounter, and the clinical carepath is activated depending on diagnosis or procedure ordered.

In a further example, a sequences of event sets are constructed from historical information. As per above, events may be derived from the EMR database, and clustered into sets with a 5 minute timeout. In some embodiments, events are expected to be time stamped to within at least minute-level accuracy, and many events may share a time stamp.

At least one metric on the events may be subsequently learned. Thousands or tens of thousands of event types can be categorized into on the order of 100 high-level categories (e.g. X-rays, analgesics, nursing orders, etc.), from an ontology present in the EMR data. Given this categorization, the metric may be learned from treatments (e.g. all surgical episodes) present in the database, or a subset of that data over some specified time, surgical procedure, hospital, or similar. At least one metric may be derived on the event sets. Event sets may be treated as described above.

Subsequently, Metrics may be assembled on episodes. A modified DTW algorithm described above may be used. In this example, there is a single anchor point, which is the exact start time of the surgical procedure. In some embodiments, only perioperative events (i.e., events that happen outside the surgical ward) are taken into account. Events on opposite sides of the anchors may not be aligned (i.e., incur an enormous alignment cost). Only episodes from the same surgical procedure (e.g. total knee replacement) may be compared, as the goal is to produce a carepath tailored to a particular care interaction.

Consensus sequences (carepaths) may be derived from clusters of episodes. Before cluster construction, the episode population may, if desired, be filtered to provide a more targeted set of treatments. For example, one may wish to construct a carepath for only patients with hypertension, patients in a particular area, for a surgeon that is known to be particularly skilled, etc. After any such filtering and clustering, the clusters may be scored according to a scoring scheme provided by the user. For instance, one might consider large clusters to be better (they provide stronger statistical support). It may also be desirable to score the clusters on factors such as cost to the hospital, length of stay, satisfaction of the patient, or the risk of readmission. Any linear combination of such metadata variables may be used. The cluster with the highest score may be selected for consensus construction, and results may be reported back to the user in the form of a specially constructed interface for viewing, manipulating and exporting proposed carepaths (see FIG. 10). Note that the interface also shows the underlying episodes that constructed the carepath (including the starting point for the optimization step), and any metadata attached to such episodes (such as patient comorbidities, vital statistics, attending physician, etc.).

The method may also provide for a way of interactive predicting what changes in the proposed carepath would do in terms of the outcomes of interest. For each cluster core from which a carepath is generated, a predictor (e.g. a K Nearest Neighbor regressor or classifier) may be parameterized on some outcome of interest (e.g. a quality measure like length of stay in the hospital). The system allows a user (e.g. a physician) to interactively alter the proposed carepath, which triggers a prediction of what the novel carepath would do in terms of the outcome. In this manner, the user may inject domain knowledge into the otherwise automated process, and explore what different tweaks of the auto-generated starting points may improve the downstream results. The user may then save the edited carepath, and/or the computer-generated carepath, into the system and move forward in the implementation process.

Figure 11:
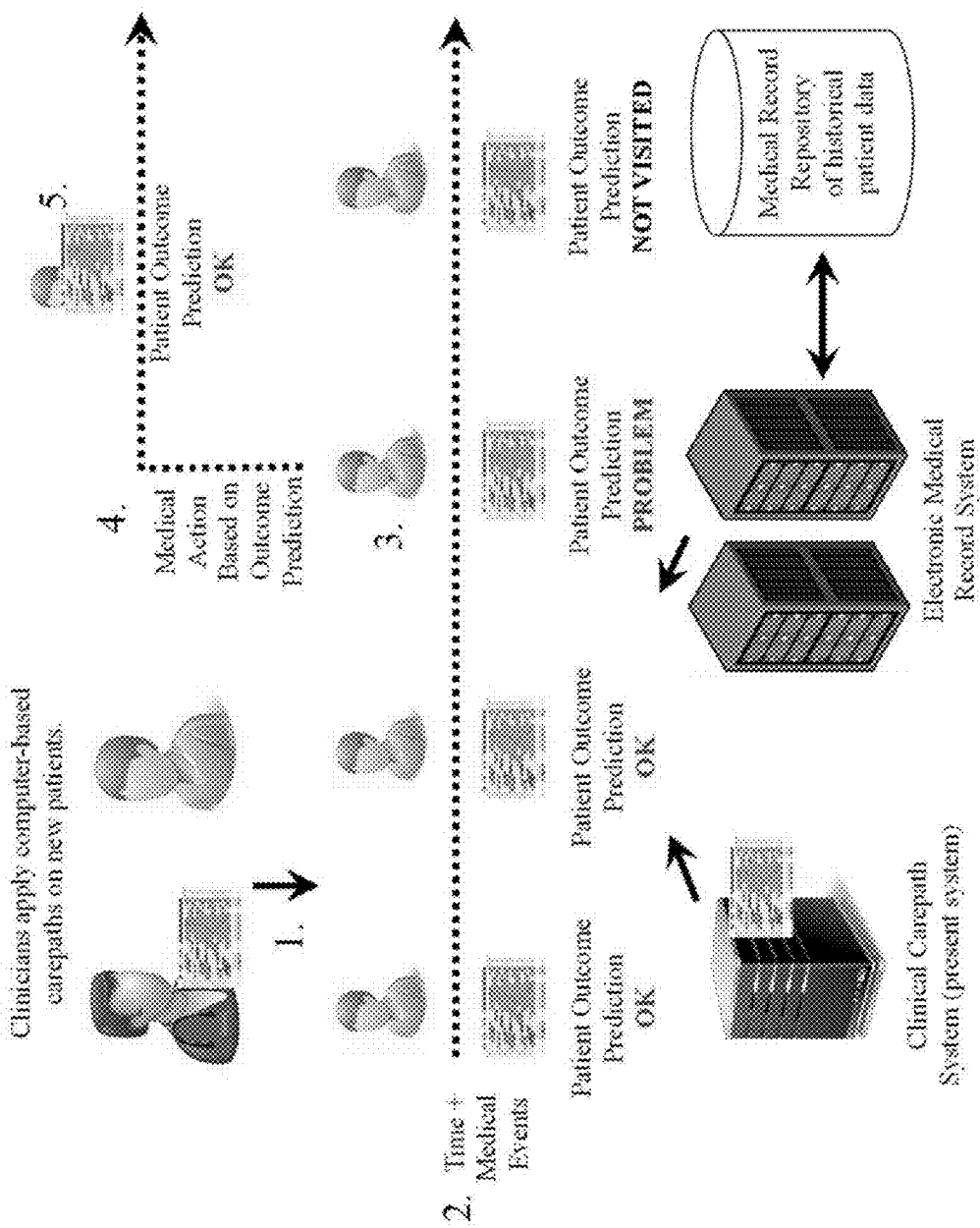
FIG. 11 is another example of the application of some embodiments to health care in some embodiments.

FIG. 11 is another example of the application of some embodiments to health care. In some embodiments, a patient has a new medical encounter, and the clinical carepath is activated depending on diagnosis or procedure ordered. The patient may experience a number of clinical encounters while under treatment. The carepath may be tracked digitally in the EMR to monitor the patient as they progress through the carepath, using predicted outcomes based on patient information from the clinical encounters as a flag for alerting.

Predictions from the digital carepath that suggest poor outcomes based on prior patient encounters are flagged, and the clinician may adjust the patient course of action to improve the predicted outcome. Medical action may be taken based on the change in carepath. Patient outcome prediction is returned to a stable track.

Figure 12:
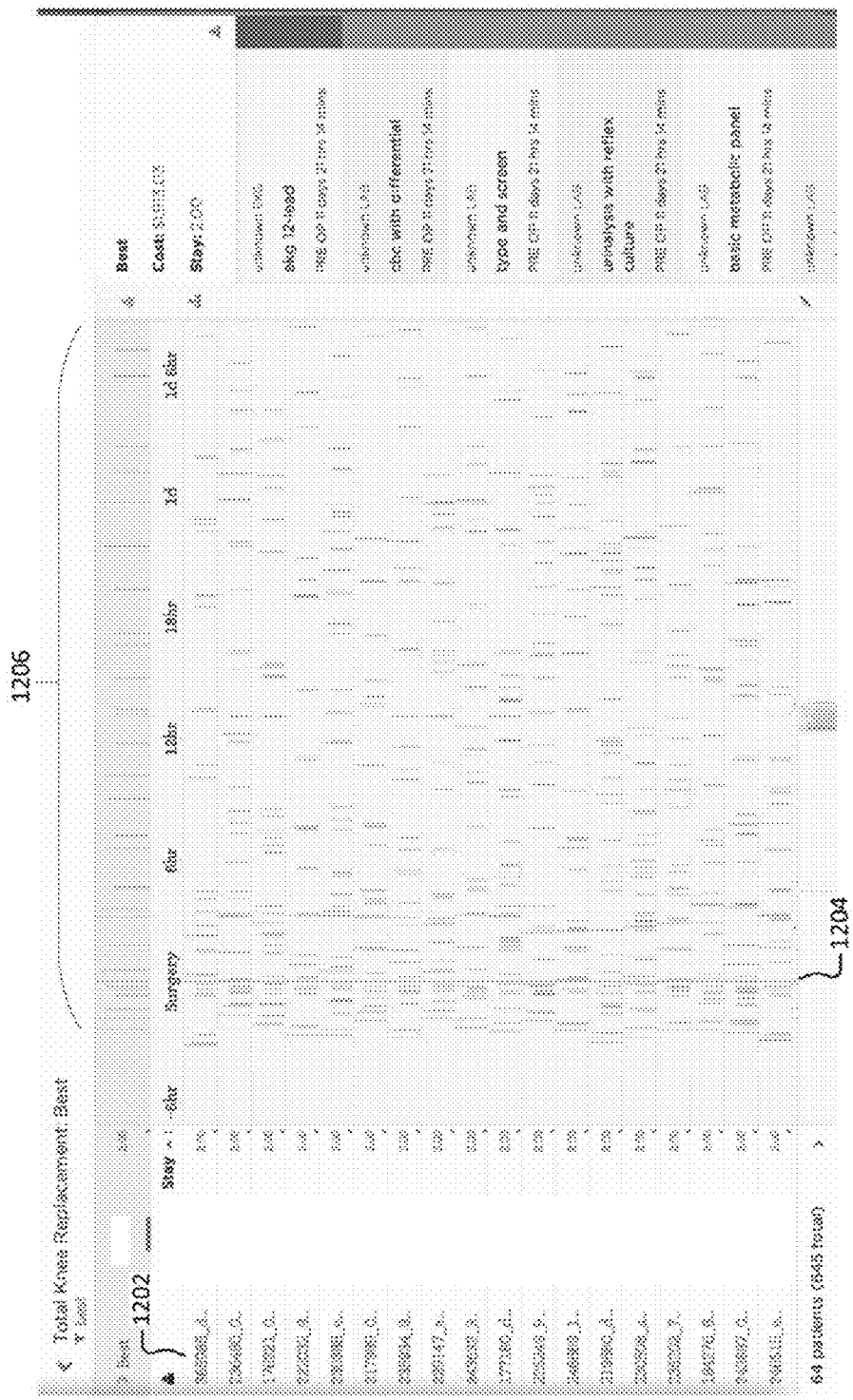
FIG. 12 is an example carepath consensus interface in some embodiments.

FIG. 12 is an example carepath consensus interface in some embodiments. In this example, each patient identifier 1202 (anonymized and fictitious for this example) is associated with a series of events indicated in event sequence 1204. The consensus sequence, in this example, is 1206 at the top of the example carepath consensus interface. The consensus sequence 1206 may indicate the best (e.g., optimal in terms of benefit and/or cost) in view of the historical data associated with each patient identifier 1202. In various embodiments, the example carepath consensus interface and/or the consensus sequence 1206 may be or included in the consensus report.

Figure 13:
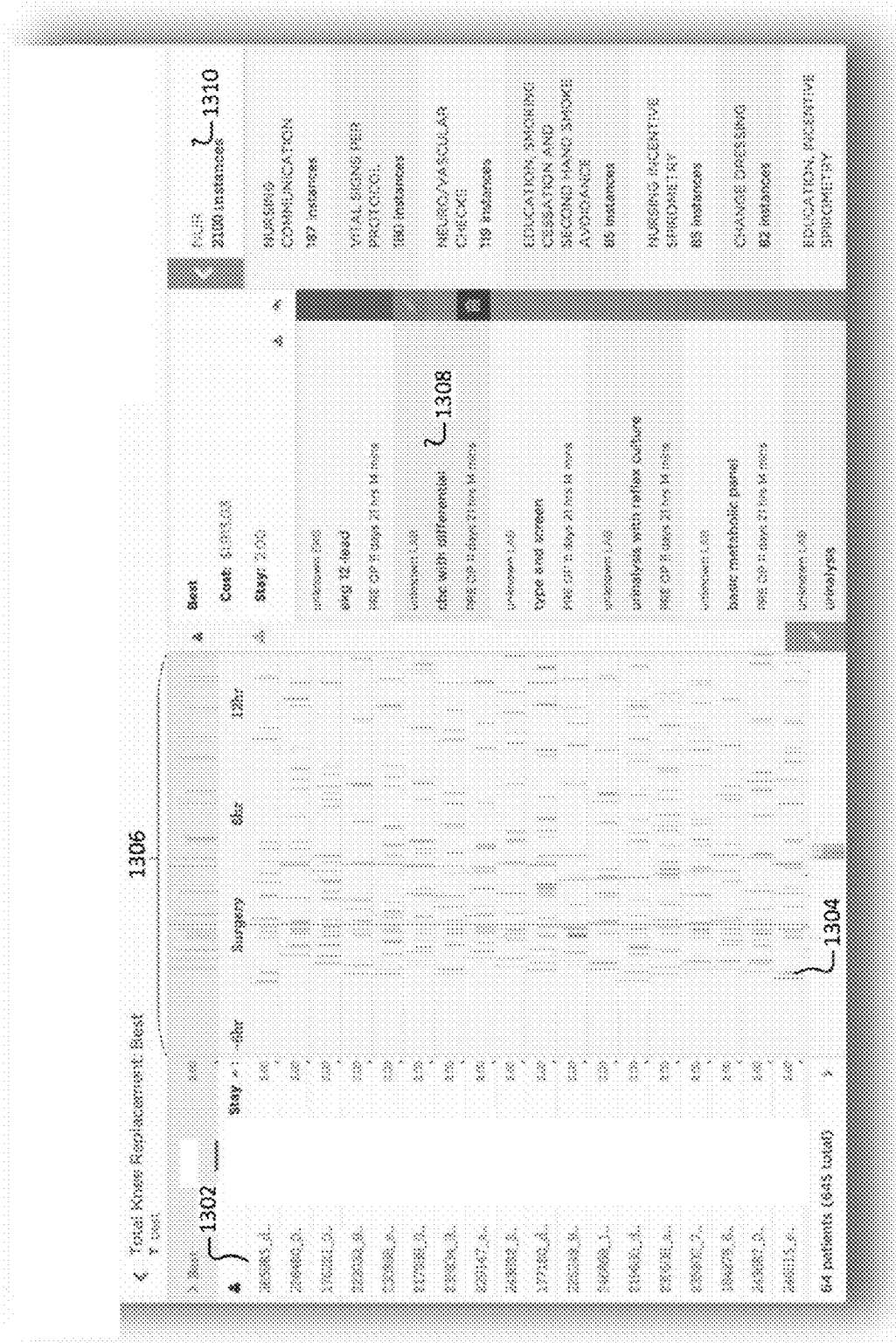
FIG. 13 is an example carepath consensus edit interface in some embodiments

FIG. 13 is an example carepath consensus edit interface in some embodiments. In this example, each patient identifier 1302 (anonymized and fictitious for this example) is associated with a series of events indicated in event sequence 1304. The consensus sequence, in this example, like FIG. 12, is 1306 at the top of the example carepath consensus interface. The consensus sequence 1306 may indicate the best (e.g., optimal in terms of benefit and/or cost) in view of the historical data associated with each patient identifier 1302. In various embodiments, the example carepath consensus interface and/or the consensus sequence 1306 may be or included in the consensus report.

The example carepath consensus edit interface may allow a user (e.g., medical professional) to interact with the patient event information and/or the consensus sequence 1306. In one example, the user may click on a patient or event and view event information 1308 associated with the selection. It will be appreciated that any number of events may be associated with the selection. In this example, the user may select an event associated with the synthetic category "unknown LAB." Activities 1310 that may be associated with an unknown lab may be depicted to allow the user a better understanding of the type of medical procedures that have been performed in the past, outcome information, likelihood of success, relative cost, order of procedures, and/or the like.

In various embodiments, the example carepath consensus edit interface may allow the user to edit the carepath and/or stored historical information (e.g., adding additional patient information). For example, a user (e.g., a medical professional) may add, remove, or edit events in via the editing interface. An updated consensus sequence may be generated and/or provided to the user based on the changes. In some embodiments, a prediction (e.g., regarding cost and/or length of stay) may be provided based, in part, on the changes.

FIGS. 14a-d depict an example of determining a partition based on scoring for autogrouping in some embodiments. In an example, there is a fixed space, S, of finite size. The nature of the space may be relevant only in so far as there is a way of clustering the space and scoring subsets. Referring to a graph G on S indicates a graph whose nodes are a collection of subsets where a node is connected to another node if and only if the two nodes have points in common. A partition includes one or more subsets. Each of the one or more subsets include all of the element(s) of S. For example, partition 1402 is a partition that includes subsets of all elements of S. Subsets 1404a-e include all elements of S. A union of all of the subsets 1404a-e is the partition 1402.

Figure 14A:
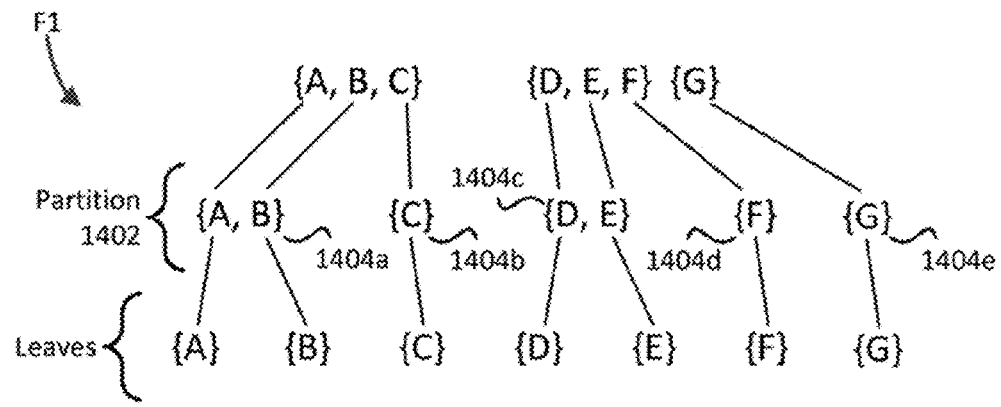
FIGS. 14a-d depict an example of determining a partition based on scoring for autogrouping in some embodiments.
Figure 14B:
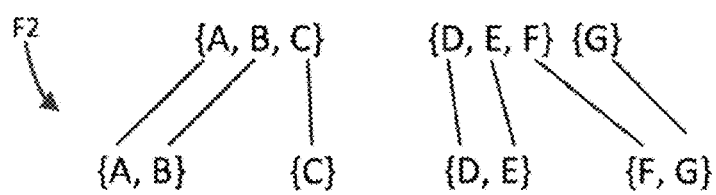
Figure 14C:
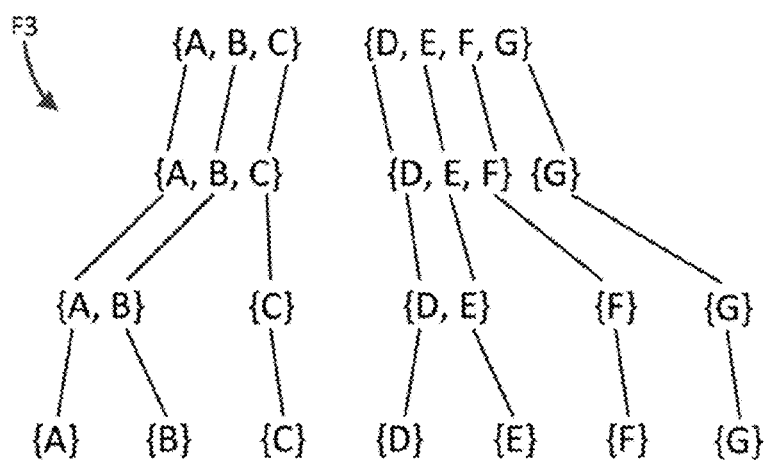

A forest F on S is a graph on S. A forest F is 'atomic' if every leaf in F is a singleton (e.g., a set with one member). FIG. 14a (i.e., F1) is an atomic forest because every leaf in F1 as depicted in FIG. 14a is a singleton. It will be appreciated that FIG. 14b (i.e., F2) is not an atomic forest since every leaf in F2 as depicted in FIG. 14b is not a singleton. For example, F2 includes leaves {A,B}, {D,E}, and {F,G}.

There is a partition R of S (in F1, {a,b,c}, {d,e,f}, {g}), called the roots, such that every set in F is reachable by a unique path from a root. N in F is either a leaf (e.g., a singleton in an atomic forest) or it is connected to nodes which form a partition (e.g., {a,b,c}->{a,b} and {c} in F1) of N. For a non-leaf node N we denote by C(N) the children of N. Notice the children of a leaf, namely C(leaf) is empty. We say that F' extends F if F and F' have the same leaves and every node in F is a node in F'. If the two forests are not equal, then F' contains a node which is the union of one or more roots in F. Example F3 (FIG. 14c) extends F1 (FIG. 14a).

Figure 14D:
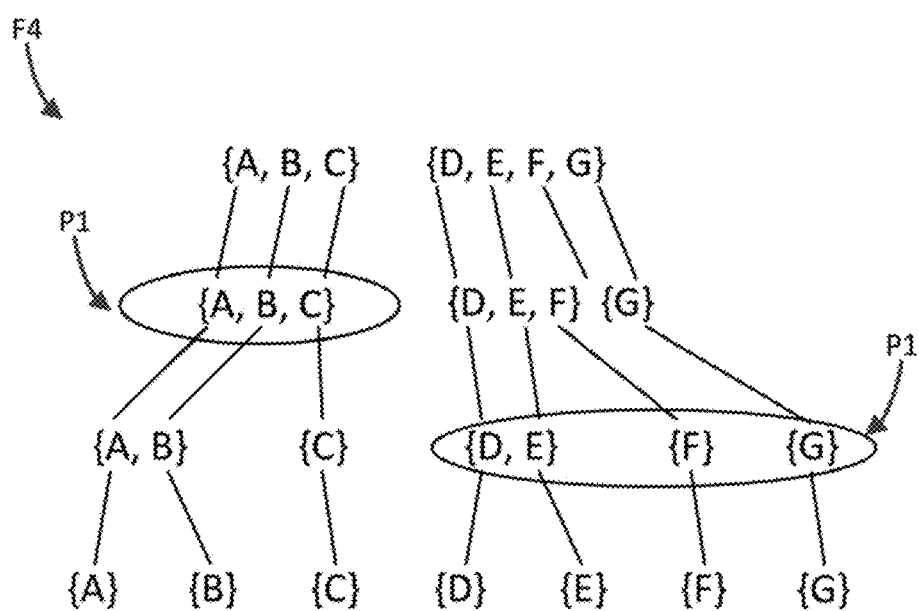

Partition P on S is subordinate to F1 if and only if every element of P is in F1. The circled partition P1 of F4 depicted in FIG. 14d, is an example of a subordinate partition {e.g., {a,b,c},{d,e},{f},and {g}} to F1.

Singletons(S) are denoted as the partition formed by taking {{x}|x in S}. That is, in the example in FIG. 14d, Singletons({a, b, c, d, e, f, g})={{a},{b},{c},{d},{e}, {f}, {g}}. This is the same as the set of leaves of an atomic forest. Let U(P), where P is any collection of subsets of S, denote the union of all the elements of P. U(Singletons(S))==S.

Partition P' on S is coarser than another partition P on S if and only if every element x' in P' is the union of elements x in P. In various embodiments, every partition on S is coarser than Singletons(S), and {S} is coarser than every partition on S. For instance, {{a,b,c},{d,e,f},{g}} is a coarser partition than {{a,b},{c},{d,e},{f},{g}}.

Figure 15:
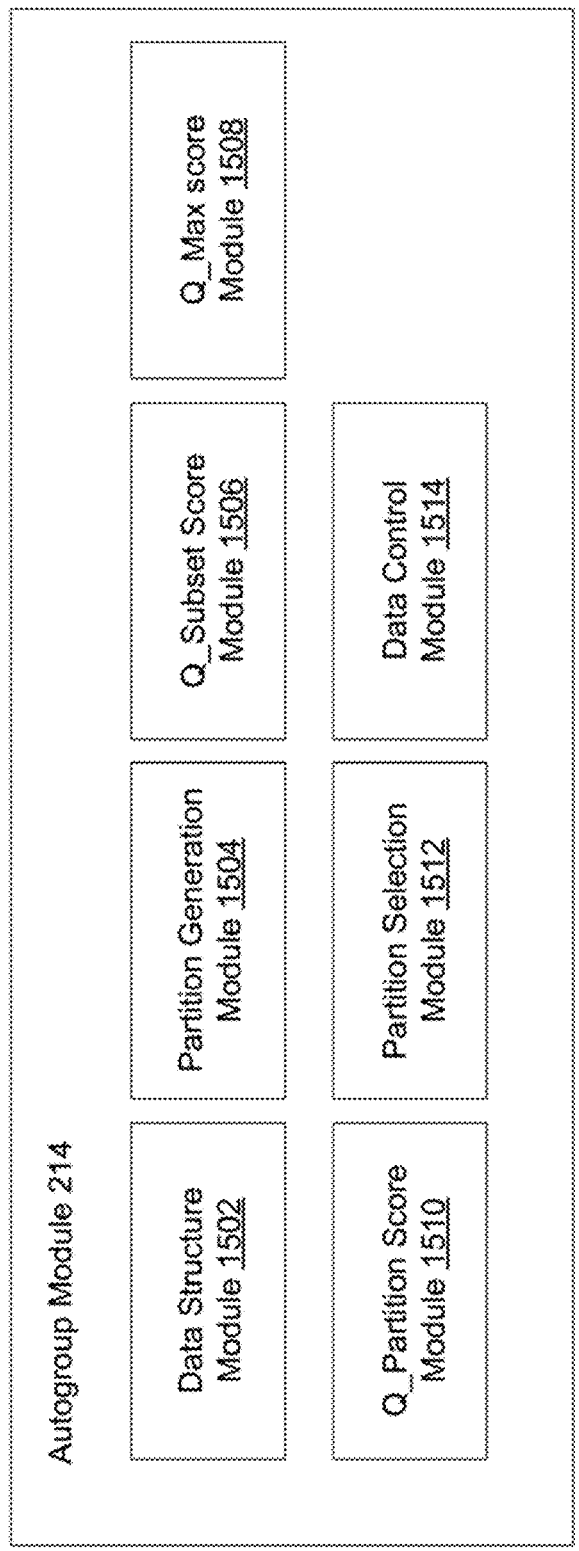
FIG. 15 depicts an example autogroup module in some embodiments.

FIG. 15 depicts an example autogroup module 214 in some embodiments. An autogroup module 214 may comprise a data structure module 1502, a partition generation module 1504, scoring function modules (e.g., a Q_subset score module 1506, a Q_max score module 1508, a Q_partition score module 1510), a partition selection module 1512, and a data control module 1514. Although the scoring function modules are discussed as including three modules, each performing a different scoring function, it will be appreciated that there may be any number of scoring function modules performing any number of scoring functions (e.g., one module performing a single scoring function capable of generating any number or type of scores). For example, the scoring functions may generate and/or maximize metric values of any number of metric functions.

In various embodiments, the data structure module 1502 receives data including a plurality of sets of data. The data may be received from any number of digital devices.

The partition generation module 1504 (e.g., a "dumper") forms a forest F utilizing the plurality of sets of data received by the data structure module 1502. For example, the partition generation module 1504 may generate a first partition of a forest F using the data received by the data structure module 1502. In some embodiments, the first partition may include leaves that are singletons of all elements from the data. In various embodiments, the first partition may include any number of sets of data. The first partition may include leaves for the forest, singletons, roots, sets of plurality of elements, and/or the like.

The partition generation module 1504 may generate the second partition of the forest F using the first partition. For example, the second partition may include at least one union of at least two sets of the first partition. Subsequent partitions may be generated in a similar fashion (e.g., based, at least in part, on including at least one union of at least two sets from the previous partition).

The partition generation module 1504 may generate the entire forest F before scoring partitions (or sets of partitions). For example, the partition generation module 1504 may generate the entire forest F before any or all of the scoring function modules score all or parts of partitions of the forest F.

In some embodiments, the partition generation module 1504 may generate the entire forest F while scoring is performed or in series with partition scoring (e.g., scoring of sets of partitions). For example, the partition generation module 1504 may generate the entire forest F while any or all of the scoring function modules score all or parts of partitions of the forest F. In another example, the partition generation module 1504 may generate one or more partitions of the forest F and then any number of the scoring function modules may score the generated partitions before the partition generation module 1504 generates one or more additional partitions of the forest F.

In various embodiments, the partition generation module 1504 may generate a partition of a forest F based on, at least in part, scores by any number of scoring function modules of previously generated partition(s) (or sets of partition(s)) of the forest F.

It will be appreciated that the partition generation module 1504 may not generate the entire forest F but may rather terminate generating partitions of the forest F before the forest F is completed. The partition generation module 1504 may determine whether to build a new partition of the forest F based on any number of the previously generated partition(s) of the forest F and/or scoring associated with all or parts of previously generated partition(s).

As discussed herein, the partition generation module 1504 may not generate all possible sets of data and/or all possible partitions of the forest F.

It will be appreciated that the partition generation module 1504 may utilize any number of hierarchical clustering techniques with techniques described herein. In one example, data and/or nodes are joined by epsilon (if 2 data subsets or nodes are within distance epsilon of each other then they are joined together). While this example standard technique has traditional limitations ("fixed epsilon") whereby a single epsilon may be unable to break up a space in a preferable manner, by scoring each subset of a partition, we can select subsets across a forest to identify and/or generate a selected partition (e.g., by auto-grouping subsets of a plurality of partitions).

One example of a hierarchical clustering technique, KNN on a finite metric space X is to compute the K nearest neighbors for each point with, for example, K=50. The partition generation module 1504 may start with INITIAL( ) being Singletons(X). Then at each step for 1<=k<=50, the partition generation module 1504 may connect x toy provided x and y are in the symmetric k nearest neighbors of one another. Note that if KNN(P,k) returns P for k<50, the partition generation module 1504 may bump k and try again instead of concluding that P is stable.

Another hierarchical clustering technique embodiment is defined on a weighted graph G (with positive weights) on a point set S. This hierarchical clustering technique is parameterized by a pre-determined real number delta where 1>delta>0. The partition generation module 1504 starts with delta=0 so INITIAL( ) being Singletons(S). For each partition P, we define wt(p,q), for p!=q in P, to be the sum of edge weights between the nodes in the graph which are a part of the subset p and those in the subset q in G, divided by |p|*|q|. The partition generation module 1504 is configured to take a partition P and make a new partition P' by joining all pairs of subsets (a,b) (where a, b are subsets in the partition P) when wt(a,b)>=delta*max(wt(p,q)) where the max is over all pairs of subsets p and q in the partition P.

There are any number of techniques for hierarchical clustering and any of them can be combined with a scoring function that satisfies example constraints on the scoring functions discussed herein.

The autogroup module 214 includes the Q_Subset score module 1506, the Q_Max score module 1508, and the Q_Partition score module 1510 which may utilize three scoring functions, respectively. The Q_Subset score module 1506 calculates a Q_Subset score for subsets of one or more partitions. The Q_Max score module 1508 calculates a Q_Max score based on the Q_Subset score (e.g., calculates a maximum score for a partition based on the Q_Subset score) for the subsets. The Q_Partition score module 1510 calculates a Q_Partition score for two or more partitions of the forest utilizing at least the Q_Subset Score for the subsets.

In various embodiments, the Q_Subset score module 1506 calculates Q_Subset scores (e.g., one for each subset of a partition). A function Q is defined on subsets of the space S and scores the properties which are to be grouped together in the auto-grouping process. For instance, in some embodiments, the Q_Subset score is a modularity score on a graph (so S are the nodes in the graph). The partition selection module 1512 may examine the data structure for a partition of the graph S with maximum modularity score(s).

The second scoring function, the Q_Partition score, may be an extension of the first scoring function Q to be defined on partitions of the space S. If the scoring function Q is defined on subsets of S, it can be extended to a partition function Q_Partition in various ways. One of the simplest ways to extend function Q to partitions is by defining Q_Partition (P) as the sum over p in P of Q(p) (e.g., for a partition P, Q_Partition (P)=sum{subsets p in P} Q(p)).

In various embodiments, Q_Partition must have the following property: Let P be an arbitrary partition of a subset of S, let p belong to P, and let q be a partition of p. P(q) is defined to be the partition of obtained by replacing p in P with the elements of q. Then, in this example, Q_Partition must have the following property for all P, p, q as described above:

(1) QP(P(q))>=QP(P) if and only if QP(q)>=Q({p})

In some embodiments, function Q does not need to come from a set function in this case. Functions Q_Partition which satisfy property (1) are, by definition, stable partition functions. A class of such functions is described as follows.

Let Q be any real-valued function defined on the set of non-empty subsets of S. Let A(p,q) be any function defined on pairs of non-empty subsets such that p is a subset of q. If:

(2) A(p,p)==1 and A(p,q)*A(q,r)=A(p,r), for all legal p,q,r
then we may extend the set function Q( ) to all partitions P by:
(3) QP(P)=sum A(p,U(P))Q(p)
p in P Note that all real numbers k, A(p,q)==(|p|/|q|)^k satisfies this property. Moreover, k==0 implies A(p,q)==1.

(1) holds for Q defined in (3). If QP and QP' are stable partition functions, then so is x*QP+y*QP' for x, y>=0. We also refer to stable partition functions on S as "partition scoring functions" for F.

For any scoring function of the form (3), a monotonically increasing function f may be chosen from the real numbers to itself and replace Q by Q'( )=f(Q( )). In particular, if f( ) is 'sufficiently invertible' (e.g., A( ) and Q( ) are >=0 and f( ) is invertible on the non-negative reals). QP(P) may be defined by:

(3') QP'(P)=f-inverse(sum A(p,U(P))f(Q(p)))
p in P

Since f(QP(P)) satisfies (1) and f( ) is monotonically increasing, the QP' in (3') also satisfies (1) and extends Q( ) on subsets of S. Concretely, if A==1 and Q( )=0 on sets, QP(P) may be defined to be the Euclidean norm of Q( ) on the individual elements of P, and still get a scoring function. Also can use the exponential function for f( ) without requiring Q to be non-negative.

In various embodiments, there may be extreme values under comparisons, using either <=or >=, for a function Q defined on partitions of subsets of S. Since Q may be replaced by -Q if the comparison is <=, it may be assumed without loss of generality that maximal values for Q (i.e., >=) are of interest. Specifically, a method for finding the F-subordinate partition on which Q is maximal, provided Q satisfies a simple property, is disclosed herein.

Given a scoring function Q_Partition on F, we can define a scoring function Q_max ( ) to be Q(p) if p is a leaf, and max(Q(p),Qmax(C(p))) if not. One consequence of this definition and requirement (1) on Q_Partition is that the maximal partition of a subset p (that is, the partition V of p for which Qmax(V) is maximal) is either p or the union of the maximal partitions of each element of C(p) (ties may be broken by taking the subset p instead the children).

In various embodiments, the auto-grouping method uses a hierarchical clustering process on S to compute F (i.e., to construct the forest F) and if Q_Partition is a scoring function on the roots R of F, we can find the Q_Max maximal partition of S subordinate to F. As we said above, the intuition here is that joining a scoring function Q( ) with hierarchical clustering provides a principled method for choosing among the partitions for the "Q-maximal partition."

The partition generation module 1504 begins with the original space S and forms a forest F described above. Specifically, in some embodiments, the generation module 1504 takes a partition P and returns a new partition P' which is coarser than P. Note that ({S})={S}. Any partition P such that generation module 1504 (P)=P is called dumper-terminal, and repeated applications must eventually reach a dumper-terminal partition. The sequence Singletons(S), Clumper(Singletons(S)), Clumper(Clumper(Singletons (S))), etc., terminates in a finite number of steps, and the union of all these partitions forms an atomic forest F whose roots are the elements in a C-terminal partition R, which are the roots of F.

One example process utilizing the scoring functions and generating partitions is as follows in the following pseudo-code:

```
P = INITIAL(S) // some initial partition - often Singletons( ), but it can
be anything
F = Tree(P) // node for every subset, remember connections, and have
max slot
                     // to hold partition of the node's set which has
                     maximal score
for (x in S) { {x}.max = {x} }
BEGIN
        P' = clumper(P)
        if P==P'
            then
                quit
            else
                UPDATE_Qmax(P',P)
END
UPDATE_Qmax(P',P)
    for (p in P') {
        if (!(p in P)) {
            Subset pSubset = AddSubset(p,F);
            if (Q(p) >= QP(C(p)))
                pSubset.maxPartition = p
                pSubset.Qmax = Q(p)
            else
                pSubset.Qmax = QP(C(p))
                pSubset.maxPartition = MAX_UNION(C(p))
        }
    }
    MAX_UNION({Ni})
        return the union of Ni.max
```

When this process terminates, the elements of the roots R of F may contain their maximal partitions, the union of which is the best partition in F of S.

The partition selection module 1512 finds a partition subordinate to the forest F that maximizes at least one scoring function. For example, the partition selection module 1512 may select a partition subordinate to the forest F that maximizes the scoring function QP.

In various embodiments, each subset of a partition (as discussed herein) may be associated with its own scores. For example, each subset of a partition may be associated with a different Q_Max score. The partition selection module 1512 may select subsets of unique elements from any number of different partitions of the forest F using the Q_Max score to generate and select a partition.

Figure 17:
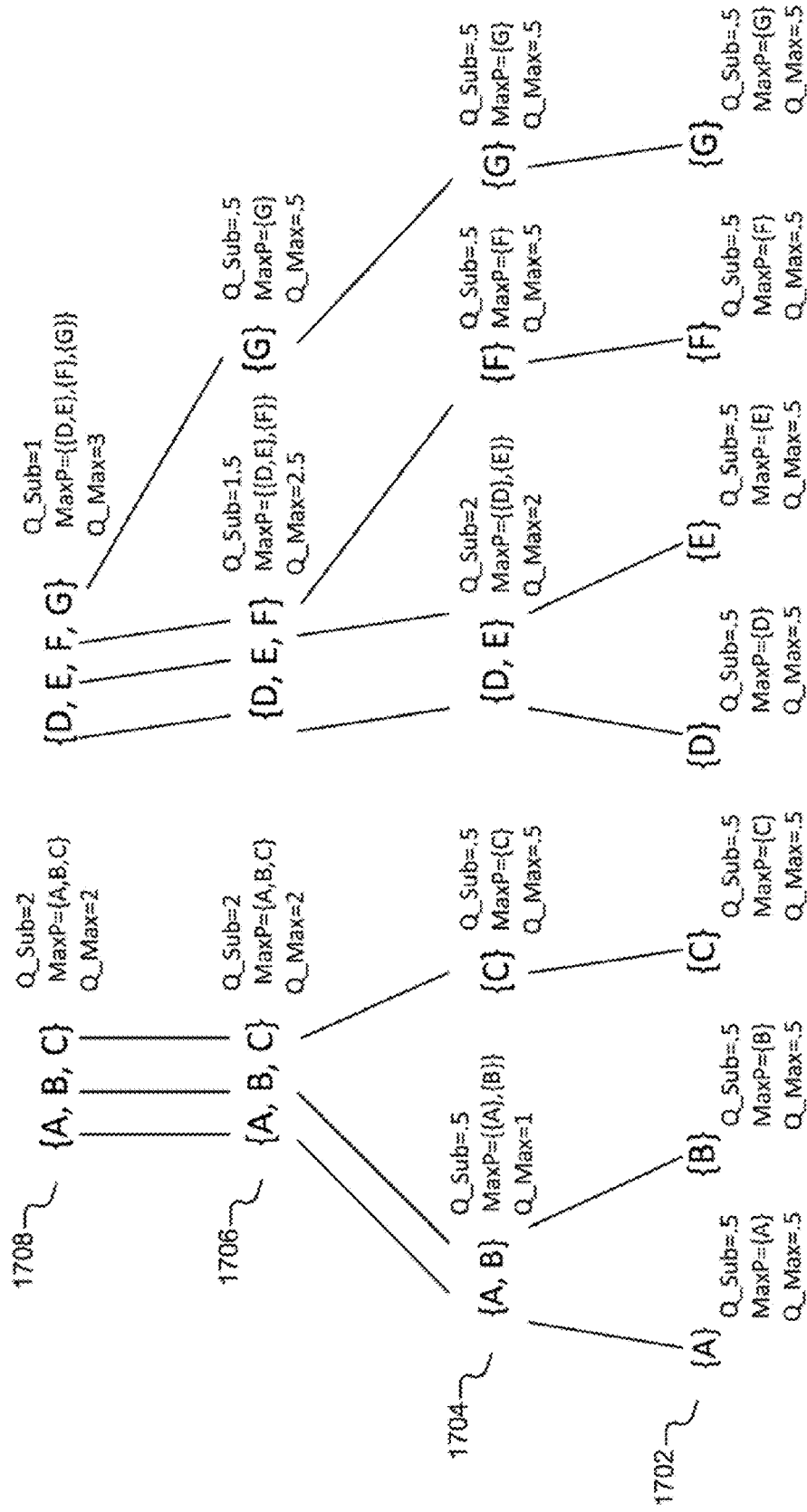
FIG. 17 is an example forest used to describe steps with regard to FIG. 16 in some embodiments.

For example, looking to FIG. 17, the partition selection module 1512 may select subset {A,B,C} from one partition and subsets {D,E}, {F}, AND {G} from another partition based on a scoring function. The selected subsets may then form (e.g., generate) a new selected partition P1 (e.g., a partition including subsets {A,B,C}, {D,E}, {F}, AND {G}). In this example, the partition selection module 1512 may select the subset {A,B,C} from the first partition utilizing the Q_Max score. In a further example, each subset of all partitions that include any of elements A, B, or C, may be associated with a separate Q_Max score. The maximum Q_Max score of all the sets that include any of the elements of A, B, or C is the subset {A,B,C}. As a result, the partition selection module 1512 selects that subset {A,B,C} in this example.

Similarly, each subset of all partitions that include any of elements D, E, F, or G, may be associated with a separate Q_Max score. The maximum Q_Max scores of all the sets that include any of the elements of D, E, F, or G are the subsets {D,E}, {F}, and {G} (i.e., the Q_Max scores associated with subsets {D, E, F, G}, {D, E, F}, and {G} are not the maximum when compared to the Q_Max scores of subsets {D,E}, {F}, and {G}). As a result, the partition selection module 1512 selects subsets {D,E}, {F}, and {G} in this example.

One example of a scoring function mentioned herein includes a modularity score for weighted graphs on a node set S. In some embodiments, the modularity score of a subset of a graph proportion of edges within a subset, the e's, and the a's which are the proportion of edges which cross the boundaries of the subset. The final score may be $e-a^2$. In various embodiments, the partition selection module 1512 selects and/or generates a partition by maximizing this score. The modularity partition scorer, QP, may be the sum of the modularity scores on the subsets within that partition.

Another example of a scoring function is a variant of entropy for a set S which has an associated classification: that is, a function cls: S->{1, 2, . . . , k} (i.e. you have a set and everything has some finite label.) For s subset of S, we define $p\_i(s)=|\{x \text{ in } s : cls*x)==i\}|/|s|$, provided $|s|!=0$. Then $Q(s)=sum\_\{classes\ i\} (p\_i(s)*log(p\_i(s)))$. The extension of the entropy scorer Q to a partition scorer, QP is given by the extension property (3) where $A(p,q)=|p|/|q|$. In other words, for a partition P, $QP(P)=sum\_\{p \text{ in } P\} (Q(p)*|p|/|U(P)|)$. Normally one wants to minimize the entropy and the subset scorer here is the negative of the traditional entropy score by maximizing the scoring function.

The data control module 1514 is configured to provide the selected and/or generated partition from the partition selection module 1512. In various embodiments, the data control module 1514 generates a report indicating the selected and/or generated partition from the partition selection module 1512. The report may include, for example, data sets, partitions, subsets, elements, data set identifiers, partition identifiers, subset identifiers, element identifiers, and/or the like. In some embodiments, the report may include a graph (e.g., see FIG. 14) with an indication of selected nodes whose member(s) include data of the selected and/or generated partition from the partition selection module 1512.

Figure 16:
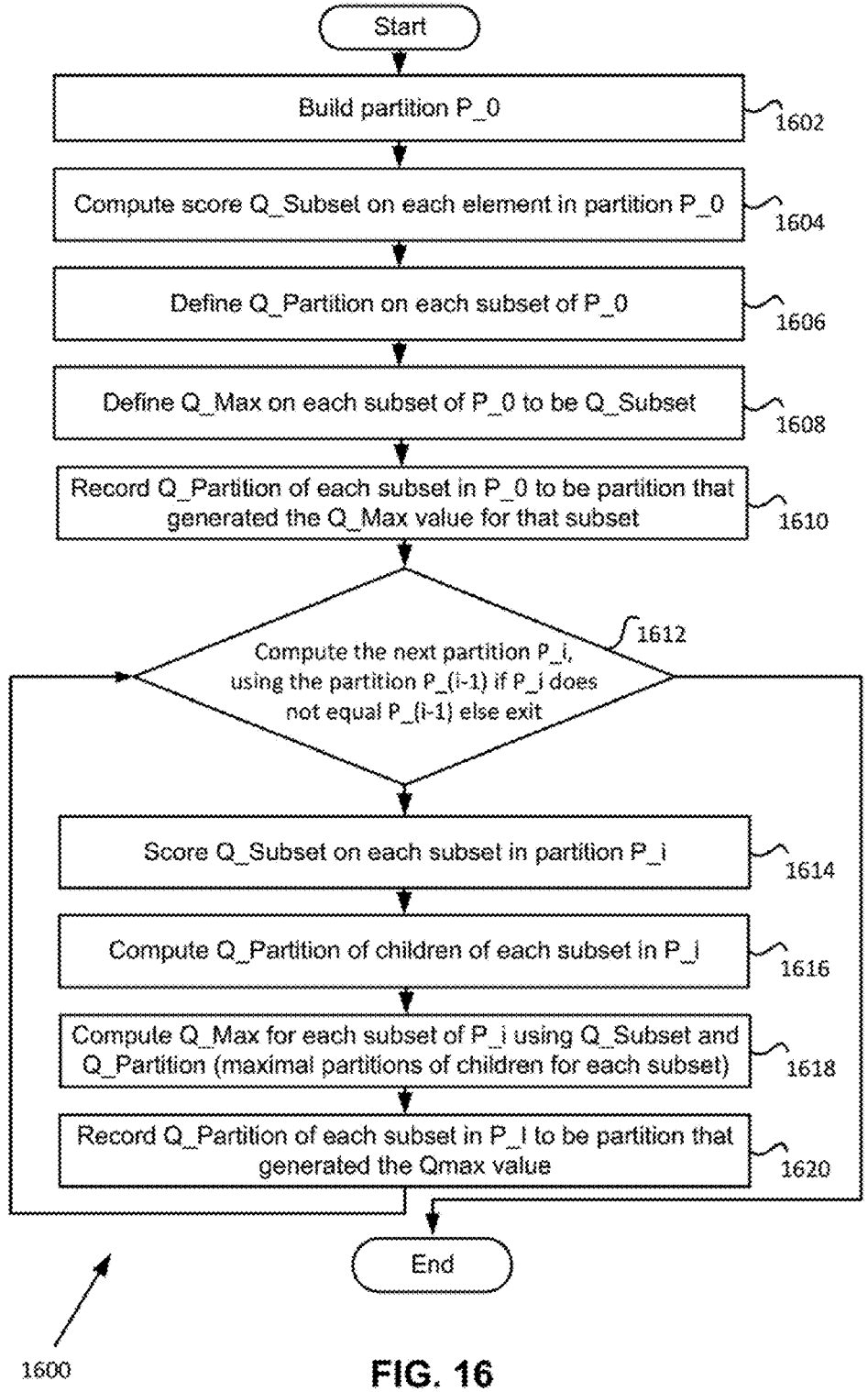
FIG. 16 is an example flowchart for autogrouping in some embodiments.

FIG. 16 is an example flowchart for autogrouping in some embodiments. In this example, the autogroup module 214 receives a set S={A, B, C, D, E, F, G} and performs autogrouping to identify a selected partition of a forest based on S. Non-limiting examples describing at least some of the steps in FIG. 16 will be described using the graph depicted in FIG. 17. The embodiment of the Q_Partition in this example is simply the sum over the subsets of the partition P of the Q_Subset scores on each subset. For example, if P={{A, B, C}, {D}, {E, F}, {G}}, then Q_Partition(P)= Q_Subset({A, B, C})+Q_Subset({D})+Q_Subset({E, F})+ Q_Subset({G}).

In step 1602, the data structure module 1502 receives the set S and the partition generation module 1504 generates an initial partition which are the singletons of the set S={A, B, C, D, E, F, G}, namely, P_0={{A}, {B}, {C}, {D}, {E}, {F}, {G}}. This is illustrated in FIG. 17 as the bottom row (1702) of the depicted forest.

In step 1604, the Q_subset score module 1506 computes the Q_Subset score on each subset of the partition P_0. In this example, the Q_subset score module 1506 scores each singleton subset with a value of 0.5. This score is shown in FIG. 17 for each subset of partition 1702 as Q_Sub=0.5.

In step 1606, the Q_partition score module 1510 computes the maximal partition of each subset a of P_0 from the children of the subset a in the constructed forest. Since the subsets a in P_0 have no children in the forest, the maximal partition of the children of the subset a is itself. Namely, for each subset a in P_0, MaximalPartitionChildren(a)=a.

In this example, the Q_partition score module 1510 computes the maximal partition of each subset as itself. This is shown in FIG. 17 for each subset of partition 1702 as MaxP={A} for subset {A}, MaxP={C} for subset {C}, MaxP={D} for subset {D}, MaxP={E} for subset {E}, MaxP={F} for subset {F}, and MaxP={G} for subset {G}.

In step 1608, the Q_max score module 1508 computes Q_Max on each subset of P_0. Recall that since the subsets in P_0 do not have any children, for each subset a in P_0, $$Q\_Max(a) = \max(Q\_Subset(a),$$

$$Q\_Partition(MaximalPartitionChildren(a)))$$

$$= \max(Q\_Subset(a), Q\_Partition(a))$$

$$= \max(Q\_Subset(a), Q\_Subset(a)) = Q\_Subset(a)$$

$$= 0.5$$

In this example, the Q_max score module 1508 scores each subset with a value of 0.5. This Q_Max score is shown in FIG. 17 for each subset of partition 1702 as Q_Max=0.5.

In step 1610, we optionally record the maximal partition of each subset a in P_0 to be partition of the subset a that generated the Q_Max for that subset. Thus we record the MaximalPartition(a)=a in this initial partition.

In step 1612, the data structure module 1502 computes the next partition P_1 (the row labeled 1704 in FIG. 17"). Namely, in this example, the data structure module 1502 groups subsets {A} and {B} into the subset {A, B} and subsets {D} and {E} into subset {D, E}. The data structure module 1502 preserved the subsets {C}, {F}, and {G} from the partition P_0 in the partition P_1.

In various embodiments, the data structure module 1502 may determine whether the system ends and/or whether a new partition is to be computed. It will be appreciated that the data structure module 1502 may perform the determination based on any number of ways. In some embodiments, the data structure module 1502 determines if the next generated partition is equal to the previous partition. If the two partitions are equal (e.g., have the same subsets), the method may terminate, otherwise the method may continue to step 1614.

In some embodiments, the data structure module 1502 terminates the method after a predetermined number of partitions are generated, if a predetermined number of roots are found, and/or the like. In various embodiments, the data structure module 1502 may terminate the method if a predetermined number of subsets are present in a computed partition. In another example, the data structure module 1502 may terminate the method after a predetermined period of time, a predetermined period of memory usage, or based on any threshold (e.g., the threshold being calculated based on the amount of data received).

In step 1614, the Q_subset score module 1506 computes the Q_Subset score on each subset of the partition P_1. In this example, the Q_subset score module 1506 computes Q_Subset({A, B})=0.5 and Q_Subset({D,E})=2. As was discussed in the paragraph above describing 1604, Q_Subset of each singleton subset is 0.5 (e.g., the previous Q_Subset score for singleton subsets in 1704 remains unchanged from 1702. These scores are associated with each subset and are visualized in the FIG. 17 as Q_Sub in 1704.

In step 1616, the Q_partition score module 1510 then computes the maximal partition at the children of each subset of P_1. The maximal partition of the children of the subsets {C}, {F}, and {G} are again the original singleton subset. The maximal partition of the children {A, B} is the set including the maximal partitions of the children of {A, B}, namely {{A}, {B}} as depicted in partition 1704 in FIG. 17. Similarly the maximal partition of the children of {D, E} is the set {{D}, {E}} as also depicted in partition 1704 in FIG. 17.

In step 1618, the Q_max score module 1508 computes the Q_Max on each subset of P_1. Recall Q_Max(a)=max (Q_Subset(a), Q_Partition(MaximalPartitionChildren(a)). For the subset {A, B}:

$$Q\_Max(\{A, B\}) = \max(Q\_Subset(\{A, B\}), Q\_Partition(\{\{A\}, \{B\}\}))$$

$$= \max(.5, Q\_Subset(\{A\}) + Q\_Subset(\{B\})$$

$$= \max(0.5, 1)$$

$$= 1$$

For the subset {D, E}:

$$Q\_Max(\{D, E\}) = \max(Q\_Subset(\{D, E\}), Q\_Partition(\{\{D\}, \{E\}\}))$$

$$= \max(2, Q\_Subset(\{D\}) + Q\_Subset(\{E\})$$

$$= \max(2, 1)$$

$$= 2.$$

As displayed in partition 1704 of FIG. 17, Q_Max of {A,B} is 1 and Q_Max of {D,E} is 2. The Q_Max of singletons {C}, {F}, and {G} in partition 1704 remain consistent with the respective subsets in partition 1702. Namely, the Q_Max of each of {C}, {F}, and {G} is 0.5.

In step 1620, we optionally record the maximal partition of each subset a in P_1 that resulted in the Q_Max score. As seen above and in FIG. 17, MaxPartition({A, B})={{A}, {B}} and MaxPartition({D, E})={D, E}.

Now repeat step 1612. The data structure module 1502 computes the next partition P_2, depicted in FIG. 17 as row (partition) 1706. In various embodiments, the data structure module 1502 may determine whether the system ends and/or whether a new partition is to be computed. It will be appreciated that the data structure module 1502 may perform the determination based on any number of ways.

In step 1614, the Q_subset score module 1506 computes the Q_Subset score on each subset of the partition P_2. In this example, the Q_subset score module 1506 computes Q_Subset({A, B, C})=2 and Q_Subset({D, E, F})=1.5. Again, Q_Subset({G})=0.5. These scores are recorded with each subset and are visualized in the FIG. 17 in partition 1706.

In step 1616, the Q_partition score module 1510 computes the maximal partition at the children of each subset of P_2. The maximal partition of the children {G} is the subset {G}. The maximal partition of the children {A, B, C} is the set consisting of the maximal partitions of the children of {A, B, C}, namely {MaxPartition({A,B}), MaxPartition({C})}={{A}, {B}, {C}}. Similarly the maximal partition of the children of {D, E, F} is the set {MaxPartition({D, E}), MaxPartition({F})}={{D, E}, {F}}.

This is shown in FIG. 17 for each subset of partition 1706 as MaxP={A,B,C} for subset {A,B,C}, MaxP={{D,E},{F}} for subset {D,E,F,}, and MaxP{G} for subset {G}.

In step 1618, the Q_max score module 1508 computes the Q_Max on each subset of P_2. Recall Q_Max(a)=max (Q_Subset(a), Q_Partition(MaximalPartitionChildren(a)). For the subset {A, B, C}:

$$Q\_Max(\{A, B, C\}) = \max(Q\_Subset(\{A, B, C\}),$$
$$Q\_Partition(\{\{A\}, \{B\}, \{C\}\}))$$
$$= \max(2, Q\_Subset(\{A\}) + Q\_Subset(\{B\}) + Q\_Subset(\{C\}))$$
$$= \max(2, 1.5)$$
$$= 2$$

For the subset {D, E, F}:

$$Q\_Max(\{D, E, F\}) = \max(Q\_Subset(\{D, E, F\}),$$
$$Q\_Partition(\{\{D, E\}, \{F\}\}))$$
$$= \max(1.5, Q\_Subset(\{D, E\}) + Q\_Subset(\{F\}))$$
$$= \max(1.5, 2.5)$$
$$= 2.5$$

As displayed in partition 1706 of FIG. 17, Q_Max of {A,B,C} is 2 and Q_Max of {D,E,F} is 2.5 The Q_Max of singleton{G} in partition 1706 remains consistent with the respective subset in partition 1704. Namely, the Q_Max {G} is 0.5.

In step 1620, we optionally record the maximal partition of each subset a in P_2 that resulted in the Q_Max score. As seen above, MaxPartition({A, B, C})={{A, B, C}} and MaxPartition({D, E, F})={{D, E}, {F}}.

Now repeat step 1612. The data structure module 1502 computes the next partition P_3, depicted in FIG. 17 as row (partition) 1708. The data structure module 1502 may determine whether the system ends and/or whether a new partition is to be computed.

In step 1614, the Q_subset score module 1506 computes the Q_Subset score on each subset of the partition P_3. In this example, the Q_subset score module 1506 computes Q_Subset({A, B, C})=2 and Q_Subset({D, E, F, G})=1. These scores are recorded with each subset and are visualized in FIG. 17 in partition 1708.

In step 1616, the Q_partition score module 1510 computes the maximal partition at the children of each subset of P_3. The maximal partition of the children {A, B, C} is the set consisting of the maximal partitions of the children of {A, B, C}, namely {MaxPartition({A,B, C})}={{A, B, C}. Similarly the maximal partition of the children of {D, E, F, G} is the set {MaxPartition({D, E, F}), MaxPartition ({G})}={{D, E}, {F}, {G}}.

This is shown in FIG. 17 for each subset of partition 1708 as MaxP={A,B,C} for subset {A,B,C} and MaxP={{D,E}, {F},{G}} for subset {D,E,F,G}.

In step 1618, the Q_max score module 1508 computes the Q_Max on each subset of P_3. Recall Q_Max(a)=max (Q_Subset(a), Q_Partition(MaximalPartitionChildren(a)). For the subset {A, B, C}:

$$Q\_Max(\{A, B, C\}) = \max(Q\_Subset(\{A, B, C\}),$$
$$Q\_Partition(\{A, B, C\}))$$
$$= \max(2, Q\_Subset(\{A, B, C\}))$$
$$= 2$$

For the subset {D, E, F, G}:

$$Q\_Max(\{D, E, F, G\}) = \max(Q\_Subset(\{D, E, F, G\}),$$
$$Q\_Partition(\{\{D, E\}, \{F\}, \{G\}\}))$$
$$= \max(1, Q\_Subset(\{D, E\}) + Q\_Subset(\{F\}) + Q\_Subset(\{G\}))$$
$$= \max(1.5, 3)$$
$$= 3$$

As displayed in partition 1708 of FIG. 17, Q_Max of {A,B,C} is 2 and Q_Max of {D,E,F,G} is 3.

In step 1620, we optionally record the maximal partition of each subset a in P_3 that resulted in the Q_Max score. As seen above, MaxPartition({A, B, C})={{A, B, C}} and MaxPartition({D, E, F, G})={{D, E}, {F}, {G}}.

Although not depicted in method 1600, the method may continue. For example, the partition selection module 1512 may identify and/or generate a preferred partition from that maximizes one or more scoring functions. In this example, the preferred partition is the MaxPartition. As discussed immediately above, the maximal partition of each subset in P_3 is As seen above, MaxPartition({A, B, C})={{A, B, C}} and MaxPartition({D, E, F, G})={{D, E}, {F}, {G}}. The partition selection module 1512 may identify and/or generate the auto-grouped partition {{A, B, C}, {{D, E}, {F}, {G}}.

The data control module 1514 may provide the identified and/or generated auto-grouped partition in a report and/or identify the auto-grouped partition in data or a graph.

Figure 18:
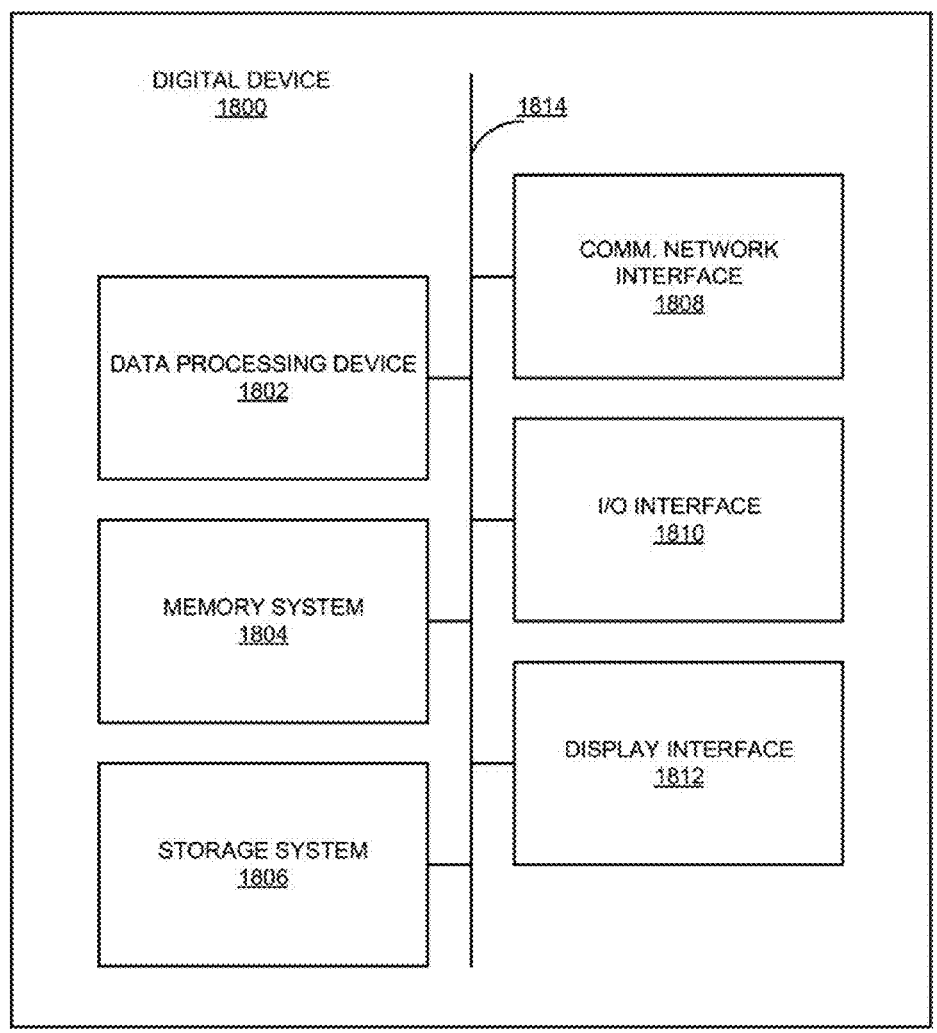
FIG. 18 is a block diagram of an exemplary digital device.

FIG. 18 is a block diagram of an exemplary digital device 1800. The digital device 1800 comprises a data processing device (e.g., a processor) 1802, a memory system 1804, a storage system 1806, a communication network interface 1808, an I/O interface 1810, and a display interface 1812 communicatively coupled to a bus 1814. The processor 1802 is configured to execute executable instructions (e.g., programs). In some embodiments, the processor 1802 comprises circuitry or any processor capable of processing the executable instructions.

The memory system 1804 is any memory configured to store data. Some examples of the memory system 1804 are storage devices, such as RAM or ROM. The memory system 1804 may comprise the cache memory. In various embodiments, data is stored within the memory system 1804. The data within the memory system 1804 may be cleared or ultimately transferred to the storage system 1806.

The storage system 1806 is any storage configured to retrieve and store data. Some examples of the storage system 1806 are flash drives, hard drives, optical drives, and/or magnetic tape. The storage system 1806 may comprise non-transitory media. In some embodiments, the digital device 1800 includes a memory system 1804 in the form of RAM and a storage system 1806 in the form of flash data. Both the memory system 1804 and the storage system 1806 comprise computer readable media which may store instructions or programs that are executable by a computer processor including the processor 1802.

The communication network interface (com. network interface) 1808 may be coupled to a network (e.g., communication network 110) via the link 1816. The communication network interface 1808 may support communication over an Ethernet connection, a serial connection, a parallel connection, or an ATA connection, for example. The communication network interface 1808 may also support wireless communication (e.g., 802.17a/b/g/n, WiMax). It will be apparent to that the communication network interface 1808 may support many wired and wireless standards.

The optional input/output (I/O) interface 1810 is any device that receives input from the user and output data. The optional display interface 1812 is any device that is configured to output graphics and data to a display. In one example, the display interface 1812 is a graphics adapter. It will be appreciated that not all digital devices 1800 comprise either the I/O interface 1810 or the display interface 1812.

The hardware elements of the digital device 1800 are not limited to those depicted in FIG. 18. A digital device 1800 may comprise more or less hardware elements than those depicted. Further, hardware elements may share functionality and still be within various embodiments described herein. In one example, encoding and/or decoding may be performed by the processor 1802 and/or a co-processor, such as a processor located on a graphics processing unit (GPU).

The above-described functions and components may be comprised of instructions that are stored on a storage medium such as a computer readable medium (e.g., a non-transitory computer readable medium). The instructions may be retrieved and executed by a processor. Some examples of instructions are software, program code, and firmware. Some examples of storage medium are memory devices, tape, disks, integrated circuits, and servers. The instructions are operational when executed by the processor to direct the processor to operate in accord with embodiments of the present invention.

Figure 19:
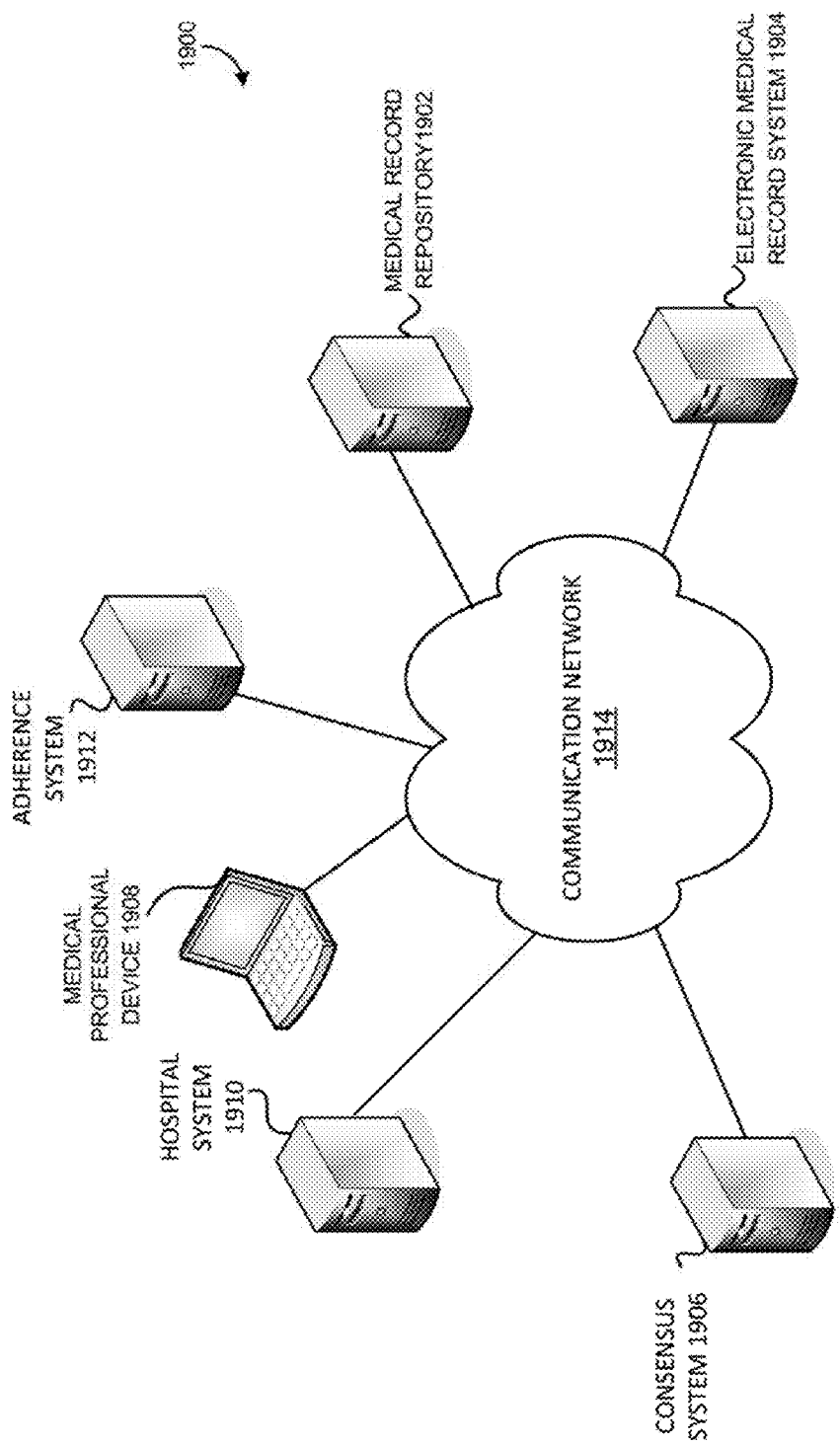
FIG. 19 is an example environment in which embodiments may be practiced.

FIG. 19 is an example environment 1900 in which embodiments may be practiced. In various embodiments, data analysis for consensus sequence generation and/or outcome prediction may be performed locally (e.g., with software and/or hardware on a local digital device), across a network (e.g., via cloud computing), or a combination of both. There are many advantages between performing all or some activities locally and many advantages of performing all or some activities over a network. Although FIG. 19 is described regarding medical systems and devices, as discussed herein, it will be appreciated that there embodiments described herein may be used in any number of devices.

Environment 1900 comprises a medical record repository 1902, electronic medical record system 1904, a consensus system 1906, a medical professional device 1908, a hospital system 1910, and an adherence system 1912 in communication over a communication network 1914. Environment 1900 depicts an embodiment wherein functions are performed across the communication network 1914. The consensus system 1906 may be utilized to create and/or modify one or more carepaths associated with any number of medical conditions. As discussed herein, a carepath (e.g., clinical pathway, care process model, or pathway) is a representation of a sequence of events for a medical professional, medical group, or facility to follow when treating a patient with a particular medical treatment. An event, in some embodiments, is defined as a lab, order, medication or surgery. Events may be mapped to and/or from EMR data. Each carepath may include events associated with the treatment of the medical condition. The consensus system 1906 may perform analysis and generation of an consensus sequence report and/or prediction based on consensus sequences to assist in the generation of carepaths.

The medical record repository 1902 may be similar to the medical record repository 102. The electronic medical record system 1904 may be similar to the electronic medical record system 104. The consensus system 1906 may be similar to the consensus system 106. The medical professional device 1908 may be similar to the medical professional device 108. Similarly, the communication network 1914 may be similar to the communication network 110. The medical record repository 1902, electronic medical record system 1904, consensus system 1906, medical professional device 1908, hospital system 1910, and adherence system 1912 may be or include any number of digital devices. A digital device is any device that comprises memory and a processor. Digital devices are further described in FIG. 18. A system may be any number of digital devices.

In various embodiments, the medical record repository 1902 may include any amount of historical information (e.g., historical patient data). The medical record repository 1902 may include, for example, an Electronic Medical Record (EMR) database. In one example, the medical record repository 1902 may collect information from any number of medical professionals and related professionals (e.g., information from insurance companies) regarding any number of patients. For example, the medical record repository 1902 may include medical records indicating treatment, labs, testing, operations, medicines, and/or the like related to any number of patients.

In various embodiments, the medical record repository 1902 may include any amount of information regarding patients at multiple medical facilities and/or associated with any number of medical personnel (including medical professionals). In some embodiments, the historical data of the medical record repository 1902 may include historical information regarding any number of patients.

The electronic medical record system 1904 may include any number of patient records (e.g., patient data) for any number of patients. In one example, the electronic medical record system 1904 may receive and provide medical information regarding any number of patients for any number of physicians. In one example, the electronic medical record system 1904 may include local patient information (e.g., patient information for any number of patients of a hospital or the like) and/or current information (e.g., labs to be performed and/or the like).

The medical professional device 1908 is any device associated with a medical professional (e.g., medical doctor). In various embodiments, a physician may utilize the medical professional device 1908. In various embodiments, the medical professional device 1908 may provide patient information to the medical record repository 1902 and/or the electronic medical record system 1904. The medical professional device 1908 may receive consensus sequence report (e.g., carepaths) based on patient historical data and/or provide predictions based on the consensus sequences discovered and current patient information. The medical professional and/or the medical professional device 1908 may assess the consensus sequence report in view of a patient to determine a preferred course of action.

The hospital system 1910 may include any number of digital devices to create carepaths, distribute carepaths, create adherence paths, track adherence, assess carepaths and adherence, and the like relative to that hospital systems patients and medical professionals (e.g., including all facilities, medical professional groups, and/or the like). In various embodiments, the medical professional device 1908 may be a part of the hospital system 1910. While the hospital system 1910 is labeled as "hospital," it will be appreciated that any facility or medical professional group (e.g., clinic, group of medical professionals, insurance system, and/or the like) may be in place of or in addition to the hospital system 1910.

The communication network 1914 may be any network that allows digital devices to communicate. The communication network 1914 may be the Internet and/or include LAN and WANs. The communication network 1914 may support wireless and/or wired communication.

The consensus system 1906 is a digital device that may be configured to analyze data (e.g., historical patient information from the electronic medical record system 1904) to generate the consensus sequence report (e.g., a report indicating a consensus temporal patterns from past records of sequences of actions performed). The consensus system 1906 may be utilized to create and/or modify carepaths.

The consensus system 1906 may also receive patient information from the medical professional device 1908 and provide a course of action or assessment based on the received patient information and the consensus sequences discovered. One example consensus system 1906 is described with regard to FIG. 2.

Various embodiments described herein provide an interface for exploration of patient event and encounter data drawn from electronic medical records (e.g., electronic health records or EHR). The data may be prepared according to a flat file specification and loaded via a custom transformation process. This transformation may convert the information from electronic health records data into a series of events. In one example, the events may be defined as Labs, Orders, Meds and Surgery.

In one example, the consensus system 1906 allows client hospitals, insurance companies, and the like to identify internal best practices in treating surgical patients by analyzing the patient data for patterns of treatment. A given "patient encounter" in this context and example is defined to be the interactions of the patient with the hospital staff which relate to surgery or other medical condition. This data may take the form of some clinical information (diagnoses, lab results, etc.) and a sequence of "events," which may be timestamped "treatment codes"—that is, an event is a pair, <code,time>. The meaning of a timestamp may vary; it may be when the coded interaction (e.g., giving the patient a specific dose of a medication) occurred, when medicine or a procedure was ordered, when the order was logged in the EMR system, or some other time. In an example, an event is a specific interaction (encoded as a 32-bit integer) and an approximate time of that interaction encoded as a floating-point number.

The consensus system 1906 may take a large number (in the tens to hundreds of thousands) of complex encounters (each with thousands to tens of thousands of events) and identify patterns of consensus treatments—that is, patterns of interactions which the client practitioners have found consistently effective. A series of such events may be considered to be a a "consensus carepath" discussed herein. A consensus carepath may be a summary of the agreed-upon treatments culled from data (e.g., from the EMR). Such a consensus can be put forward as a template (e.g., a carepath) for patient treatment. The use of such templates is of great value, leading to improved outcomes and reduced costs. Historically, creation of rules for treatment were done "by hand" (that is, by the use of committees poring over relatively small numbers of patient records and published literature) and could take months of work and be biased by the still narrow collective experience (a few hundred encounters) of the members of the committee. The consensus system 1906 can do this in a tiny fraction of the time while using far more data in an unbiased manner.

In some embodiments, when a user logs into the system (e.g., into the consensus system 106), the user may be presented with available episodes for exploration. Episodes can range from acute episodes, such as surgical procedures to non-acute episodes. Selecting a particular episode may lead to different ways of examining and exploring data.

The consensus system 1906 may assist to identify consensus regarding a particular treatment to create a carepath. As discussed herein, a carepath (e.g., clinical pathway, care process model, or pathway) is a representation of a sequence of events for a medical professional, medical group, or facility to follow when treating a patient with a particular medical treatment. An event, in some embodiments, is defined as a lab, order, medication or surgery. Events may be mapped to and/or from EMR data.

The consensus system 1906 may enable refinement and modifications to an existing carepath. In some embodiments, the consensus system 1906 or an adherence system, may further track adherence to all or part of the carepath by medical professionals, groups of medical professionals, and/or facilities.

The consensus system 1906 may provide an interface to enable modelling and/or refining any number of carepaths. In some embodiments, a carepath may be shown in a calendar style view with configurable periods of time for each column. Adding or moving events can be done simply by searching for an event and then moving it to the desired time period on the carepath. Carepaths may have two states: draft carepaths can be edited, while deployed carepaths are read-only. Deployed carepaths may be visible to users that access the interface, but, in some embodiments, may only be changed and/or deleted by an owner of the carepath.

In various embodiments, the consensus system 1906 may enable a user to log in and the consensus system 1906 may authenticate the user. Based on the login, the consensus system 1906 may allow the user access to any number of deployed or draft carepaths available to the user, and/or recognize the user as the owner of a deployed carepath (which may provide the user rights to delete and/or change the deployed carepath). The user may start with a created consensus based carepaths or a user may choose a new blank carepath.

The interface presented by the consensus system 1906 or the adherence system 1912 may present a dashboard summary of procedure data. This dashboard summary may enable the user to explore operational data by physician or by facility. In addition, adherence scores (discussed herein) may be shown for deployed carepaths. For each physician or each facility, the user may examine adherence details at the event level.

The adherence system 1912 may assists in determining the degree to which a medical professional, a group of medical professionals, groups, facilities, systems, and/or the like follow significant portions of a carepath. For example, of a carepath for diabetes, there may be 10-20 specific events (e.g., treatments, labs, and/or the like) of a much larger carepath that are particularly related to improved health of patient (e.g., when compared to all events of the entire carepath). The adherence system 1912 may identify the degree to which a medical professional or system "adheres" to or complies with portions of the larger carepath.

In determining the extent to which a medical professional follows each of the specific events (i.e., adherence objects) identified in the larger carepath, the adherence system 1912 may identify which events are not being followed, which events are being followed, and the outcome of those patients (at least the outcome during a measuring period). Outcome may be measured based on change in medical condition, requirements for other treatment, length of stay, number of return visits to a medical system, and/or the like.

The adherence system 1912 may be used to create an adherence path of a carepath, generate adherence scores related to any number of patients of one or more medical professionals, the patients sharing a medical condition during a predetermined time period. The adherence system 1912 may generate reports based on the adherence score(s) to assist in updating a related carepath, updating or changing adherence objects, identifying best practices for medical professionals, identify nonconforming medical professionals and exactly what they are not performing, identify outcomes of patients with treatment that did not conform to their particular carepath, and/or the like.

In various embodiments, the adherence system 1912 may retrieve medical records of patients with: (1) a certain medical condition associated with a carepath; (2) who are under the care of specific medical professionals; and (3) received treatment for the certain medical condition during a specific time frame. The adherence system 1912 is discussed with regard to FIG. 21.

Figure 20:
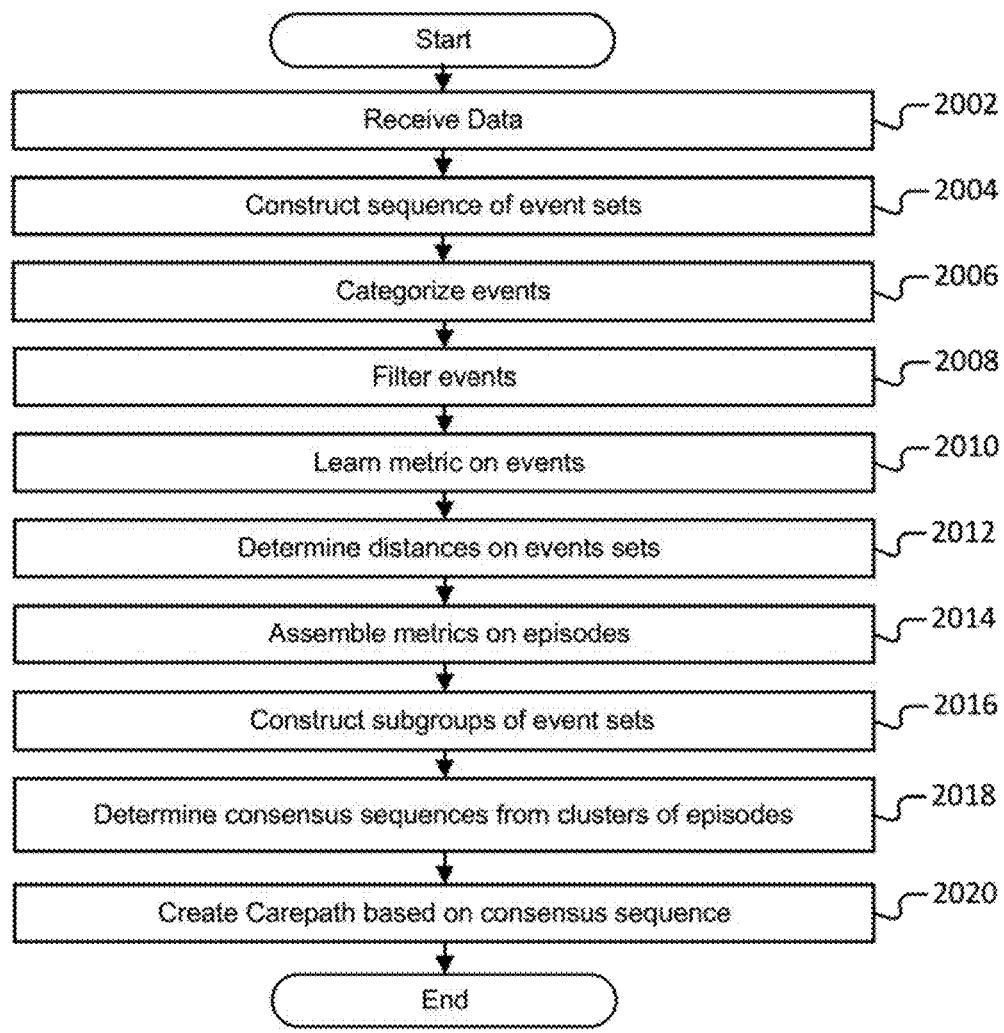
FIG. 20 is a flowchart of a method for generating a carepath based on consensus temporal patterns in some embodiments.

FIG. 20 is a flowchart of a method for generating a carepath based on consensus temporal patterns in some embodiments. The carepath may be the same or similar to that discussed as being generated with regard to FIG. 3.

In step 2002, historical information is received. For example, the event set construction module 2002 may receive historical information (e.g., historical medical information) regarding any number of patients from an EMR system of the medical record repositor(ies) 102.

In various embodiments, the event set construction module 202 is configured to construct event sets from the received data and episodes from events. The events in an event set are actions (e.g., interactions) whose order may be indistinguishable (e.g., a collection of tests ordered by a doctor at one time). An episode is then a sequence of these event sets.

A metric may be constructed on episodes to allow quantitative attribution of a degree of difference (or equivalently, similarity) between at least two episodes by (e.g., optimally) pairing their event sets, and then using a metric on pairs of event sets. In some embodiments, a carepath metric (CP) uses both of these steps, and an event set carepath metric (ESCP) utilizes only the latter step.

In step 2004, the event set construction module 202 constructs sequences of event sets. To construct the event sets, the event set construction module 202 may utilize one or more heuristic(s) that specifies which events belong to a set. Here, sets may be constructed that are separated by small amounts of time (See FIG. 4). It will be appreciated that any amount of time may be used (e.g., ranging from 30 seconds up to 2 hours). In some testing, it was found that the resulting metric on events was the least noisy at 5 minutes.

The metric construction module 204 may be configured to learn a metric on the events from the data. In some embodiments, the metric construction module 204 constructs all or some of the available episodes (e.g., sequences of event sets) from the received data. The metric construction module 204 may require categorization and/or filtering on the events.

In step 2006, the categorization module 206 assigns events categories. For example, the categorization module 206 may assign events to higher-level groups (e.g., categories) by a supplied ontology. For example, various lab tests in a hospital may belong to the category LABS. These categories are utilized in the metric construction example described herein.

In some embodiments, the categorization module 206 creates a synthetic event category for any number of categories (e.g., for any number of categories provided by the supplied ontology). As discussed herein, a synthetic category may be, for example, a more generic or broader category that the general category (e.g., the synthetic category may be broader or more abstract than the categories provided as a part of the ontology). It will be appreciated that an event may be assigned two or more categories (e.g., a general and a synthetic category).

For example, the synthetic event category for LABS may be labeled "GENERIC LAB," and be understood to be a placeholder for some as yet unknown lab. Note that the category of a generic event may be defined to be a category for which that generic event was created.

In some embodiments, the metrics on the event-groups depend on having a metric on the events. If a metric on the event-groups is not given, the metric construction module 204 may construct a metric on the event-groups using the data. As discussed herein, events may be grouped in categories. The categories may be used to construct a metric on the events.

In step 2008, the filter module 208 optionally filters events which occur too infrequently to be discriminated. In some embodiments, the filter module 208 utilizes one or more aggregation function(s) and to identify and/or filter (e.g., eliminate infrequent events). In one example, the filter module 208 generates a cumulative distribution using a cumulative distribution function for event frequencies and filter (e.g., "throw out") the 5% tail. In some embodiments, the filter module labels events 0 for the most common event, 1 for the next most common, and so on. The filter module 208 may then filter or (e.g., remove or eliminate) every event beginning with the number such that the total count of events from that number on is <=5% of the total number of events. In various embodiments, the filter module 208 utilizes a filter process that replaces the event with an instance of the synthetic event for that same category. It will be appreciated that this step may noticeably reduce noise in the resulting event metric space.

In step 2010, the metric construction module 204 learns a metric on events using the categories and/or filtered events. In various embodiments, there may be an order of magnitude more types of events than categories (i.e., the dimensionality of the category space is much lower than that of the event space). We use this dimensionality reduction to make a metric on events. We define a "context" from an event set to be the collection of categories present in that set. For example, if a surgeon orders three lab tests and chest-x-ray at one time, this forms a set which looks like:

{ "COMPREHENSIVE METABOLIC PANEL,"
"CBC WITH DIFFERENTIAL,"
"LIPASE, "
"XR CHEST PA AND LATERAL"}

What this does is generate a "context" {LAB, LAB, LAB, XRAY}. The metric construction module 204 may vectorize these contexts by assigning each category a "dimension" in a Euclidean Space. If we suppose that XRAY is given dimension 2 and LAB dimension 4, then the vectorized context above would look like {0, 0, 1, 0, 3, . . . } where all the other entries are 0. We further normalize these contexts so that they have Euclidean norm=1, which means the context becomes {0, 0, 1/sqrt(10), 0, 3/sqrt(10), . . . }.

Now for each event, the metric construction module 204 may take the sum of the contexts of all the event sets to which that event belongs, and for synthetic events the metric construction module 204 may sum all the contexts for any event which has the same category as the synthetic event. After vector normalization, this may give every event (including synthetics) a unit vector in a Euclidean space of moderate dimensionality, and the angle between such vectors is used as the basis for a metric on the events (See FIG. 5 for example).

It will be appreciated that there may be a large number of event sets which are singletons. This lack of "additional information" (i.e., no context) means that the metric may not resolve these actions effectively. In various embodiments, the operation may be changed to add a value (e.g., 0.01) times the context before and/or after the event-set containing an event (including synthetics), assuming such event-sets exist. This small change may have the desired result without perturbing the rest of the metric. And second, because synthetic events were by their very definition indefinite, distance between a generic event and any other event may be defined in terms of the "dispersion" for real events of that category.

The dispersion of a category may be defined in any number of ways. For example, dispersion of a category may be defined to be square-root of the average of the squares of the angle distance between the synthetic vectorization and all the vectorizations of real events. This gives a measure of how "smeared out" the vectorizations for events in a category are, and may be a reasonable measure of the distance between a synthetic and non-synthetic event. For a pair of synthetic events, the distance is the dispersion if they have the same category, else it is the sum of their individual dispersions plus the angle distance between their respective vectorizations. The dispersion for any real event may be defined to be 0.

As an optimization, since there are not a very large number of distinct events, the metric construction module 204 may pre-compute and cache the distance matrix for the event space.

If events are not equipped a priori with an ontology that produces a categorization on the events, the categorization may be inferred from the data using a simple iterative algorithm. For example, the categorization module 206 may produce the full N×N co-occurrence matrix for all events, and use standard clustering algorithms to define clusters in that space (producing M<N clusters). The metric construction module 204 may take those clusters to be the categories described above, and re-learn the event metric in M-dimensional space. The metric construction module 204 may cluster again in this space, producing M'<M clusters, and re-learn the event metric in M'-dimensional space. The metric construction module 204 may iterate until the procedure converges and take the final clustering as the correct categorization.

In step 2012, the distance module 210 computes a distance between event sets G1 and G2. In one example, the distance module 210 computes a distance between event sets G1 and G2 by using a greedy algorithm on the pairs of elements from each group. For example, the distance module 210 may remove exact matches (adding their distances— which will be 0 unless some synthetic events are present), and then the distance module 210 may compute the distances for all (remaining) pairs in the two sets. The distance module 210 may remove pairs greedily (shortest distances first, if both events are still in their respective sets), and then any left-over unmatched pairs are paired with generic events (See FIG. 6). It will be appreciated that this may be a straightforward extension of the typical solution to the pairing problem in dynamic time warping (which may be utilized herein) where a single type of "no match" event exists. However, it will be appreciated that there are any number of other pairings (e.g., using the Hungarian algorithm) which the distance module 210 might apply.

When pairing events A and B two different event-groups, the distance module 210 may consider two cases: the event distance between A and B, and the sum of the distances between A the synthetic version of A and B and the synthetic version of B. The distance module 210 may take the smaller of these two values as the pairing distance for A and B. As part of this process the distance module 210 may sometimes save the explicit match between event groups. In one example, the distance module 210 may incorporate this code in the distance computation under the control of a Boolean flag.

In some embodiments, if "eva" refers to the array of event objects sorted by integer event codes for the "A group" and "evb" identifies the "B group," a zipper algorithm may be utilized to copy the arrays of events into temporary integer stacks "sa" and "sb" containing the indices into "eva" and "evb" respectively (excepting any exact matches). The return value may be incremented by the distance between these exact matches, which are zero unless the matching events are generic. If the explicit match is preserved, pairs which matched exactly may be saved at this point in a separate stack of event pairs.

All pairs of unmatched events may be stored as float/int/int triples f/i/j as a packed 64-bit Java long integer: here the float is the minimum of the event distance between the events eva[sa(i)], evb[sb(j)] and the sum of the event distances between the events eva[sa(i)] and evb[sb(j)] and their generics. Tegular 'long sorting' in Java may be utilized to sort these triples as f is in IEEE 32-bit format and >=0.0f.

The consensus system 1906 may iterate over the sorted triples removing any pair that is encountered when both elements are still present (clearing the respective entries in sa/sb), and incrementing the return value by f. When one of sa/sb is emptied, remaining sb/sa entries may be processed, incrementing the return value by the distance between that entry and its generic. If the pairs for the exact match are saved, the indices may be used to extract the event pair from "eva" and "evb." The cumulative matching value may be returned.

In step 2014, the episode metric assembly module 212 assembles metrics on episodes. As discussed herein, we introduced two metrics on episodes: the Care Path (CP) metric and the ESCP (Event Set Care Path) metric.

In some embodiments, to construct the CP metric, the episode metric assembly module 212 may use a modified version of dynamic time warping (DTW, also known as sequence alignment) to match event-groups in a pair of episodes to define a distance. Here, an event set is a sequence of events (possibly including synthetic events) and a "synthetic" set is an event set composed entirely of synthetic events. If A is an event set, we define synth(A) to be the set formed by replacing every code in A by its generic form: for A={NUR1, CT5, GENERIC_XR}, then synth(A) is {GENERIC_NUR, GENERIC_CT, GENERIC_XR}

Suppose we have a metric d(A,b)>=0 defined on pairs of event sets which also has the property that d(A,*), for * synthetic, is minimized by d(A,synth(A)). Then we can define a metric on pairs of sequences of events even if the sequences are of different lengths. Given two sequences of sets AB . . . and ab . . . of the same length, we can define a "base metric" bd(AB . . . , ab . . . ) as d(A,a)+d(B,b)+ . . . We then extend this to two sequences of possibly different lengths ABC . . . and abc . . . by "editing" the sequences with insertions of "synthetic sets" to get pairs of sequences of the same length, and then taking the minimum value. If we denote any synthetic set by *, then we can define a distance between AB and abc as the min {bd(AB*,abc), bd(A*B*, a*bc), . . . }, over all possible equal length pairs of edits. This is well-defined because any possible pair of edits which have corresponding *'s can be edited to remove those matching synthetic sets (the value of sum of bd( )'s will not increase), and we know that every * can be replaced by the matching synth( ) event in the other sequence. From this we see that we are taking the minimum over a finite set of edits, and these edits can be thought of as pairs sequences of "pairings" of the form A<->x, Y<->*, or *<->z, which we call "diagonal," "horizontal," respectively "vertical" pairings, for reasons that will shortly become clear.

Let @ be a special code that is otherwise unused. There is a natural correspondence between such pairings and paths (going to the right and up) in the grid with nodes labeled by pairs (x,y) where x ranges over {@,A,B,C, . . . } and y ranges over {@,a,b, . . . }. Going, up diagonally corresponds to diagonal pairing, while a vertical edge is a vertical pairing and a horizontal edge is a horizontal pairing. As examples, the matching ABC with abc of A*BC<->ab*c is shown in FIG. 7a; matching ABC with abc by AB*C<->a**b*c is show in FIG. 7b.

Intuitively a path has a "component in the direction of a sequence element being consumed." The paths must begin in the lower left and go up and/or to the right to the upper right corner. Additionally, since we are looking for consensus on episodes, we probably can count on not being interested in paths with "sufficiently many" synthetic sets, so if the sequences are too different in length or too far from the diagonal, we probably can return a "large value" and quit. This suggests matching at the set level might be linear in the number of sets—and at least less than quadratic—as interesting paths would be constrained to be around the diagonal. To find the cost of the optimal path we only need a matrix of the same size as the grid in which all the paths lie. We assign to every grid point the minimum path cost to get to that point.

We can only get to a point (C,b) from (B,a), (C,a), or (B,b)), and there is only one way from each of these points to (C,b), so knowing those 3 values means we can compute the fourth—a perfect situation for dynamic programming (Note, in fact, that we only need the values for the current column and the previous one, which cuts down on the intermediate state required although not on the number of computations). We will denote this minimal cost state by the table MinCost(,)—that is a properly initialized MinCost(M, n) will be cost of the best pairing of the elements A, . . . , M with a, . . . , n, where MinCost(@,b) means pair *,* with a,b, (i.e. bd((*,*),(a,b)), and and so forth. Naturally MinCost(@, @) is 0. Let us now denote the events A,B,C, . . . by g[0],g[1], etc. and a,b,c, . . . by the elements of the array h[ ]. Instead of MinCost( ) we will use a matrix DTW[i][j] defined to be MinCost(g[i−1],h[j−1])—that is, DTW[i][j] is the cost of the best path aligning the first i entries of g with the first j entries of h. (This reserves the index 0 for @.) DTW is M×N where M=g.length+1 and N=h.length+1, and the cost of the best path is DTW[g.length,h.length]. In pseudocode the matching is performed as per DIST( ) below, where synth(set) is the synthetic version of an event set and d(group,otherSet) is the non-negative symmetric distance between event sets:

```
DIST(g: sets [0..N-1], h: sets [0..M-1]) {
    // DTW[x][y] is the cost of the minimal PATH which 'consumes' the first
    // x elements of g and the first y elements of h - that is, the cost of
    // the best path from (0,0) to (x,y) in the plane.
    DTW := double[N+1][M+1]
    // Fill in the values for the bottom row of the grid
    for i := 0 to N-1
        DTW[i+1][0] := d(g[i],synth(g[i])) + DTW[i][0]) // horizontal
    // Fill in the values for the left column of the grid
    for j := 0 to M-1
        DTW[0][j] := d(synth(h[j]), h[j]) + DTW[0][j]) // vertical
    for i := 0 to N-1
        for j := 0 to M-1
            DTW[i+1][j+1] :=
                min(d(g[i], h[j]) + DTW[i][j],         // diagonal
                    d(g[i], synth(g[i])) + DTW[i][j+1], // horizontal
                    d(synth(h[j]), h[j]) + DTW[i+1][j]) // vertical
    return DTW[N, M]
}
DTW[0][j+1] = d(synth(h[j]), h[j]) + DTW[0][j] for all j>=0, because the
only possible path to (0,j) has the first j+1 entries matched with
synthetics. Similarly for DTW[i][0].
```

A version of the event group distance is shown below for some embodiments. The idea is to penalize matchings of event sets whose indices are too far off from one another, so pairs of episodes may be rejected that are "too different."

```
public double eventSetDistance(Episode pA, EventSet a,
            Episode pB, EventSet b) {
    // Bail if the anchorCode's don't match - we can use this to avoid
    // splitting the anchor segments and doing DTW individually on them,
```

```
// but the complexity of that is outweighed by the performance gain
of
// making the 'sides of the grid' smaller.
    if (a.anchorCode != b.anchorCode)
        return HUGE;
// We take 2/3's of the 'average synthetic error' as the scale to make
// the error 'slightly weaker' than the average synthetic
// error.
    double sdError = (a.distanceToSynthetic +
b.distanceToSynthetic)/3.0;
    double indexError = (a.zbIndex − b.zbIndex)/2.0;
    double incr = sdError * indexError * indexError;
// The error is always included since even an exact match between
// groups of widely different 'times' is still undesirable.
    return eventSetPairing(pA, a.events, pB, b.events, null) + incr;
}
```

The method eventSetPairing( ) does an unconditional matching of the pairs of events in the respective anchor sets from Episodes A and B and returns the resulting distance.

Finally, in computing the ESCP metric (used in the for the second step of consensus core computation below), the episode metric assembly module 212 may perform only the unconditional matching of events by anchor value (e.g., for surgical episodes we make positive and negative groups out of the events in each episodes and pair them and return the total error). In some embodiments, the set of episodes may have been reduced once to those which match up well as "time series" of event sets. This step tries to find a subset with substantial overlap in the actual events, to aid in the construction of a consensus.

The consensus module 216 may determine consensus sequences from clusters of episodes. Having learned the CP and ESCP metrics from the data, we now describe a clustering/portioning of episodes in the data source and a process for computing a consensus sequence from the partitions.

In step 2016, subgroups of events sets are constructed. In various embodiments, the autogroup module 214 automatically constructs coherent subgroups using the carepath metric CP. In one example, the autogroup module 214 constructs a graph of the metric space using the 5 nearest neighbors for each point where the additive edge strength between points p and q is 1/(ordinalDistance(p,q)), where the ordinalDistance(p,q) is j if q is the jth nearest neighbor of p. Having constructed the graph, the autogroup module 214 autogroups using 95% as the "clustering cutoff" The autogroup module 214 then generates a partition of the nodes in the graph, and as those nodes are episodes, this partition gives rise to a collection of "related subsets" on which to search for a consensus (See FIGS. 8a-8b). It will be appreciated that any number of nearest neighbors may be utilized (e.g., not only five) and that the clustering cutoff may be any threshold (e.g., any percentage, discrete value, or the like).

As discussed herein, the process of autogrouping is described with regards to FIGS. 14-17.

Having reduced the problem to searching for a consensus carepath on a given subset, the consensus module 216 may find the "core" of the subset, and then the consensus module 216 processes the core to produce a consensus in step 2018. Given a subset of episodes S, the consensus module 216 computes the points x in S such that the sum(y in S) CP(x,y) is smallest: we refer to such points as those of "maximum centrality" in S under CP. Given this most central subset using CP (call this M), the consensus module 216 then finds the most central subset of M using ESCP, and it is this subset the consensus module 216 denotes as the core C of S. We reject any input subset of length less than 40, since 20 is the minimum core size we have found usable, and we prefer sets with at least 100 points. To increase the probability that that these size constraints are satisfied, in the first step the consensus module 216 finds an M whose size is the minimum of 150 and (1/sqrt(2.0)) times the size of S. The size of C is taken to be the minimum of 100 and (1/sqrt(2.0)) times the size of M. These values would be adjusted for different data types (See FIG. 8b).

Having computed the core, the consensus construction may be an optimization problem: we are looking for a candidate sequence of event-sets c such that Q(c, S)=sum(y in C) CP(c,y) is minimized, subject to a "believability" constraint: the events in c cannot be unrealistic. Specifically, in one example, this means that the consensus module 216 may start with an actual episode, and then edits it conservatively, keeping edits such that Q(c,S) improves. The consensus module 216 may use standard optimization techniques (one level backtracking with a greedy algorithm) with two non-standard heuristics described below.

The first non-standard optimization step is when to begin the optimization without inferring the times of individual events by spreading out the times so everything in an event set has precisely the same time, and the event set are kept apart by a fixed delta. After adding or removing events, the consensus module 216 reruns this process. It is only at the end (e.g., once we feel comfortable with the constituent event-groups) that the consensus module 216 adjusts the event times in the consensus by taking the median time of matching events in the episodes in the core set (See FIG. 8c).

In some embodiments, the second non-standard optimization step is a rule in the editing process such that an event cannot be removed if its count would fall below some minimum number, which we take to be the floor of the average of the first and second quartiles for the counts of that event in the core set; this prevents common events from disappearing but does allow us to reduce the number when this improves CP centrality. We also try to add entire groups, but this rarely succeeds as the starting point for consensus tends not to be missing groups—instead groups are missing occasional individual events found in most other event-groups in the core.

In step 2020, a carepath may be created based on the consensus sequence. For example, the prediction module 218 may predict outcomes of novel episodes (i.e., proposed courses of action) using the distance measures discussed herein, and optionally one or more additional distances representing the state of the entity of interest before the episode commences. Each such distance may give rise to a distance matrix between entities. Using a linear combination of one or more such distance matrices, and values of dependent outcome variables, the prediction module 218 constructs a predictor that can predict the values of dependent outcome variables given input of new entity states, episodes, or a combination of both. With such predictions, one may, for example, optimize the entity states, the episodes, or both, with respect to the outcome variable(s) of interest; forecast outcomes based on said inputs; or similar tasks. The predictions may be utilized to construct the carepath associated with improved outcomes.

This application incorporates by reference U.S. Nonprovisional patent application Ser. No. 14/597,156, filed Jan. 14, 2015, entitled "Consensus Sequence Identification."

In various embodiments, the consensus system 1906 may create cohorts based on user defined filter criteria. The user may be a medical professional, system administrator, insurance manager, or the like. The criteria may be used to identify a medical treatment, medical condition, time frames, physicians, facilities, groups of physicians, and/or the like. The consensus system 1906 may utilize the criteria to create a cohort. A cohort is a group of patients that match the filter criteria. In one example, the filter criteria may assist to identify patients that visited a particular hospital system for treatment regarding a specific medical condition. For example, filtering criteria may include primary physician, length of stay, facility identification, hypertensive, diabetic, or the like. Patients may also be filtered by events.

After a cohort has been created you can discover groups of patients who have received similar care called treatment groups. Treatment groups can be analyzed and examined by various attributes such as cost, length of stay, and comorbidity amongst others. After selecting a specific treatment group to analyze, you can examine which events are more prevalent or which events differentiate this treatment group from others. These treatment groups form the basis of automatically created consensus carepaths. In some embodiments, electronic records and information associated with one or more specific treatment groups and/or any number of cohorts may be retrieved in step 2002 of FIG. 20.

The consensus system 1906 may enable the user to explore cohorts by allowing the user to examine events at the patient level or at the common (consensus) carepath level. The consensus system 1906 may generate a treatment group from the information. A treatment group is a group of patients that have similar treatments (e.g., a similar series of events resulting treatment groups). the consensus system 1906 may generate treatment groups based on, but not limited to, order of events, category of event, frequency of the event, and/or the like.

The consensus system 1906 may enable users to view a comparison of cohorts as well as treatment groups. Comparisons can be done against the entire patient population or the rest of the patient population. In various embodiments, the consensus system 106 generates a group comparison results table shown referred to as an "explain table." There are two type of results that are generated for comparisons. Data columns will be in either one or both of the results sets depending on what kind of data is in the column including continuous data and categorical data. Continuous data is so named because the column has continuous variation within some numerical range. Most numbers (with some obvious exceptions) fit into this data type. Categorical data is composed of a fixed number of categories (e.g., state abbreviations or months of the year). Note that integers can fit into both categories.

The definitions for the column headers in the explain table may include:

| | |
|---|---|
| Column Name | The Column Name List contains the name of each column in the current results. See the section above entitled 'Categorical vs Continuous, Criteria for Inclusion' to see which columns should be expected in Continuous vs Categorical results sets. |
| P-Value | The P-Value Statistics column gives the probability for each dataset column of obtaining randomly events or samples equal to or more extreme than the current observed result. Use P-Value Statistics with the KS Statistic to determine the significance of a comparison for a continuous variable across two groups. Smaller P-Value scores are better. |
| KS Score | The Kolmogorov-Smirnov statistics column presents the likelihood that two groups have the same distribution of values for a column. There are two aspects to the KS score that provide important information about your comparison: the absolute value of the score and the sign of the score. The closer a score is to 1 the better it is. Use KS Score Statistics and the P-Value Statistics values together to determine the significance of a comparison for a continuous variable across two groups. If the P-Value is the same the KS Score takes precedence. |
| Distribution | The distribution column presents comparisons on a column-by column basis. A box plot of the distribution is shown for continuous columns. For categorical data the vertical bars represent distributions for a single group or both groups at once. |

In various embodiments, the consensus system 1906 may enable a user to select consensus events and identify event prevalence during a specific period of time. For example, the group prevalence value may be 5/16. This states that 5 out of 16 patients in this treatment group experienced this event (e.g., at about 1-hour Pre-op). When a consensus event is selected, the user interface may show all instances of that event regardless of time. An event hierarchy search may return a number of patients that experienced the event, regardless of the time of the event. In one example, the same cohort may be displayed showing that 10 patients had this particular event, regardless of the time of the event. Events may be sorted into treatment groups. Events in treatment groups may be sorted by time, prevalence in a group, differentiation, and/or direct variable cost (DVC).

Figure 23:
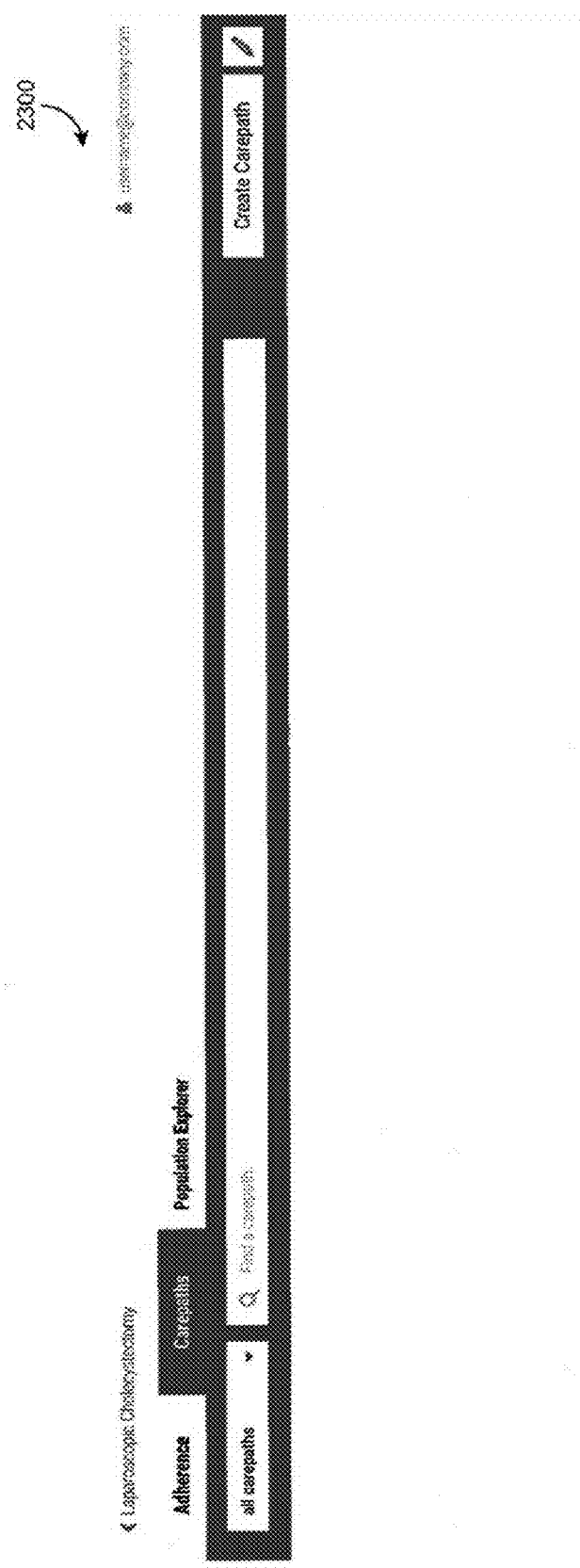
FIG. 23 depicts carepath menu interface to enable a user to create or open a carepath in some embodiments.

In various embodiments, the consensus system 1906 may generate a carepath menu interface to enable a user to create or open a carepath (e.g., a deployed carepath or draft carepath). FIG. 23 depicts carepath menu interface 2300 to enable a user to create or open a carepath in some embodiments. The carepath menu interface 2300 may enable a user to search for deployed or draft carepaths and/or create new carepaths.

Figure 24:
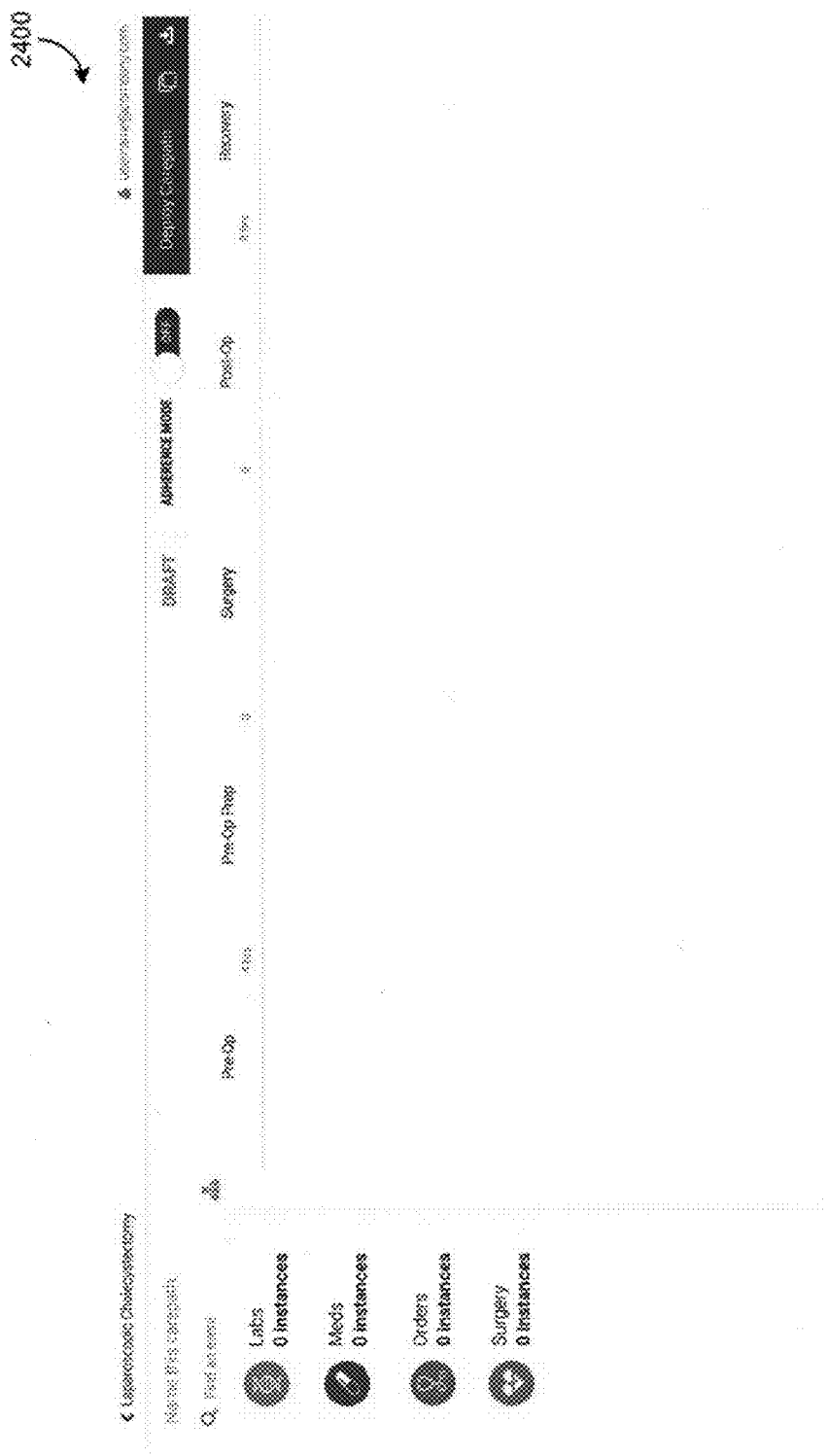
FIG. 24 depicts a carepath interface to search or create carepaths associated with or including laparoscopic cholecystectomy in some embodiments.

FIG. 24 depicts a carepath interface 2400 to search or create carepaths associated with or including laparoscopic cholecystectomy in some embodiments. In some embodiments, adherence mode may be turned off for a managed carepath. A managed carepath is a carepath that is user defined from data. This could be a draft or deployed carepath. Treatment groups may form the basis for the creation of a managed carepath or may be created from a blank carepath.

Adherence mode is a means to visualize and manage adherence events in the managed carepath. By default, adherence mode may be off or inactive for a managed carepath. When adherence mode is OFF, all carepath events are visible. When adherence mode is ON, adherence enabled events are shown, while other events may be automatically shrunk to the left within that column. Events can be enabled for adherence regardless of the adherence mode state.

Figure 25:
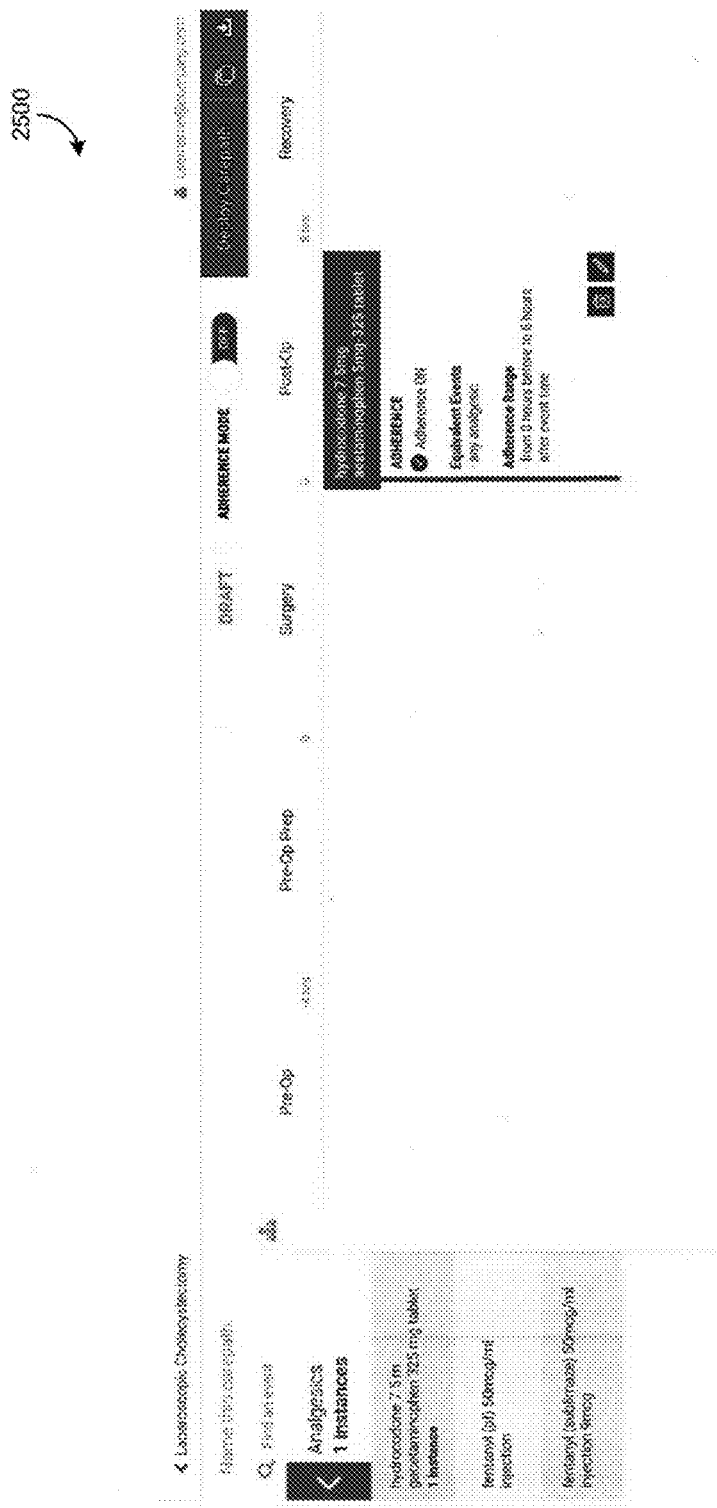
FIG. 25 depicts a carepath interface to create carepath events associated with or including laparoscopic cholecystectomy in some embodiments.

FIG. 25 depicts a carepath interface 2500 to create carepath events associated with or including laparoscopic cholecystectomy in some embodiments. In various embodiments, a user may utilize carepath interface 2400 of FIG. 24 and create new entry during an epoch or time frame. In this example, the user has created an event for treatment including hydrocodone 7.5 mg acetaminophen 5 mg-325 tablet. The user has made the event an adherence object by activating the adherence switch, added a time frame (e.g., a time frame predicate) from 0-eight hours after "event time" (e.g., surgery), and identified equivalent events (e.g., defining an object predicate) including "any analgesics." Predicates, equivalent events, and adherence ranges are further discussed herein.

Figure 26:
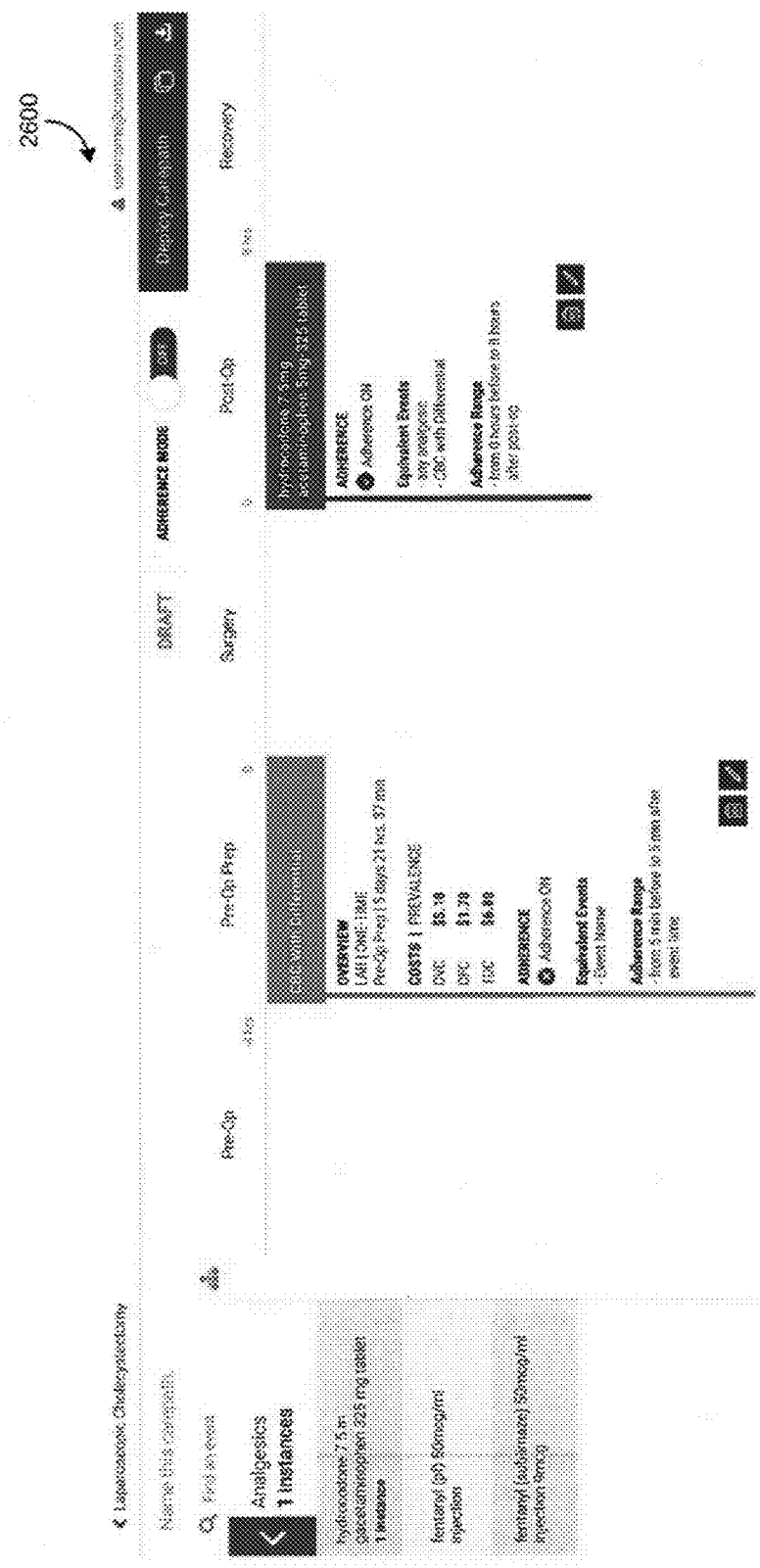
FIG. 26 depicts a carepath interface to create carepath events associated with or including laparoscopic cholecystectomy in some embodiments.

FIG. 26 depicts a carepath interface 2600 to create carepath events associated with or including laparoscopic cholecystectomy in some embodiments. In various embodiments, a user may utilize carepath interface 2500 of FIG. 25 and create another new entry during an epoch or time frame. In this example, the user has created an event for treatment including CBC with Differential. The representation of the event may include costs (e.g., DVC, DFC, and TDC), an indication of whether the event is an adherence object, if there are equivalent events, and an adherence range.

Figure 27:
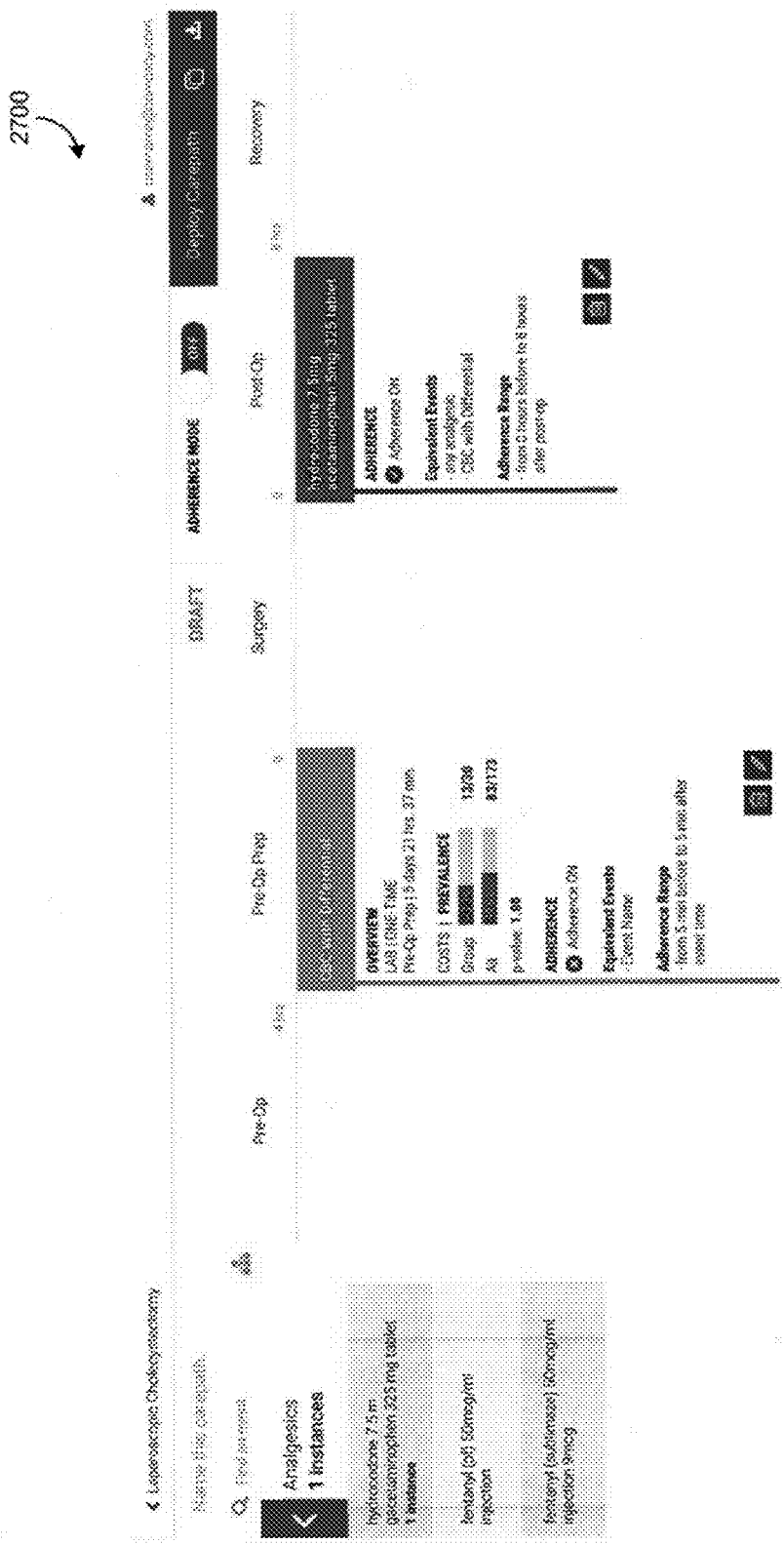
FIG. 27 depicts a carepath interface to create carepath events associated with or including laparoscopic cholecystectomy in some embodiments.

FIG. 27 depicts a carepath interface 2700 to create carepath events associated with or including laparoscopic cholecystectomy in some embodiments. In various embodiments, a user may utilize carepath interface 2600 of FIG. 26 to receive more information regarding the event for treatment including CBC with Differential. The representation of the event may include (e.g., when clicked or on engaged by a user) a bar graph of costs based on prevalence and p-values.

Event prevalence represents the number of patients experiencing this particular event at this time. When a consensus event is selected, all instances of that particular event are highlighted. For example, the group prevalence value may be 5/16. In this example, 5 out of 16 patients in this treatment group may have experienced this event (e.g., at about 1-hour Pre-op).

Per event prevalence statistics may represent how many patients experienced this event in a treatment group ("Group") and how many patients experienced this in the entire patient population ("All"). The count and percentage of the population is shown. For example, the sample below shows that pregabalin occurs in 30 of 31 patients in this group, and in 215 or 1314 patients in the entire cohort at this time. It is important to remember that prevalence in "Group" and "All" is time sensitive.

Per event differentiation (p-value) statistic may be a measure of how much more common an event is in this treatment group as compared to all patients for this procedure. More formally, it represents the probability that the difference in event prevalence between this treatment group and all patients is due to random chance. A low p-value paired with a high group prevalence score suggests that an event is part of the differentiating characteristics of the treatment for this treatment group.

Sorting of events in a treatment group: events in a treatment group can be sorted by time, prevalence (Group), differentiation, and direct variable cost (DVC)

Carepaths View The carepaths view allows you to modify and refine your draft carepath or view your deployed carepaths. To allow for easier modeling and refinement of carepaths, the carepath is displayed in a calendar style view with each column representing a different period of time.

The left hand side of the user interface allows you view all events in the carepath by navigating the hierarchy of Labs, Orders, Meds and Surgery. To search for new events not already in the carepath, the user can simply type in the name of the event in the search box. This will search all events in the data to find a match.

PDFs of managed carepaths may be created via drop down option in the managed carepath. The PDF document generates a single page for each column of the managed carepath. When annotations/notes are created, they are added to the first page of the PDF document. Similarly, you can also download the carepath as a CSV file.

Event cards will include statistics from the treatment group from which it was derived. When new events are added (e.g., not derived from the treatment group).

Figure 21:
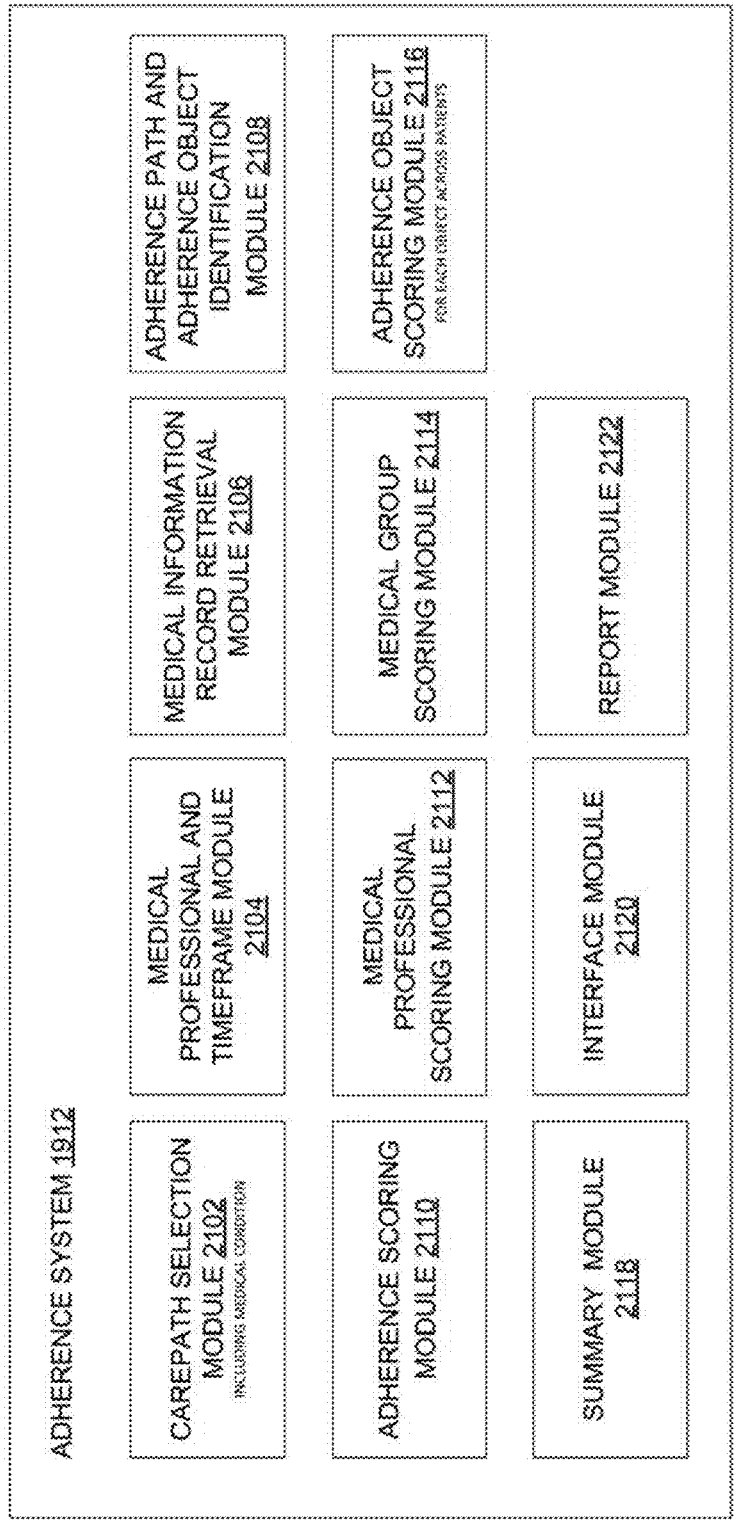
FIG. 21 depicts a block diagram of an adherence system in some embodiments.

FIG. 21 depicts a block diagram of an adherence system 1912 in some embodiments.

The adherence system 1912 includes a carepath selection module 2102, a medical professional and time frame module 2104, adherence path and adherence object identification module 2108, adherence scoring module 2110, medical professional scoring module 2112, medical group scoring module 2114, adherence object scoring module 2116, summary module 2118, interface module 2120, and report module 2122. It will be appreciated that there may be any number of modules performing any number of functions.

The adherence system 1912 may create an adherence path of a carepath. An adherence path is a set of objects (i.e., adherence objects) which constitute a subset of events of a carepath (e.g., labs, orders, tests, visits, surgical procedures, post op procedures, pre op procedures, costs, hospital stays, diagnosis, conditions, medications, and/or the like). Each adherence object may correspond to an event or a set of events that may be seen as differentiators that may significantly impact medical treatment. While all aspects of the carepath may be recommended, only a subset of those events may be critical to care or considered to be impactful to the outcome of treatment.

Regarding adherence path creation, the adherence system 1912 may identify or receive selections of events of a carepath that are differentiators regarding outcomes and identify those events as being adherence objects of an adherence path of the carepath. In various embodiments, each adherence object may have a predicate. A predicate includes rules to be satisfied. In various embodiments, the predicate may include an object predicate and a time frame predicate. It will be appreciated that there may be any number of rules that are a part of the predicate and not just limited to rules of object and time frame. The object predicate may correspond to a code or a set of codes referring to a certain procedure or event has occurred. It will be appreciated that a medical system (e.g., hospital system or insurance system) utilize any number of codes to refer to events (e.g., labs, orders, tests, visits, surgical procedures, post op procedures, pre op procedures, costs, hospital stays, diagnosis, conditions, medications, and/or the like). The object predicate may refer to one or more of the codes.

The time frame predicate refers to a time when the object predicate is to be performed. For example, a time frame predicate may indicate whether a specific procedure (corresponding to a predicate object) must be performed before a certain time (e.g., before surgery), after a certain time (e.g., after surgery), or at a certain duration (e.g., within 10 days after an initial visit for a specific medical condition).

In one example, a patient may visit a hospital for treatment of pneumonia. The pneumonia carepath may have one hundred different events that are expected to occur for best treatment (e.g., the best protocol). Of those one hundred events, perhaps only twenty are considered to be most dispositive to successful treatment of the medical condition. Those twenty events may be defined to be a part of the adherence path. Each event may be an adherence object of the adherence path. As such, each adherence object may have a different object predicate and a different time frame predicate. The object predicate may indicate a code or a set of equivalent codes (corresponding to events tracked by the EMR). The time frame predicate may refer to a specific time frame for the specific event corresponding to the code of the object predicate.

It will be appreciated that a predicate may have any number of rules. For example, beyond an object predicate and a time frame predicate, a predicate may include rules of specific events that have to happen together, equivalent events (e.g., any of the equivalent events may satisfy that rule of the predicate), a sequence of events that must occur in a specific sequence, conditions (e.g., cost and/or number of hospital stays), and/or the like.

The adherence system 1912 may also measure adherence (compliance) of an entity to the adherence path. The entity may be a medical professional (e.g., physician), group of medical professionals, facility (e.g., a group of medical professionals associated with a facility such as a specific hospital or clinic), or system (e.g., hospital system or insurance system). For each patient associated with a medical condition of a carepath, the adherence system 1912 may score each adherence objects of that carepath. In some embodiments, the score for that adherence object may indicate if that particular adherence object (including all rules of a predicate of that adherence object) was satisfied. In one example, the adherence system 1912 may score a 0 (not satisfied) or a "1" (satisfied) for each adherence object of that particular patients adherence path.

The adherence system 1912 may utilize the individual adherence object scores of the adherence path for each patient to generate a patient adherence path score indicating whether a one or more medical professionals complied with the adherence path of the carepath for that particular patient. In one example, the adherence system 1912 may total the number of adherence objects that were satisfied and generate a decimal score in comparison with the total number of adherence objects (e.g., if 10 adherence objects were satisfied out of 20, the patient adherence path score may be 0.5).

The adherence system 1912 may utilize each patient adherence path score of a group of patient adherence path scores to generate a medical professional adherence score, a medical group adherence score, a facility adherence score, and/or a system adherence score. For example, the adherence system 1912 may determine the individual patient adherence path scores of a set of patients of a particular medical professional that share a similar medical condition over a particular period of time. The adherence system may determine a medical professional adherence score based on the individual patient adherence path scores which may indicate the degree to which the medical professional complied with the adherence path of the carepath. For example, the adherence system 1912 may determine the average (e.g., mean, median, and/or mode) of the group of individual patient adherence path scores to generate the medical professional adherence score. In another example, the adherence system may determine the medical professional adherence score based on the individual patient adherence object scores (without generating the patient adherence path scores).

It will be appreciated that the medical professional adherence score may indicate, in some embodiments, whether the medical professional is in compliance with one adherence path or a set of adherence paths of different carepaths. For example, the medical professional may treat patients with any number of different medical conditions associated with different carepaths. The adherence system 1912 may generate an individual patient adherence score associated with each patient relative to the specific adherence path of their particular carepath. The adherence system 1912 may generate an patient group adherence path score for each adherence path and then may generate the medical professional adherence score based on the patient group adherence path score. For example, for each adherence path, the adherence system 1912 may determine the average (e.g., mean, median, and/or mode) of the group of individual patient adherence path scores to generate a patient group adherence path. The adherence system 1912 may determine the average (e.g., mean, median, and/or mode) of the group of patient group adherence path scores to generate a medical professional adherence score. Alternately, the adherence system 1912 may generate individual patient adherence scores relative to each patient in their specific adherence path and then average all of the individual patient adherence scores across all of the adherence paths to generate the medical professional adherence score.

Similarly, the adherence system 1912 may generate a medical group adherence score. In various embodiments, the adherence system may generate the medical group adherence score by averaging the individual medical professional adherence scores of medical professionals of the group. In some embodiments, the adherence system 1912 may generate the medical group adherence score by averaging individual patient adherence scores of each patient of each medical professional associated with one or more carepaths.

The adherence system 1912 may generate a facility adherence score in a similar manner. For example, the adherence system may generate the facility adherence score by averaging the individual medical professional adherence scores of medical professionals of the facility. In some embodiments, the adherence system 1912 may generate the facility adherence score by averaging individual patient adherence scores of each patient of each medical professional associated with the facility associated with one or more carepaths.

The adherence system 1912 may generate a system adherence score in a similar manner. For example, the adherence system may generate the system adherence score by averaging the individual medical professional adherence scores of medical professionals of the system or averaging the facility adherence scores. In some embodiments, the adherence system 1912 may generate the system adherence score by averaging individual patient adherence object scores of each patient (or individual patient adherence path scores) of each medical professional of the system associated with one or more carepaths.

The adherence system 1912 may generate reports and/or interfaces to display any of the scores, summarize information, assist in identifying carepaths with high or low adherence, identify specific adherence objects with high or low scores, and provide drill down interactions to enable a user to view specific patient information (e.g., from the EMR) related to events associated with adherence objects with any (e.g., high or low) adherence score.

It will be appreciated that the interface and/or reports may enable users to investigate outcomes of patients related to treatments that did not adhere to one or more adherence objects of an adherence path. As a result, the carepath and/or adherence path may be updated if the outcome of the patients with treatments that did not adhere to one or more adherence objects of an adherence path was the same as other patients that did adhere to the same one or more adherence objects or was better than other patients that did adhere to the same one or more adherence objects. For example, those adherence objects that do not appear to make a difference to outcome may be dropped from the adherence path and/or removed from the carepath.

Further, it will be appreciated that if outcomes of patients with treatments that did adhere to one or more adherence objects of an adherence path was better than other patients with treatments that did not adhere to the same adherence objects, then there may be confirmation that those particular adherence objects are differentiators (e.g., important or critical to outcome).

The carepath selection module 2102 may be used to select a carepath and/or an adherence path. In some embodiments, a user (e.g., administrator) may wish to create an adherence path for a particular carepath. The user may log into the adherence system 1912 and/or the carepath system 1906. The adherence system 1912 and/or the carepath system 1906 may authenticate the user (e.g., using the user's password and/or any other data rights) to confirm or provide rights to any number of carepaths and/or adherence paths.

In various embodiments, the carepath selection module 2102 may provide a list of available carepaths to the user. The carepaths may be drafted carepaths. In some embodiments, the carepaths being provided may be deployed carepaths or a combination of deployed and/or drafted carepaths.

The carepath selection module 2102 may receive a carepath selection from the user and the carepath selection module 2102. The carepath selection module 2102 may select a carepath from any number of carepath to provide to the user. In some embodiments, the interface module 2120 may be configured to generate an interface to enable the user to view the carepath and create (or edit) an adherence path of the carepath.

Figure 28:
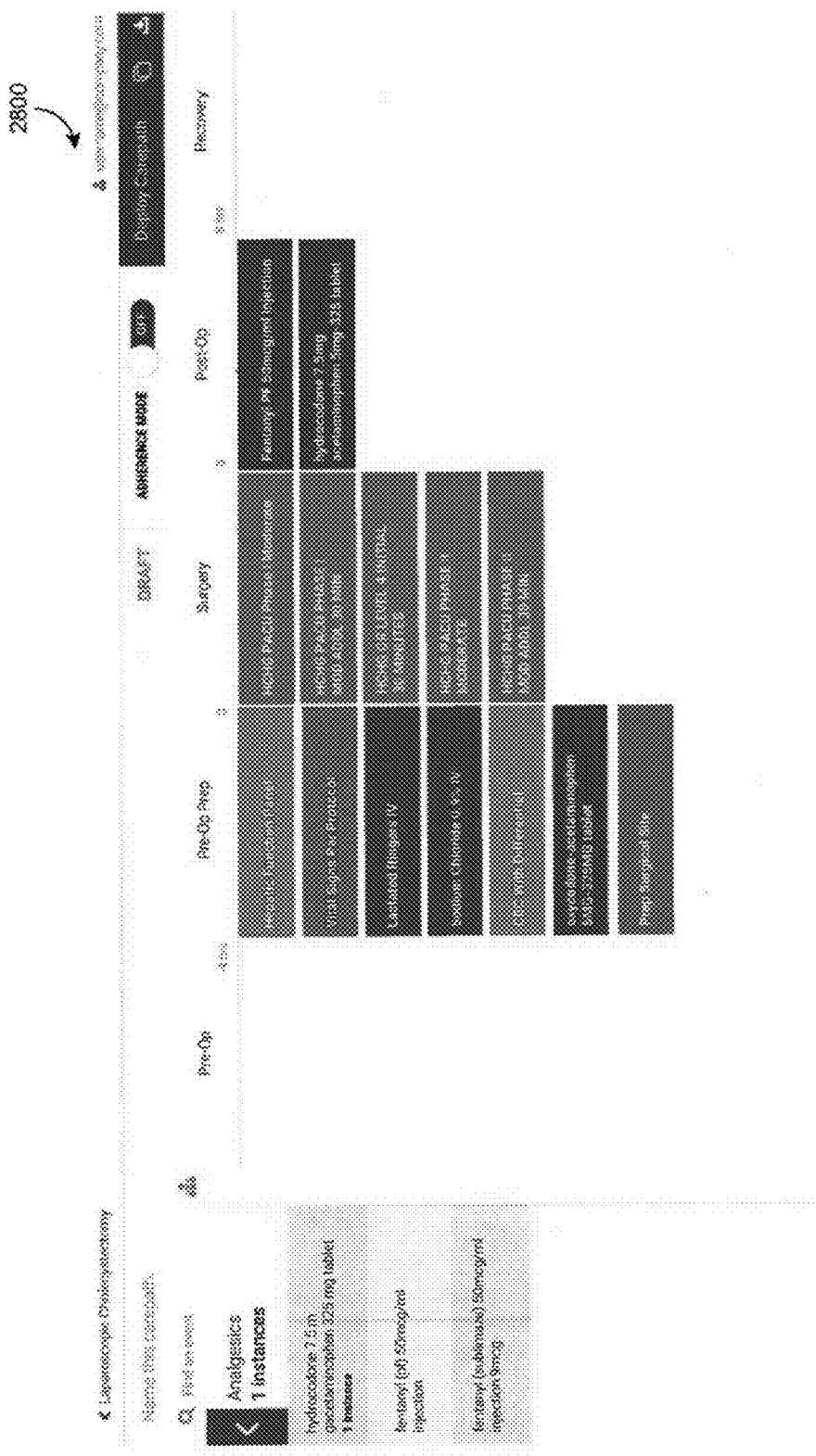
FIG. 28 depicts a carepath interface in some embodiments.

FIG. 28 depicts a carepath interface 2800 in some embodiments. The carepath interface 2800 is with regard to laparoscopic cholecystectomy. The carepath interface 2800 is divided into time portions including pre-op (four hours before surgery), surgery, post-op (up to 8 hours after surgery, and recovery. The pre-op timeline recommends seven events as a part of the carepath (e.g., preferred treatment) including hepatic function panel, vital signs per protocol, lactated ringers IV, sodium chloride 0.9% IV, CBC with differential, oxycodone-acetaminophen 5MG-325 tablet, and prep surgical site. The surgery timeline recommends five events as a part of the protocol including HCHG PACU phase I moderate, HCHG PACU phase I mod addl 30 minutes, HCHG or level 4 initial 30 minutes, HCHG PACU phase II moderate, and HCHG PACU phase II mod addl 30 min. The post-op timeline recommends two events as a part of the protocol including fentanyl PF 50 mcg/ml injection and hydrocodone 7.5 mg acetaminophen 5 mg-325 tablet.

The carepath interface 2800 may enable the user to add additional events to the carepath (e.g., through the consensus system 1906 and/or the adherence system 1912). The carepath interface 2800 indicates that the adherence mode is off meaning that the adherence path is not denoted in the carepath interface 2800.

Figure 29:
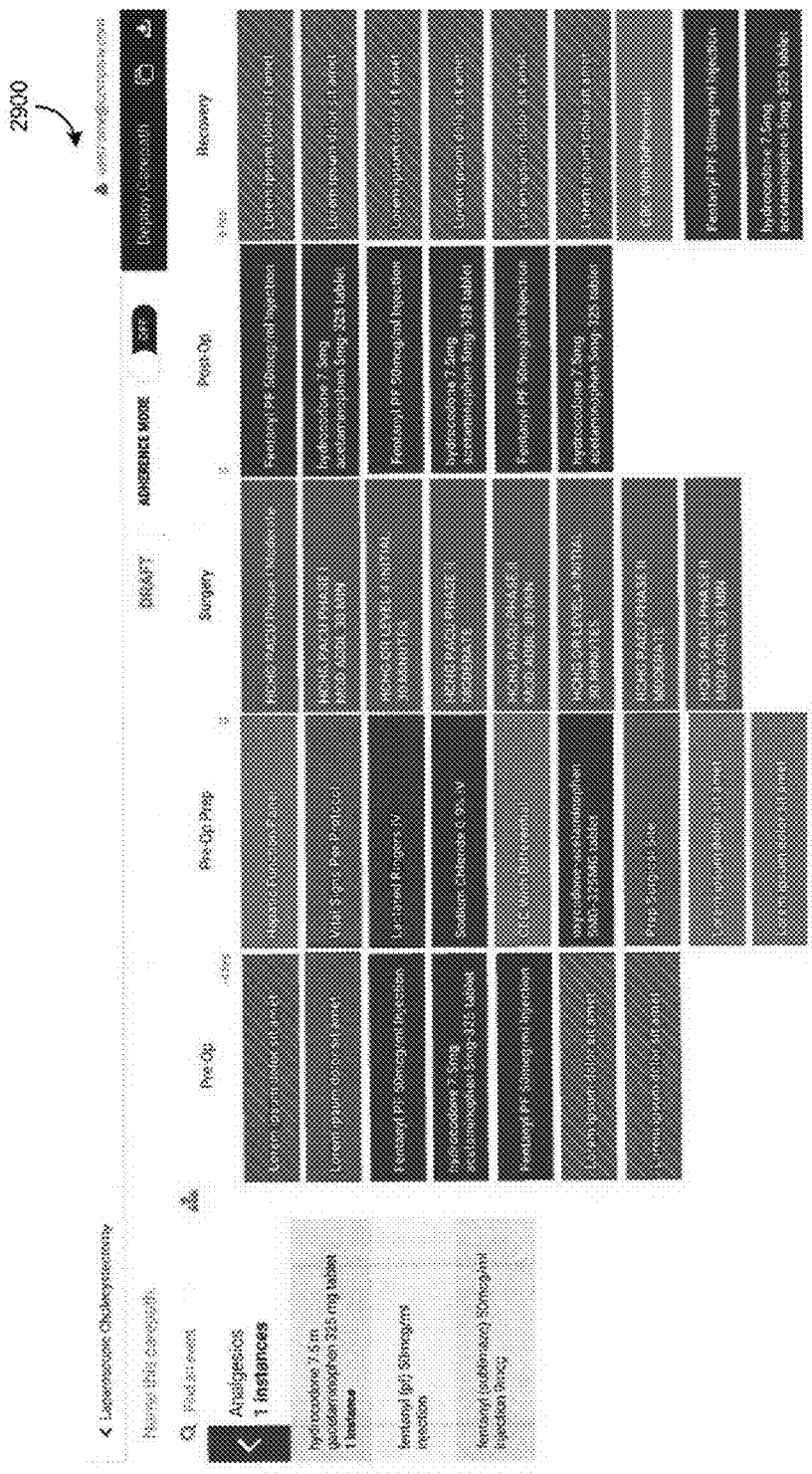
FIG. 29 depicts a carepath interface in some embodiments.

FIG. 29 depicts a carepath interface 2900 in some embodiments. The carepath interface 2900 may be the carepath interface 2800 and may depict the same carepath but with additional events added to the carepath. For example, there are seven events in the pre-op time frame (more than four hours before surgery), nine events in the pre-op prep time frame (between 0 to 4 hours before surgery), eight events in the surgery time frame, six events in the post-op time frame (up to eight hours after surgery), and nine events in the recovery time frame (eight hours or more after surgery). Although some of the events are labeled "Lorem ipsum dolor sit amet," it will be appreciated that these can be any event and are depicted in FIG. 29 as examples.

The carepath interface 2900 may enable the user to add further additional events to the carepath (e.g., through the consensus system 1906 and/or the adherence system 1912). Like carepath interface 2800, carepath interface 2900 indicates that the adherence mode is off meaning that the adherence path is not denoted in the carepath interface 2900.

In various embodiments, the adherence system 1912 may enable a user to create an adherence path using the carepath related to a specific medical condition as well as patient information from past treatments. The carepath may identify all events that are a part of the "best practices" protocol. Patient information related to the selected carepath may enable the user to identify those events of the carepath that appear to be most related to effective care and outcomes. It will also be appreciated that the user may base selection of specific events in the carepath for the adherence path based on past medical records, input from experts, medical research, and/or the like.

The medical professional and time frame module 2104 may provide an interface and or receive a selection of an entity such as a medical professional (e.g., physician), group of medical professionals, facility (e.g., a group of medical professionals associated with a facility such as a specific hospital or clinic), or system (e.g., hospital system or insurance system). The medical professional and time frame module 2104 may also receive a selection of a time frame such as a duration of time (e.g., over the last 16 months).

The medical information record retrieval module 2106 may retrieve any number of patient medical records or relevant information from the patient medical records based on the medical condition of the selected carepath and patients of the identified entity (patients of a doctor, patients of a group of doctors, patients of a facility, or patients of a system) who received treatment related to the medical condition during the identified time frame. The retrieved medical information from the patient medical records may include any number of outcomes (e.g., complications, recovery, different symptoms, further treatment, and/or the like).

The adherence path and adherence object identification module 2108 may provide medical information from the retrieved medical information (e.g., from the patient medical records retrieved by the medical information record retrieval module 2106) to enable the user to identify events that appear relevant to outcome and treatment to add to an adherence path (or create an adherence path).

In various embodiments, the adherence path and adherence object identification module 2108 may modify adherence objects of an adherence path. In one example, the adherence path and adherence object identification module 2108 may add rules to the predicate (e.g., add rules to the object predicate and/or time frame predicate). For example, the adherence path and adherence object identification module 2108 may add equivalents.

In some embodiments, the only assumption is that the consensus construction includes a selection process of the most representative events in each encounter in a set called the "core" (encounters which may be deemed sufficiently consistent that we believe a consensus can be found from them). In one example, if the core is $S=\{enc_1, \ldots, enc_k\}$, then each event of the consensus carepath of S takes place in a sufficient number of encounters $enc_i$ around the same time.

In some embodiments:
1) For each category of events, an array of non-overlapping time intervals $\{[t_{00},t_{01}], [t_{10},t_{11}], \ldots\}$ is created so that each interval contains an approximately equal number of events across all encounters $enc_i$.
2) In each interval for each category, a number of events are assigned to the carepath based on the following conditions: a) events may be present in a sufficient number of encounters in that time interval; b) if more than one event is put into the carepath, each of the possible pairs of those events may be present in a sufficient number of encounters; c) the maximum number of events that can be put into the carepath for a time interval is the median number of events in that category in that time interval across the set S.
3) For each event e in carepath, we store the time range [t0,t1] of all events in the same category and time interval used in the carepath construction. A list of all other events present in that interval for that category that can be alternative choices to the event in carepath may be stored. In some embodiments, the equivalency rule may be that alternative events should happen in a sufficient number of encounters in that time interval, but not be present at the same time as the event e in carepath.
4) For each event e, a predicate may be created with time range corresponding to the time range stored for that event, and matching event codes corresponding to the set of alternative events.

Figure 30:
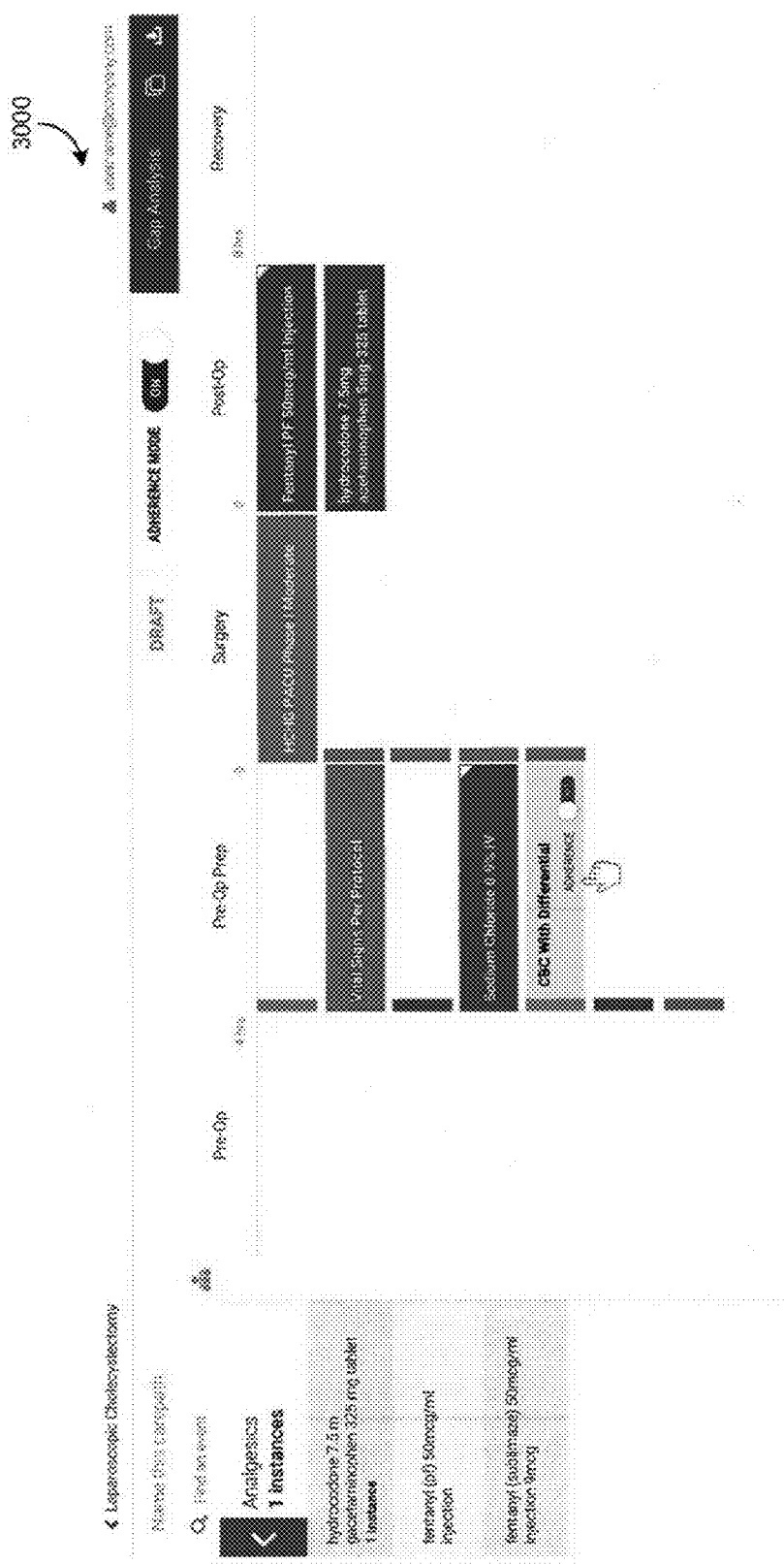
FIG. 30 depicts a carepath interface in some embodiments.

FIG. 30 depicts a carepath interface 3000 in some embodiments. In FIG. 30, the carepath interface depicts the carepath of FIGS. 28 and 29, but with adherence mode activated. With adherence mode "on," those events of the carepath that are not associated with the adherence path are minimized (e.g., denoted as vertical bars that may maintain the context and type of non-adherence objects) while those events that are associated (or are a part of) the adherence path are identified a full bars with titles. In some embodiments, on hover of a mouse over a collapsed event, the event representation may expand and provide an option to turn adherence on.

For example, adherence objects that are to occur in pre-op prep include vital signs per protocol, sodium chloride 0.9% IV, and CBC with differential (which appears to be recently added). In this example, the event CBS with differential may have, at one time, been a part of the carepath but not a part of the adherence path. The user may toggle an adherence switch to select the event to be a part of the adherence path thereby making CBC with differential an adherence object.

Other adherence objects in carepath interface 3000 include HCHG PACU phase I moderate during surgery as well as fentanyl PF 50 mcg/ml injection and hydrocodone 7.5 mg acetaminophen 5 mg-325 tablet during post-op.

It will be appreciated that adherence mode enables a user or doctor to identify adherence objects (e.g., those events that are most critical to outcome) more easily which will enable the doctor to get more information regarding the most critical components of the protocol.

In various embodiments, the adherence path and adherence object identification module 2108 enables a user to define additional rules to further define the predicate. For example, the adherence path and adherence object identification module 2108 may enable the user to define equivalent events (e.g., object predicates) that satisfy the adherence objective. In some embodiments, the adherence path and adherence object identification module 2108 enables the user to define or change a time predicate related to the adherence object and/or its equivalents.

Figure 31:
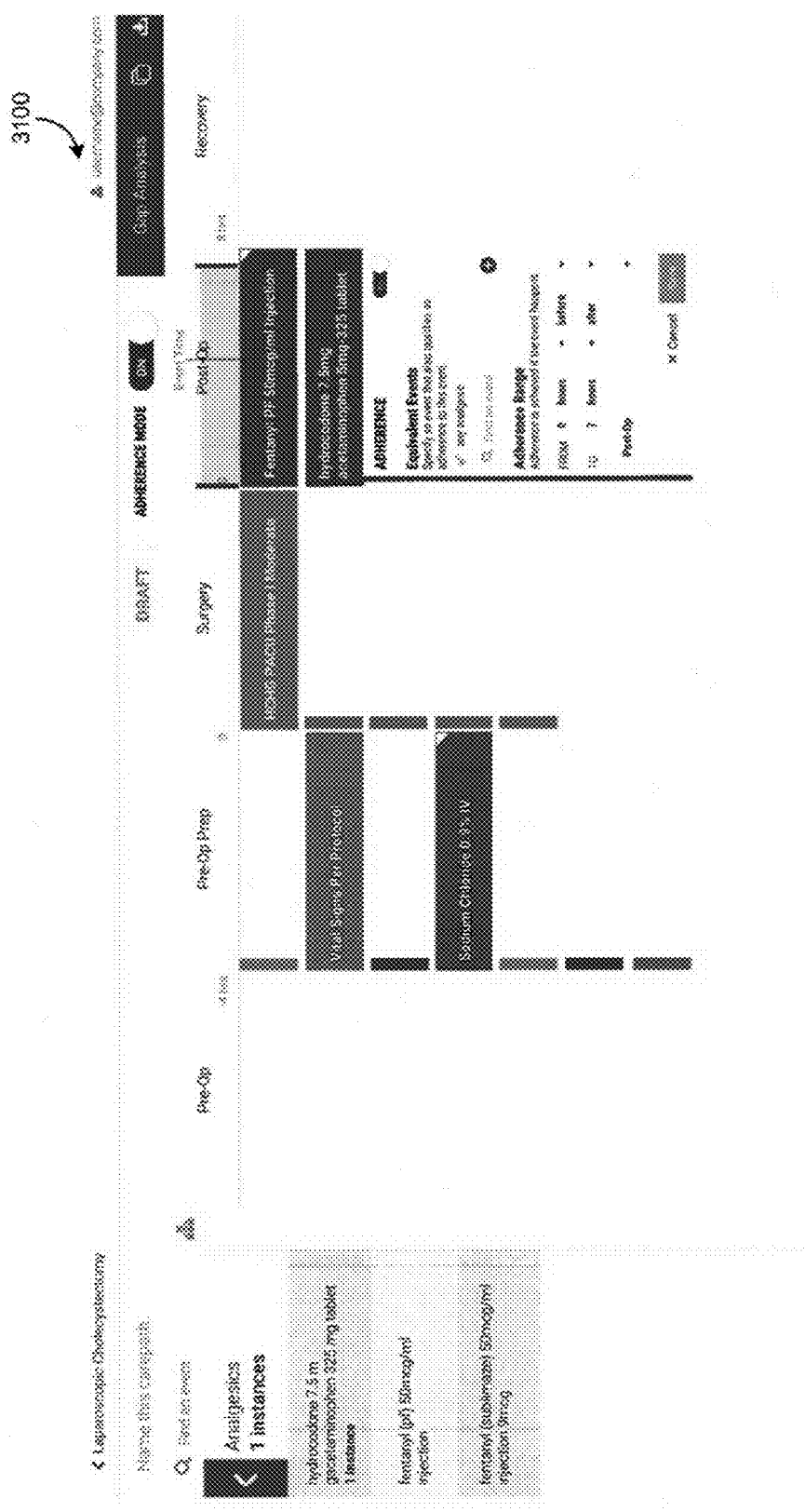
FIG. 31 depicts a carepath interface in some embodiments.

FIG. 31 depicts a carepath interface 3100 in some embodiments. In FIG. 31, the carepath interface depicts the carepath of FIGS. 28-30 with adherence mode activated. In FIG. 31, a user has selected hydrocodone 7.5 mg acetaminophen 5 mg-325 tablet during post-op which has revealed options in the carepath interface 3100. The depiction of the adherence object has expanded to enable a user to add equivalent events and change the time predicate for the hydrocodone 7.5 mg acetaminophen 5 mg-325 tablet event. In this example, the user has added "any analgesics" as an equivalent to hydrocodone 7.5 mg acetaminophen 5 mg-325 tablet. In determining if the object predicate is satisfied for adherence scoring, the adherence system 1912 may determine if hydrocodone 7.5 mg acetaminophen 5 mg-325 tablet during post-op or any analgesic (e.g., a code indicating hydrocodone 7.5 mg acetaminophen 5 mg-325 tablet or any code indicating an analgesic) was provided.

Further, in this example, the user is able to change the time frame predicate. For example, the hydrocodone 7.5 mg acetaminophen 5 mg-325 tablet event representation includes an ability to change the "adherence range." The adherence range lists, in the carepath interface 3100, a range "from 0 hours before [a time reference such as surgery]" to "seven hours after" a time reference such as post-op. In this example, the adherence system 1912 may determine if hydrocodone 7.5 mg acetaminophen 5 mg-325 tablet or any analgesic is provided up to seven hours after surgery, then the object predicate and the time frame predicates are satisfied and, as a result, the adherence object is satisfied for that particular patient treatment. In various embodiments, a user may grab and slide an adherence range slider to define the time frame predicate.

It will be appreciated that any equivalents (e.g., either specific equivalents or a category of equivalents such as "any analgesics") may be added to an adherence object. Similarly, any time frame associated with an adherence object may be added or changed.

Figure 32:
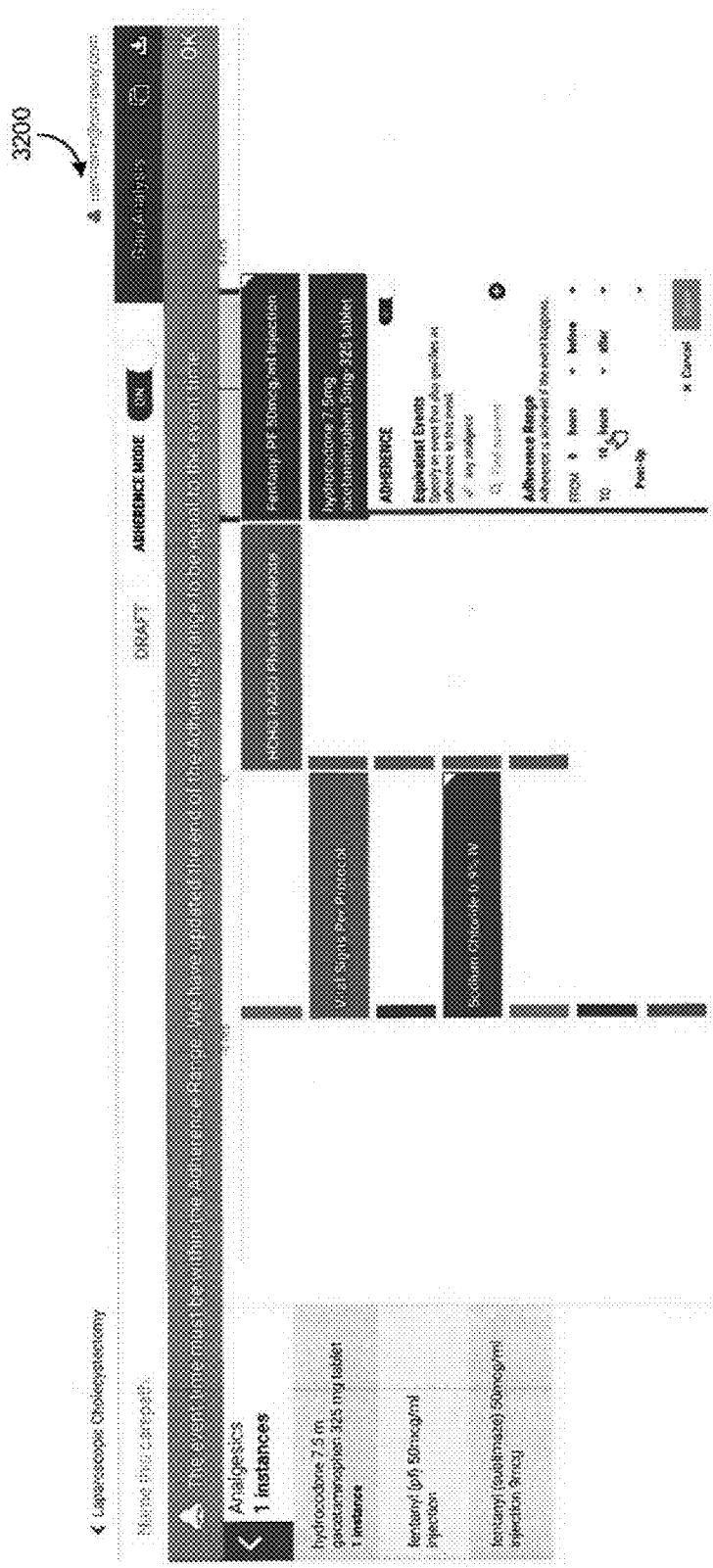
FIG. 32 depicts a carepath interface in some embodiments.

FIG. 32 depicts a carepath interface 3200 in some embodiments. In FIG. 32, the carepath interface depicts the carepath of FIGS. 28-31 with adherence mode activated. In FIG. 32, a user has selected hydrocodone 7.5 mg acetaminophen 5 mg-325 tablet during post-op which has revealed options in the carepath interface 3200. In this example, the user has updated the time frame predicate "to seven hours after" to "ten hours after."

Figure 33:
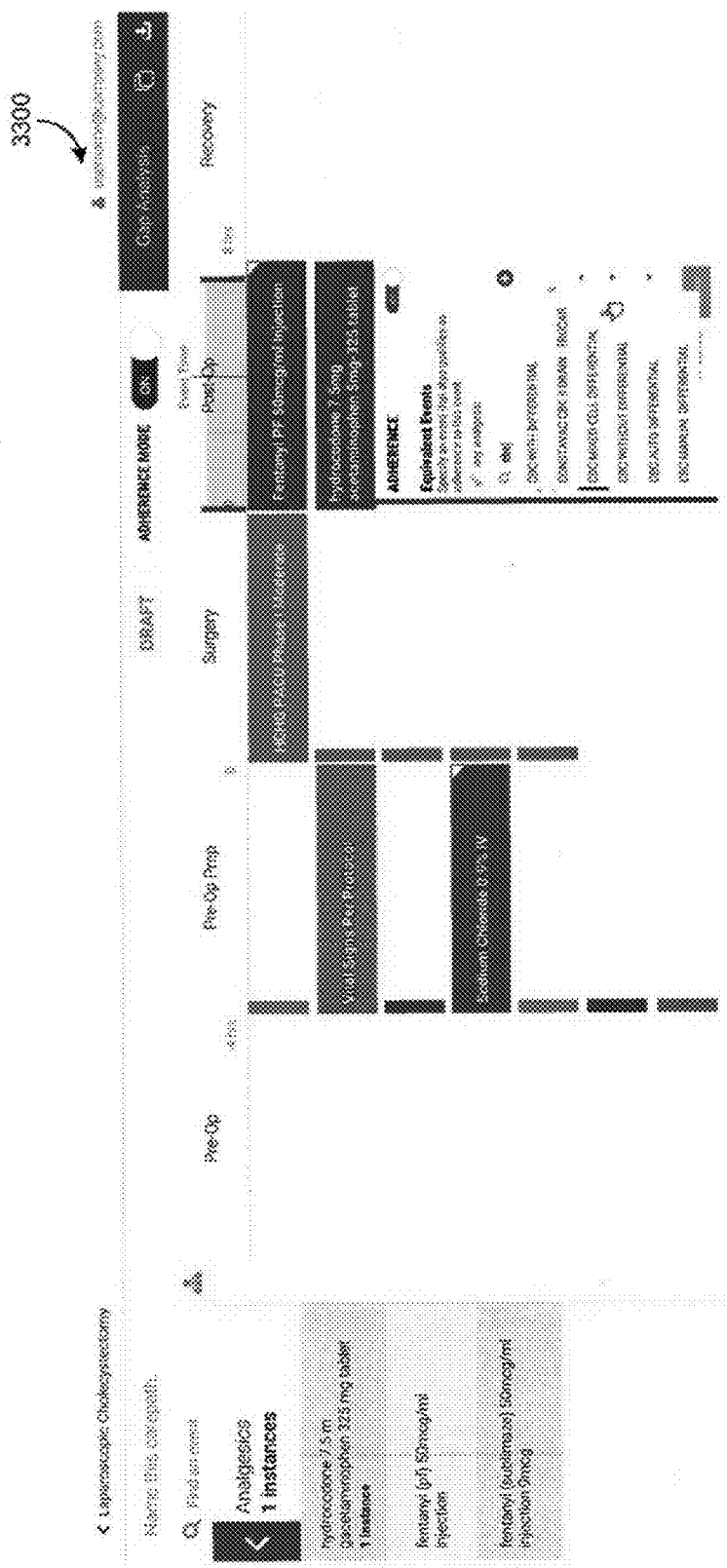
FIG. 33 depicts a carepath interface in some embodiments.

FIG. 33 depicts a carepath interface 3300 in some embodiments. In FIG. 33, the carepath interface depicts the carepath of FIGS. 28-32 with adherence mode activated. In FIG. 33, a user has selected hydrocodone 7.5 mg acetaminophen 5 mg-325 tablet during post-op which has revealed options in the carepath interface 3300. In this example, the representation of the event for hydrocodone 7.5 mg acetaminophen 5 mg-325 tablet during post-op has expanded to include a search function to assist the user to identify events that may be added as equivalents (e.g., to further define the object predicate). In this example, the user entered "cbc" and, as a result, has been offered a list including CBC with differential, constavac CBC II drain—trocar, CBC mixed cell differential, CBC without differential, CBC auto differential, and CBC manual differential. The user may select any of these entries or any combination as equivalents.

Figure 34:
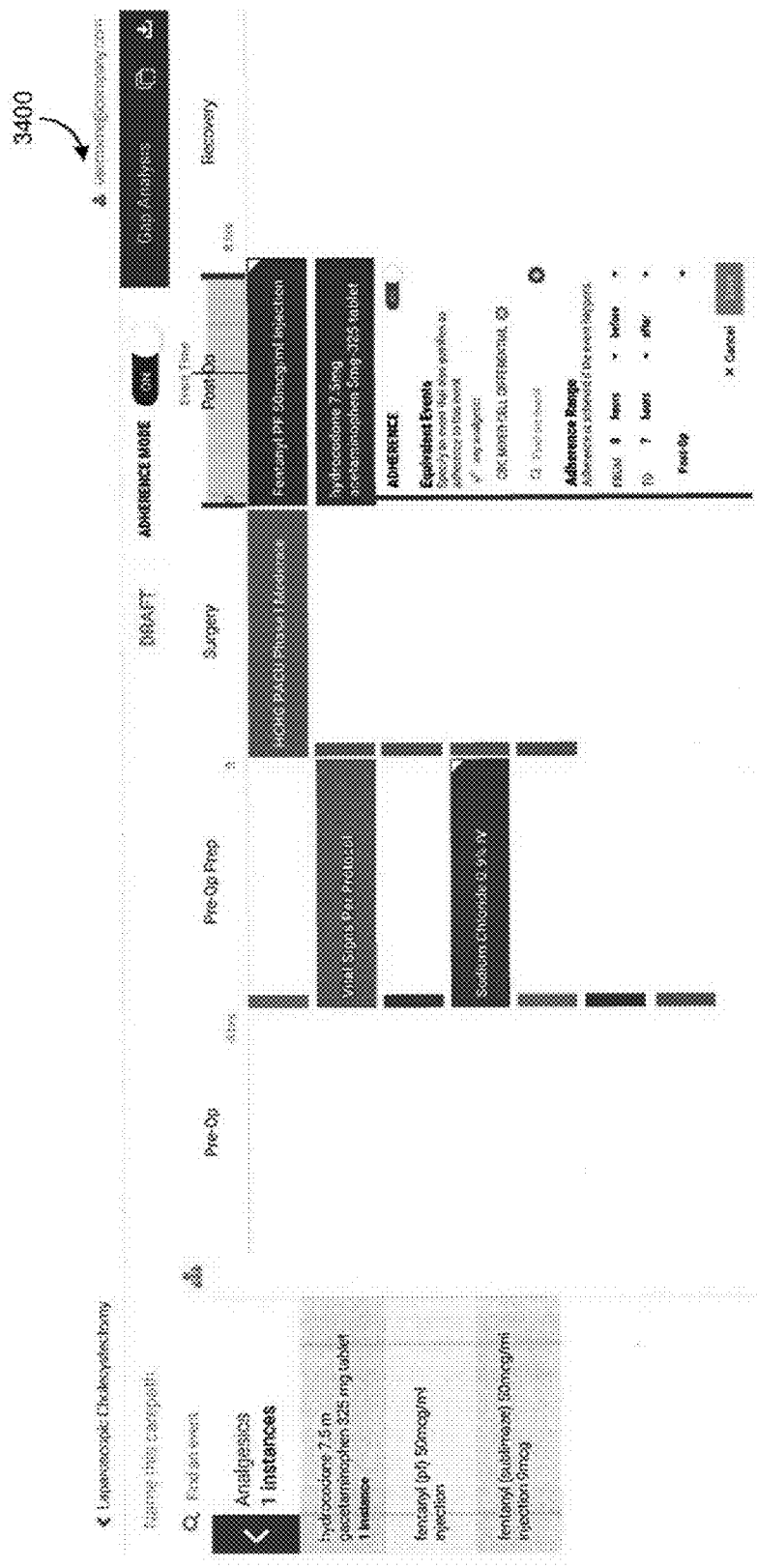
FIG. 34 depicts a carepath interface in some embodiments.

FIG. 34 depicts a carepath interface 3400 in some embodiments. In FIG. 34, the carepath interface depicts the carepath of FIGS. 28-33 with adherence mode activated. In this example, a user has selected hydrocodone 7.5 mg acetaminophen 5 mg-325 tablet during post-op and added "any analgesics" and "CBC mixed cell differential" as equivalents. In carepath interface 3400.

Figure 35:
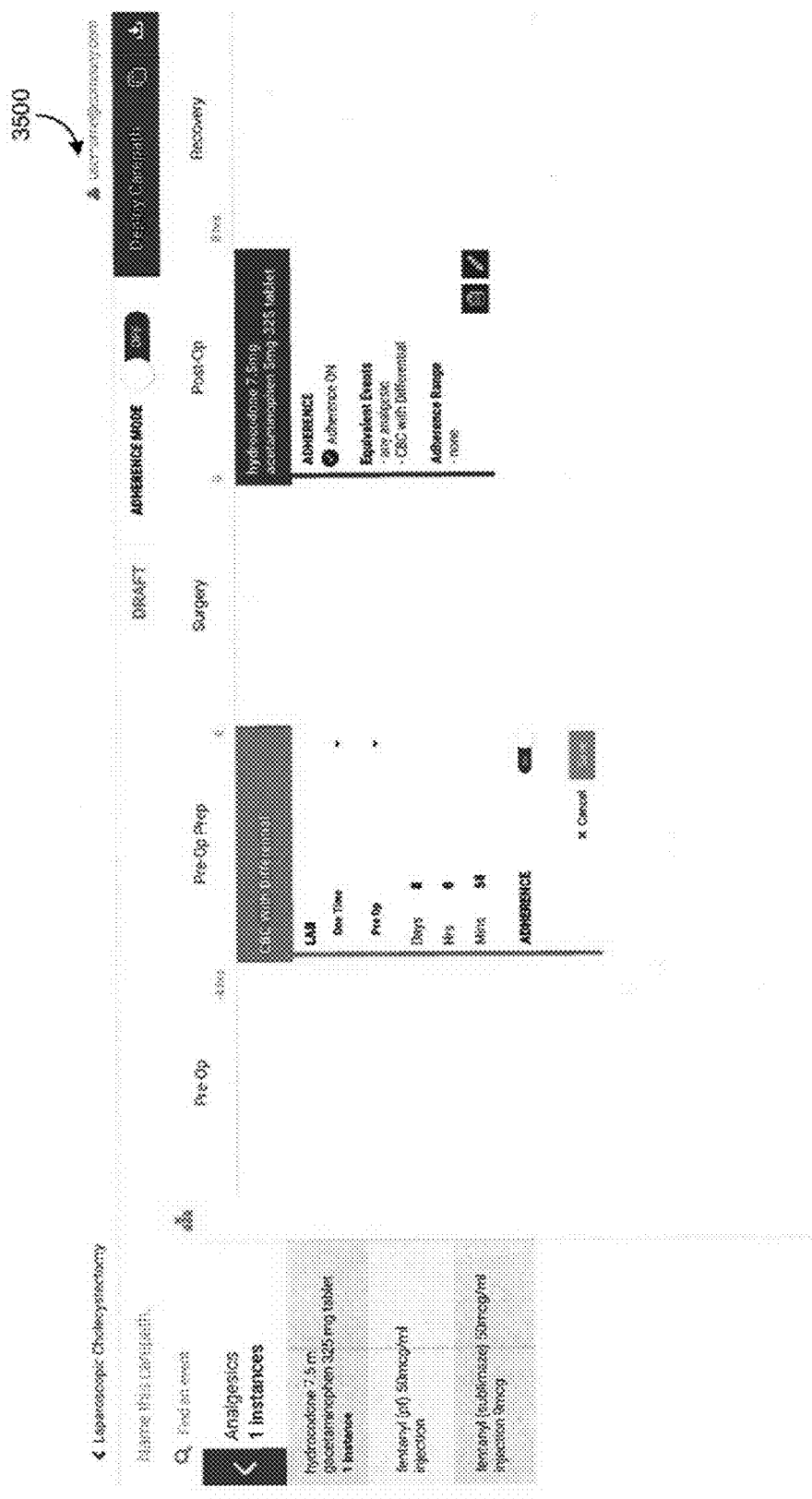
FIG. 35 depicts a carepath interface in some embodiments.

FIG. 35 depicts a carepath interface 3500 in some embodiments. In FIG. 35, the carepath interface depicts the carepath of FIGS. 28-34 with adherence mode activated. In this example, the user has turned off the adherence mode and is now able to change other events of the carepath that may or may not be a part of the adherence path. In some embodiments, events that are not a part of the adherence path may be added as adherence objects.

Figure 36:
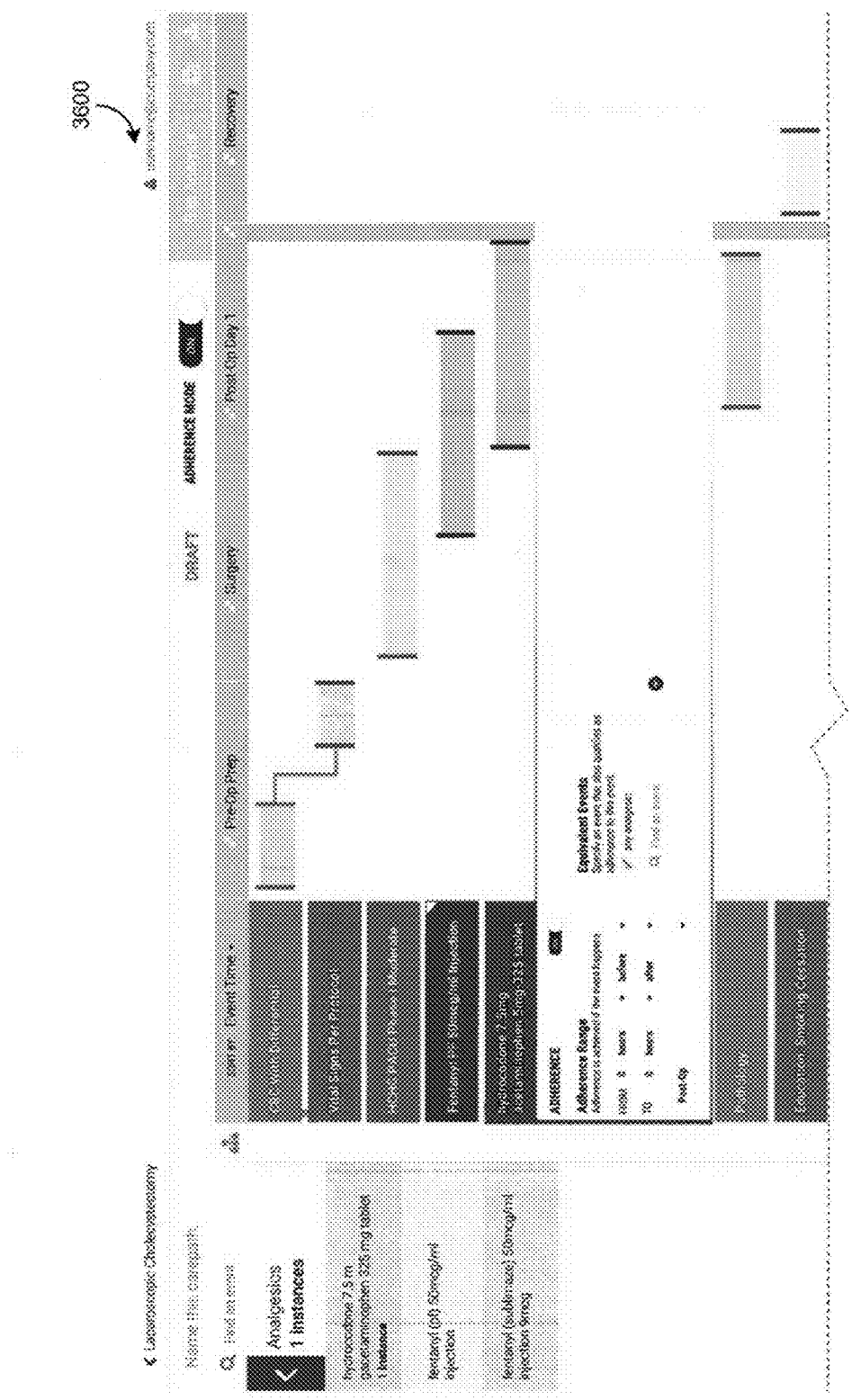
FIG. 36 depicts a carepath interface with sorted events based on time with a time graph in some embodiments.

FIG. 36 depicts a carepath interface 3600 with sorted events based on time with a time graph in some embodiments. In FIG. 36, the carepath interface depicts the carepath of FIGS. 28-35 with sorted events based on time. Each event may be sorted in a column based on time. The time graph may show when each event is to occur. The time graph may be similar to a gantt chart, a pert graph, line chart, bar chart, pie chart, or any other representation.

In various embodiments, the carepath interface 3600 may enable a user to select any of the events to get an expanded representation. It will be appreciate that the user may view events sorted by time with the time chart or in a manner similar to other carepath interfaces discussed herein.

The adherence scoring module 2110 may be configured to generate a score indicating whether an adherence object (including predicates) were satisfied for a particular patient's treatment. In various embodiments, the carepath selection module 2102 may receive an indication of a carepath (e.g., the user selects a carepath from an interface, the user provide a carepath identifier, or the user provides medical information related to a medical condition and the carepath selection module 2102 identifies a related carepath). The carepath selection module 2102 may retrieve a carepath and/or an adherence path of the carepath.

The user may also provide an entity identifier (e.g., a medical professional identifier that identifies a medical professional) and a time frame (e.g., over the last twelve months). The medical information record retrieval module 2106 may retrieve patient records of patients of the medical professional that received treatment for the medical condition during, before, or after the time frame from electronic medical records (or any storage). In some embodiments, the adherence path and adherence object identification module 2108 may identify all adherence objects of the adherence path including all rules.

The adherence scoring module 2110 may score whether each adherence object was satisfied (e.g., predicates were satisfied) for each patient. In one example, if a predicate is satisfied, then the adherence object may be scored as one. If not satisfied, the predicate may be scored as 0.

As discussed herein, the adherence scoring module 2110 may measure adherence (compliance) of an entity to the adherence path. The entity may be a medical professional (e.g., physician), group of medical professionals, facility (e.g., a group of medical professionals associated with a facility such as a specific hospital or clinic), or system (e.g., hospital system or insurance system). For each patient associated with a medical condition of a carepath, the adherence scoring module 2110 may score each adherence objects. In some embodiments, the score for that adherence object may indicate if that particular adherence object (including all rules of a predicate of that adherence object) was satisfied. In one example, the adherence scoring module 2110 may score a 0 (not satisfied) or a "1" (satisfied) for each adherence object of that particular patients adherence path.

The medical professional scoring module 2112 is configured to generate adherence scores for medical professionals (e.g., a doctor or any medical personnel responsible for patients). The medical professional scoring module 2112 may utilize the individual adherence object scores of the adherence path for each patient to generate a patient adherence path score indicating whether a one or more medical professionals complied with the adherence path of the carepath for that particular patient. In one example, the medical professional scoring module 2112 may total the number of adherence objects that were satisfied and generate a decimal score in comparison with the total number of adherence objects (e.g., if 10 adherence objects were satisfied out of 20, the patient adherence path score may be 0.5). It will be appreciated that the medical professional scoring module 2112 may generate adherence score for medical professionals in any number of ways.

The medical group scoring module 2114 is configured to generate adherence scores for a group of medical professionals. The medical group scoring module 2114 may utilize each patient adherence path score of a group of patient adherence path scores to generate a medical professional adherence score, a medical group adherence score, a facility adherence score, and a system adherence score. For example, the adherence scoring module 2110 may determine the individual patient adherence path scores of a set of patients of a particular medical professional that share a similar medical condition over a particular period of time. The adherence system may determine a medical professional adherence score based on the individual patient adherence path scores which may indicate the degree to which the medical professional complied with the adherence path of the carepath. For example, the medical professional scoring module 2112 may determine the average (e.g., mean, median, and/or mode) of the group of individual patient adherence path scores to generate the medical professional adherence score.

The medical group scoring module 2114 may generate a medical group adherence score. In various embodiments, the medical group scoring module 2114 may generate the medical group adherence score by averaging the individual medical professional adherence scores of medical professionals of the group. In some embodiments, the medical group scoring module 2114 may generate the medical group adherence score by averaging individual patient adherence scores of each patient of each medical professional associated with one or more carepaths.

It will be appreciated that the adherence system 1912 may score compliance with a particular adherence object across patients of any number of medical professionals. In various embodiments, the adherence object scoring module 2116 may determine if a particular adherence object was performed over any number of patients and scoring the compliance across any number of patients. The adherence object scoring module 2116 may then generate an aggregate adherence score for the adherence object (e.g., based on an average compliance including, for example, totaling the scores for all adherence objects divided by the total number of adherence object to determine the percent compliance). In various embodiments, the medical group scoring module 2114 may generate an aggregate adherence score for an adherence object based on medical information of people who are patients of one or more selected entities (e.g., medical professionals).

The following are some example definitions that may be used in scoring adherence of an adherence object. It will be appreciated that one, none, or any combination of the following may be utilized.

1) Boolean Code Expression (aka BCE):

In one example, this is an expression which evaluates events and returns true or false based on membership of the event-code in some subset of all the possible codes. This may support arbitrary Boolean expressions describing these subsets; that is, expressions involving AND (i.e., et intersection), OR (i.e., set union), and NOT (i.e., set complement). "Symbolic" names for subsets of codes, such as relatively fixed categories (e.g., ANALGESIC) provided by a customer standards body, and user-defined named groups (e.g., PRE-OP ANTIBIOTIC) may be utilized. The advantage of having symbolic descriptions is that a set such as (ANALGESIC AND NOT aspirin) may be easier to comprehend than a complete list of analgesics used in a large hospital, and also the expression will continue to apply to any new analgesic which is made available, so the expression does not need to be constantly update.

These can be denoted by (BCE . . . ) where the ellipses is replaced by a specific boolean code expression. A BCE may also be considered a function mapping a patient encounter to a set of events. The value of (BCE . . . )(patientEncounter) is the set of all events e in patientEncounter for which (BCE . . . )(e) is true.

2) Specific Time Interval (aka STI):

In one example, this is an expression which evaluates events and returns true or false based on whether or not the event-time lies within specific start/end bounds. In one example, it is denoted by (STI [start,end]), and (STI [x,y])(e) for an event e is true if and only if start<=eventTime(e) and eventTime(e)<=end. Such an expression may be easily visualized as occupying a segment on the time-axis for a patient encounter—the events for which this expression are true are precisely those lying within that segment. Further, such expressions can be easily and intuitively edited—adherence objects using such expressions can have the specific times in them readily adjusted by users (with appropriate administrative privileges).

3) Specific Count Expression (aka SCE):

In one example, this is an expression that returns true or false when applied to a set of events based on the total number of events in that set compared to specific ranges. That is (SCE [n,m])(s) is true if and only if n<=|s| and |s|<=m, where s is a set of events and is the number of events in that set. In some embodiments, events are not identified based on equality of code and timestamp—even if the same pill is given twice but logged at identical times (e.g., it is still two pills). Such expressions may have the same advantages as specific time intervals. In some embodiments, we can also think of the SCE as applying to the count.

4) Primitive Predicate (aka PP):

In one example, this a is function on patient encounters constructed from a BCE, STI, and SCE which returns 1 or 0 (which can be thought of as, respectively true or false). For a patient encounter, the expression [PP(BCE . . . )(STI[x, y])(SCE[a,b])](patientEncounter) is 1 (or true) only if the number of events in patientEncounter which simultaneously satisfy the STI and BCE is between a and b. For instance,

[PP(BCE aspirin)(STI[10,15])(SCE[2,3])](pE)

returns 1 if pE has either two or three 'aspirin events' in the time range [10,15], else it returns 0. PP instances may be combined as if they were boolean expressions.

5) Count Function (aka CF):

In one example, this is function on patient encounters constructed from a BCE, STI, and a bound m (together with an optional SCE) which returns the minimum of the number of events which match the BCE and STI and the bound. If the optional SCE is supplied, it returns the min of # and the bound provided that number satisfies the SCE. If the number fails to satisfy the SCE it returns 0. A CF also has a bound( ) method which returns m. A PP is a special case of a CF, where the bound is 1. We could extend CF's by taking weighted combinations of them to make WCF's. Also, we could extend CF's or WCF's by making them conditional on some boolean expression of PP's and then applying the CF/WCF only if the PP's return true on the encounter, else 0.

6) Real Value Predicate (aka RVP):

In one example, this is an expression which applies to real values and returns true if and only if the value lies in one of the intervals in the list. That is (RVP [1,4) (10, infinity))(10) is false and the same expression applied to 1000000.0 is true. In some embodiments, an RVP can be used to express that an absolute value is larger or smaller than some bound, as well as a very wide range of other constraints.] Instances are reasonably intuitive and capable of being displayed. It is a generalization of an STI.

7) Time Interval Function (aka TIF):

In one example, this is an expression defined for pairs of events which returns true or false depending on the difference between the timestamps. Specifically, (TIF((BCE . . . ) (BCE . . . ))(RVP . . . ))(e,e') returns true for a pair of events e,e' if and only if (RVP . . . )(eventTime(e)-eventTime(e')) is true, and is undefined unless e satisfies the first BCE and e' the second.

8) General Time Function (aka GTF):

In one example, like a TIF except that it can apply to one or more events and the arguments might be constrained by code. The idea is that we check the values of some general class of functions (e.g. rational functions or some other class) where the arguments have signatures given by BCE's, and we see if the specified function satisfies constraints given by RVPs. In a more specific example, a 2-argument GTF would look like:

(GTF((BCE . . . )(BCE . . . ))<some formula>(RVP . . . ))

Then the domain of the GTF would be any pair of events satisfying the respective BCE's and a pair would return true if and only if the formula applied to respective times satisfied the RVP. This is clearly getting far from the requirements A and C, but it is something which might be in some embodiments and is quite flexible.

9) Global General Time Constraint (aka GGTC):

In one example, (GGTC (BCE . . . )(GTF . . . ))(patientEncounter) applies BCE to patientEncounters to collect the set of all "true" events s. If GTF takes k arguments, we apply the GTF to every distinct k-subset of s in the domain of the GTF. We return true if and only if the GTF always returns true on its domain, else false. At its most general this allows us to verify fairly general constraints on the times of collections of events, such as that specified drugs are always used in a particular order or used far enough apart.

10) Global General Count Function (aka GGCF):

In one example, this is the analog of a CF which uses GGTC's to find sets of true events subject to constraints. It is possible that one might use it internally and expose different "idioms" (that is, expose a way to "make a constraint on pairs of drugs that A must come before B in a time window of length T," and the user can choose that "A and then B in ½ to 1 hr, and then no A or B for twelve hours after B," and the UI could generate a GGCF for enforcement.

The summary module 2118 is configured to provide summaries of entity scores to provide for high level analysis and assessment of adherence. The interface module 2120 is configured to generate interactive interfaces (e.g., carepath interfaces as those described herein) as well as dashboards that display summary information from the summary module 2118 as described herein.

The report module 2122 may create reports with the different adherence scores for any of the entities, patient medical data, carepaths, adherence paths, adherence scores for adherence objects, and/or any other information.

Figure 22:
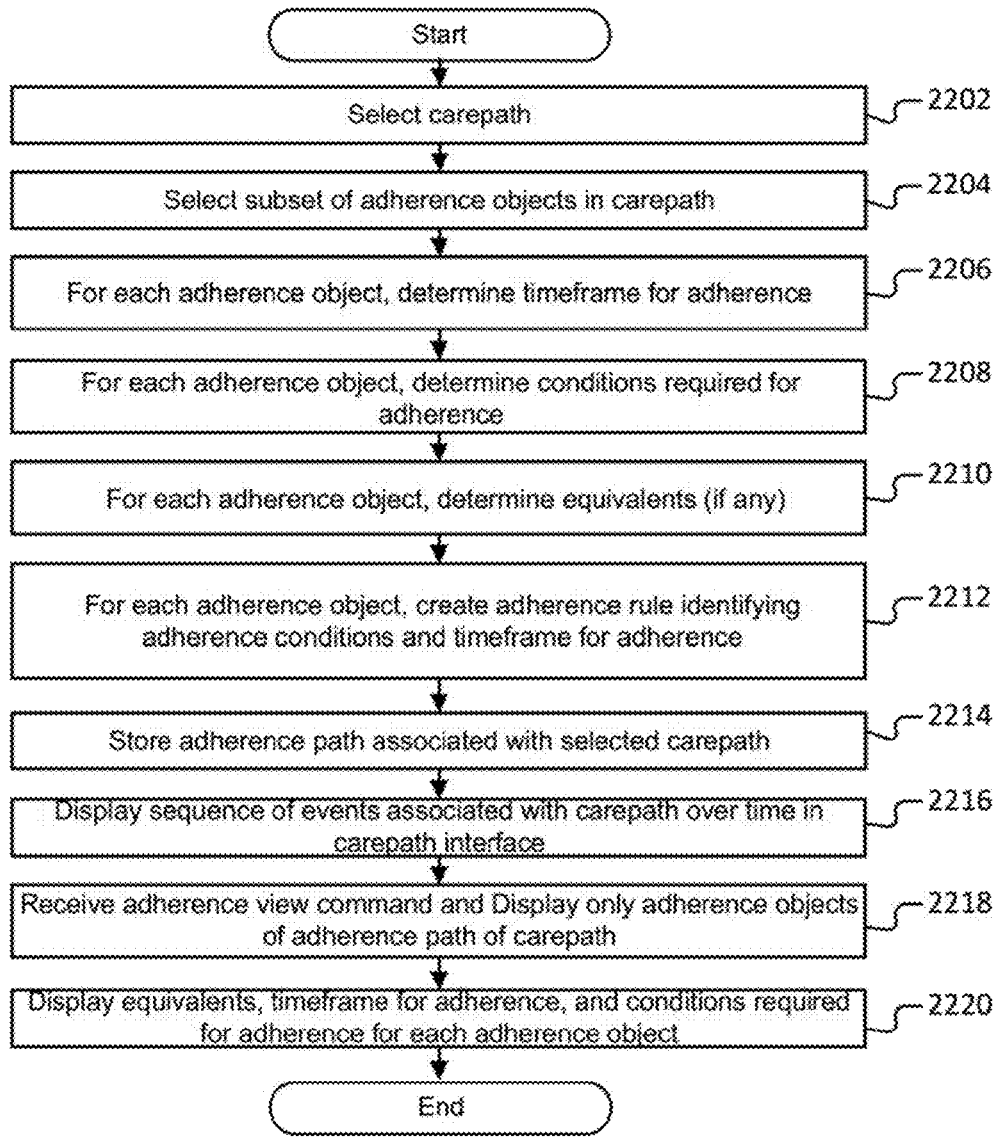
FIG. 22 depicts a flowchart for creating adherence objects in some embodiments.

FIG. 22 depicts a flowchart for creating adherence objects in some embodiments. In step 2202, a user may select a carepath. In some embodiments, the user provides a medical condition and the carepath selection module 2102 selects and/or retrieves a carepath related to the medical condition.

In step 2204, the adherence path and adherence object identification module 2108 may select a subset of events in the carepath as adherence objects. In various embodiments, the user may select a subset of events in the carepath and identify them as adherence objects. The adherence path and adherence object identification module 2108 may receive the selections (e.g., through an interface generated by the Interface module 2120) and may identify the selected events as adherence objects.

In step 2206, for each adherence object, the medical professional and time frame module 2104 or adherence path and adherence object identification module 2108 may indicate a time frame for adherence. For example, a user may indicate a specific time frame (e.g., a set number of hours before a time or event (e.g., surgery), a set number of hours after a time or event, or a specific duration between objects or events) for the adherence object to occur. For example, a user may provide a time frame and the medical professional and time frame module 2104 or adherence path and adherence object identification module 2108 may create a time frame predicate associated with the adherence object base do the provided time frame.

In step 2208, for each adherence object of the adherence path, the adherence path and adherence object identification module 2108 may receive, determine, and/or store predicates (e.g., conditions) associated with an adherence object. For example, the adherence path and adherence object identification module 2108 may determine that one or more other events must occur before and/or after the adherence object for the predicate to be satisfied. For example, the adherence score may be "1" indicating compliance if the adherence object was performed during the specific time frame AND the one or more other events that must occur before and/or after the adherence object are also performed. Otherwise, even if the adherence object is performed, the adherence score may be 0 indicating that treatment was not in compliance for that particular adherence object (and all of its conditions). Step 2208 may be optional.

In step 2210, the adherence path and adherence object identification module 2108 may determine equivalents for each adherence object if any. In various embodiments, the user may provide a number of equivalent events associated with an adherence object. In one example, the adherence scoring module 2110 may score an adherence object with equivalent events as being compliant if the treatment for a particular patient indicates that the event corresponding to the adherence object OR an event corresponding to an identified equivalent event was performed during the identified time frame. Otherwise, the adherence score for that object may be 0 indicating that treatment was not in compliance for that particular adherence object.

In step 2212, for each adherence object, the adherence path and adherence object identification module 2108 may create rules associated with the time frame, equivalents, and/or conditions to create the predicate for the adherence object. In step 2214, the adherence path and adherence object identification module 2108 may store the adherence object identifier for the adherence path and any predicates.

In step 2216, the interface module 2120 may generate an interface (e.g., carepath interface) depicting sequence of events associated with carepath over time. In step 2218, the interface module 2120 may receive an adherence view command to change adherence mode to active and display the adherence objects of the adherence path of the carepath (e.g., minimizing any events of the carepath that are not on the adherence path). In step 2220, the interface module 2120 may display conditions associated with a selected adherence object such as, for example, equivalents, time frame for adherence, and any conditions required for adherence.

Figure 37:
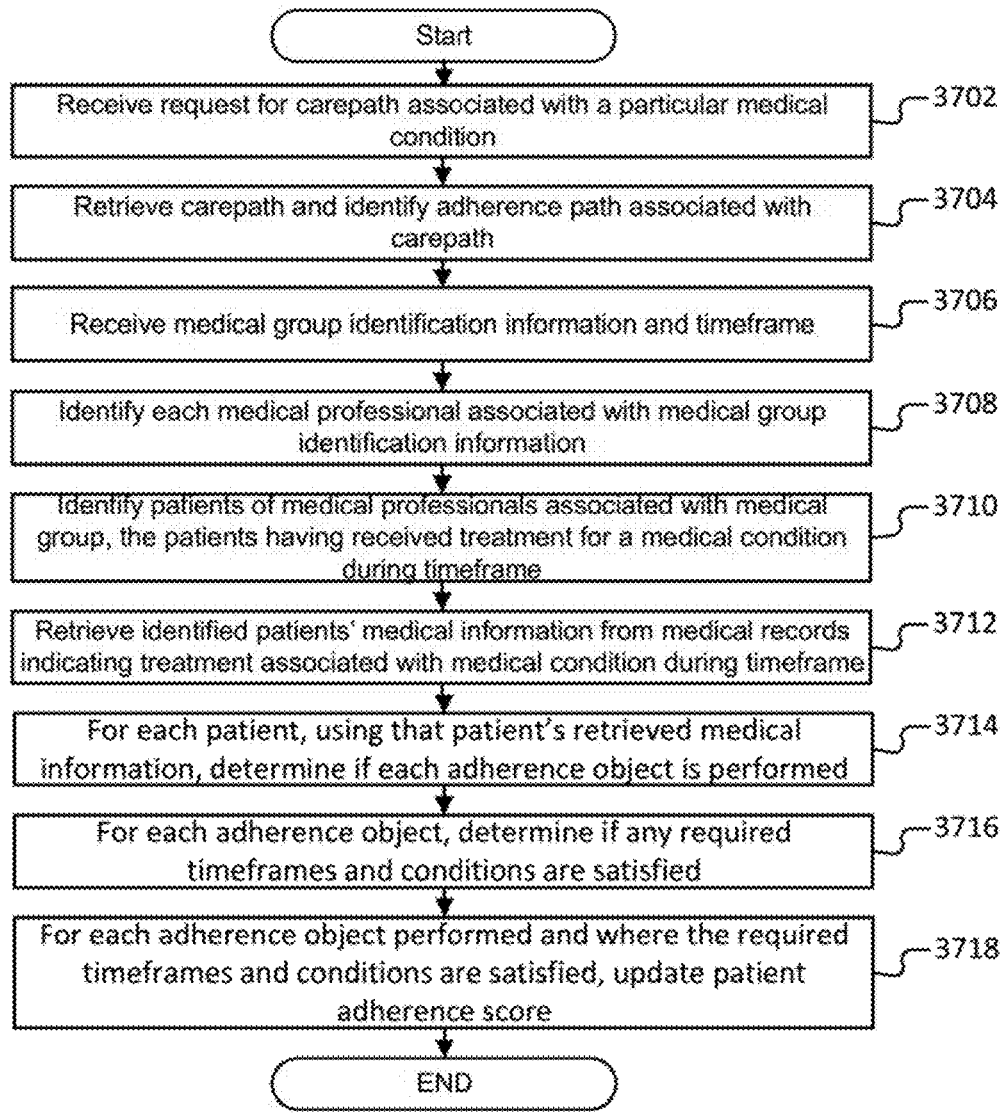
FIG. 37 is a flowchart for scoring adherence of adherence objects for patients, with a specific medical condition, of one or more medical professionals in some embodiments

FIG. 37 is a flowchart for scoring adherence of adherence objects for patients, with a specific medical condition, of one or more medical professionals in some embodiments. In step 3702, the carepath selection module 2102 receives a request for a carepath or adherence path associated with a particular medical condition. In step 3704, the carepath selection module 2102 may retrieve the carepath or adherence path associated with the particular medical condition.

In step 3706, the medical professional and time frame module 2104 may receive medical group identification information and a time frame. The medical group identification information may identify a group of medical professionals. The time frame may be a length of time associated with patients that received treatment or visited a medical facility during that time.

In step 3708, the medical professional and time frame module 2104 may identify each medical professional that is a member of the group of medical professionals. In step 3710, the medical information record retrieval module 2106 may identify medical patients of the medical professionals that are members of the group of medical professionals, the medical patients receiving treatment during the time frame for a particular medical condition.

In step 3712, the medical information record retrieval module 2106 may retrieve those patients medical information from medical records. In some embodiments, the medical information record retrieval module 2106 retrieves medical information related to treatment for the medical condition during the time frame for patients of the medical professionals.

In step 3714, the adherence scoring module 2110 may determine, for each patient, using the patient's retrieved medical information, whether the adherence object (including predicates such as during a time frame, equivalents, and/or any conditions) were performed. In step 3716, for each adherence object, the adherence scoring module 2110 may determine if any required time frames and conditions were satisfied. In step 3718, the adherence scoring module 2110 may generate a score for each adherence object if the predicate is satisfied. The adherence scoring module 2110 may generate an overall adherence score for each patient. For example, the adherence scoring module 2110, for each patient, may add all of the adherence scores and divide the total number of adherence objects of the adherence path to generate a score between 0 (no compliance) to 1 (full compliance).

Figure 38:
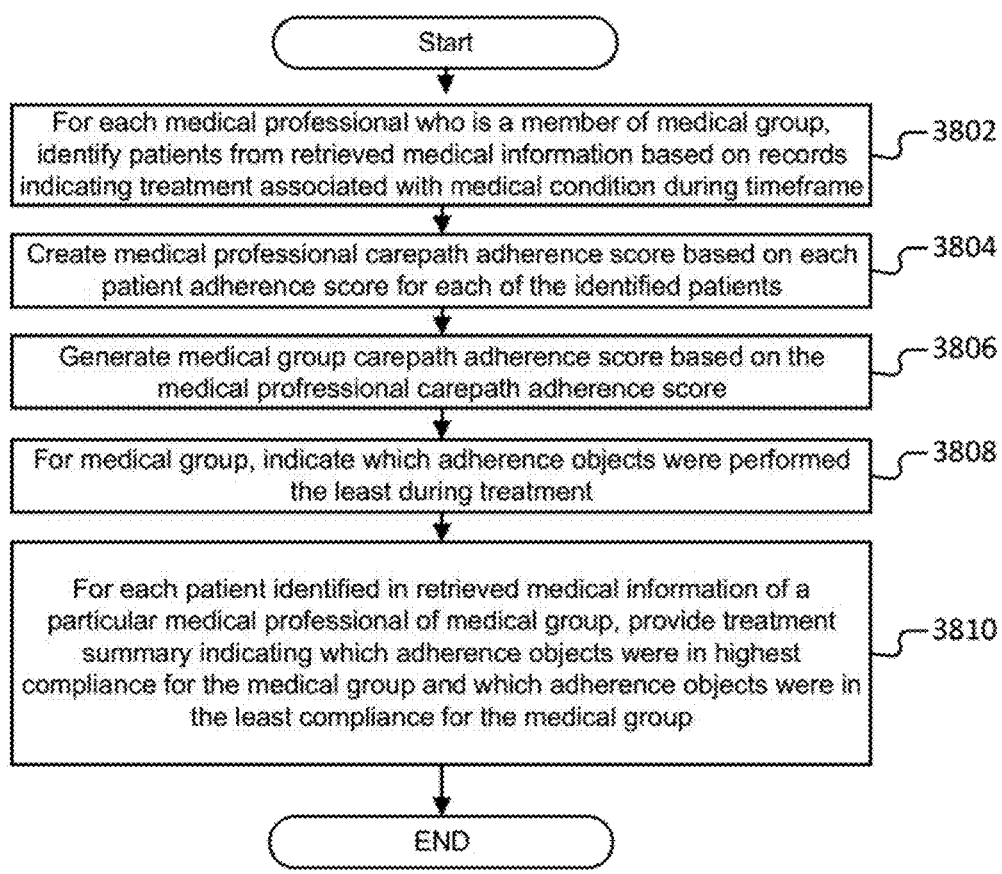
FIG. 38 is a flowchart for a method of generating a carepath adherence score for a medical group in some embodiments.

FIG. 38 is a flowchart for a method of generating a carepath adherence score for a medical group in some embodiments. In step 3802, the carepath selection module 2102, medical professional and time frame module 2104, and medical information record retrieval module 2106 identify a medical group (e.g., from a medical group identifier provided by a user), identify medical professionals that are members of the medical group, identify patients of the members of the medical group, and retrieve medical information from records of those patients indicating treatment for a medical condition during a time frame. In various embodiments, a user provides a medical group identifier, the medical condition (or carepath identifier), and the time frame.

In step 3804, the medical professional scoring module 2112 generates medical professional carepath adherence score for each medical professional based on each patient adherence score for each of the identified patients. For example, for each patient, the adherence scoring module 2110 may generate an adherence score for each adherence object of the adherence path associated with a carepath of the medical condition. The adherence scoring module 2110 may generate a patient adherence score indicating the number of adherence objects of the adherence path that were satisfied (e.g., by satisfying the predicate) in comparison to the total number of adherence objects of the adherence path. The medical professional scoring module 2112 may then generate a medical professional adherence score based on all of the patient adherence scores of those patients that are patients of that particular medical professional (e.g., the medical professional adherence score may be an average or other statistical measurement to generate a score between 0 and 1 based on the patient adherence scores of those patients that are patients of that particular medical professional).

In step 3806, the medical group scoring module 2114 may generate a group adherence score based on the medical professional score of each medical professional that is a member of the medical group. In one example, the group adherence professional score may be an average or other statistical measurement to generate a score between 0 and 1 based on the patient adherence scores of those patients that are patients of all medical professionals of the group. In another example, the group professional adherence score may be an average or other statistical measurement to generate a score between 0 and 1 based on the medical professional adherence scores of those medical professionals of the group.

In step 3810, the summary module 2118 may generate a summary for each patient identified in the retrieved medical information indicating those adherence objects that were in highest compliance (e.g., satisfied time frame and adherence conditions) and which adherence were in least compliance. For example, the summary module 2118 may review all patients of the medical group and all scores to determine which of the adherence objects had the highest scores and the lowest scores for a medical professional and/or the medical group. This information may indicate those adherence objects that have been completed the least. In some embodiments, the adherence system 1912 may compare outcomes of patients that were not in compliance to those patients that were in compliance to determine whether the adherence object is a differentiator. If there appears to be little impact, the adherence system 1912 may assess if equivalents were performed and add those equivalents to the adherence objects (e.g., further add rules as predicates) or remove the adherence object from the adherence path.

The summary may be generated and provided by the Interface module 2120 and/or the report module 2122.

Figure 39:
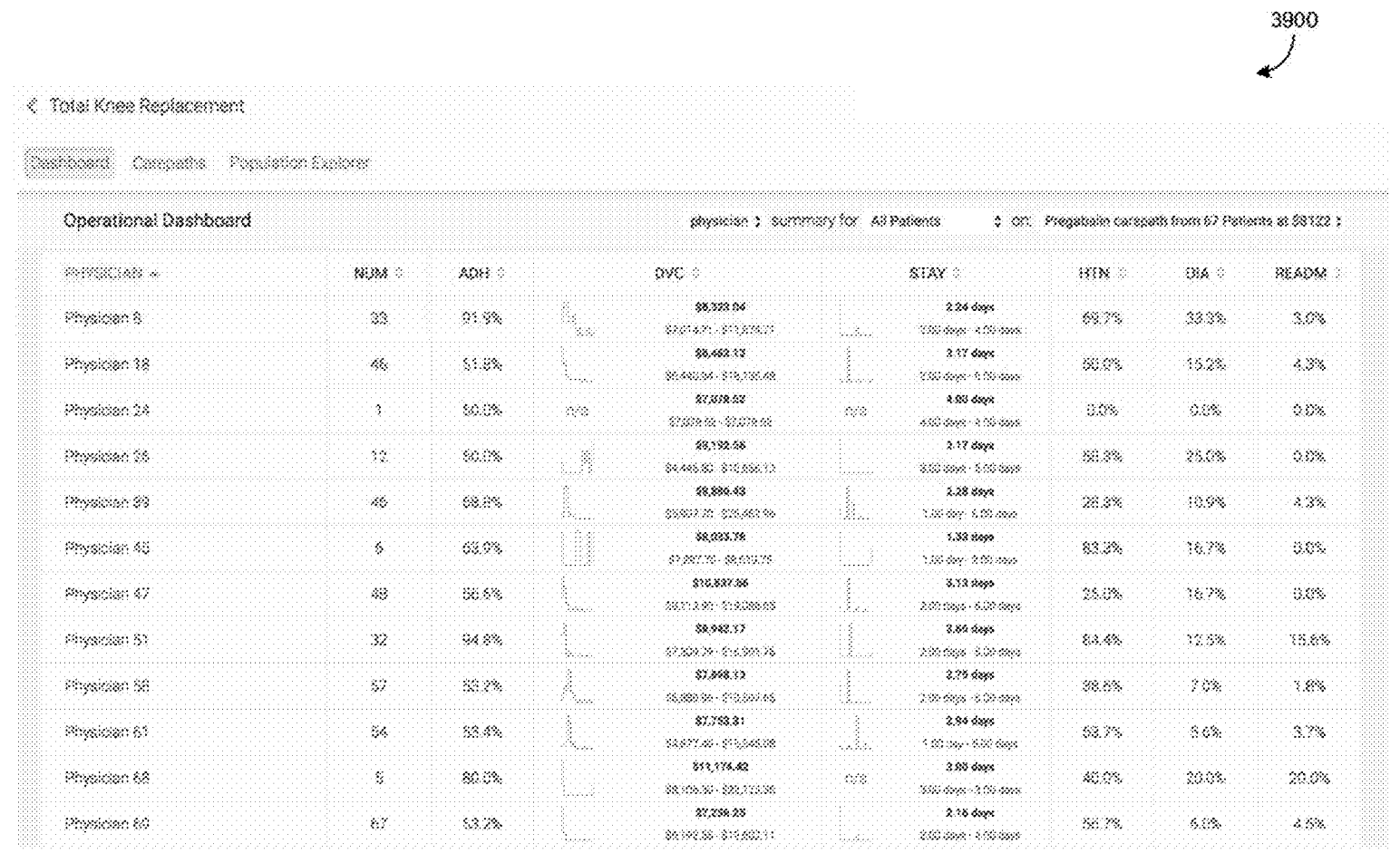

FIG. 39 depicts a physician operational dashboard 3900 for a total knee replacement in some embodiments. The interface module 2120 may generate the physician operational dashboard 3900. The physician operational dashboard 3900 indicates physicians in rows with the number of patients ("num") of that physician that received treatment for a particular medical condition (e.g., total knee replacement), and that physician's medical adherence score related to those patients. This physician operational dashboard 3900 also includes direct variable cost (DVC) average for that physician related to treatment of their patients, length of hospital stay, and other information.

It will be appreciated that a user may view how the different physicians of a group, facility or system compare to each other and the adherence path of a carepath. They may also assess the impact on cost, length of stay, and other factors that may be related to the treatment outcome.

Figure 40:
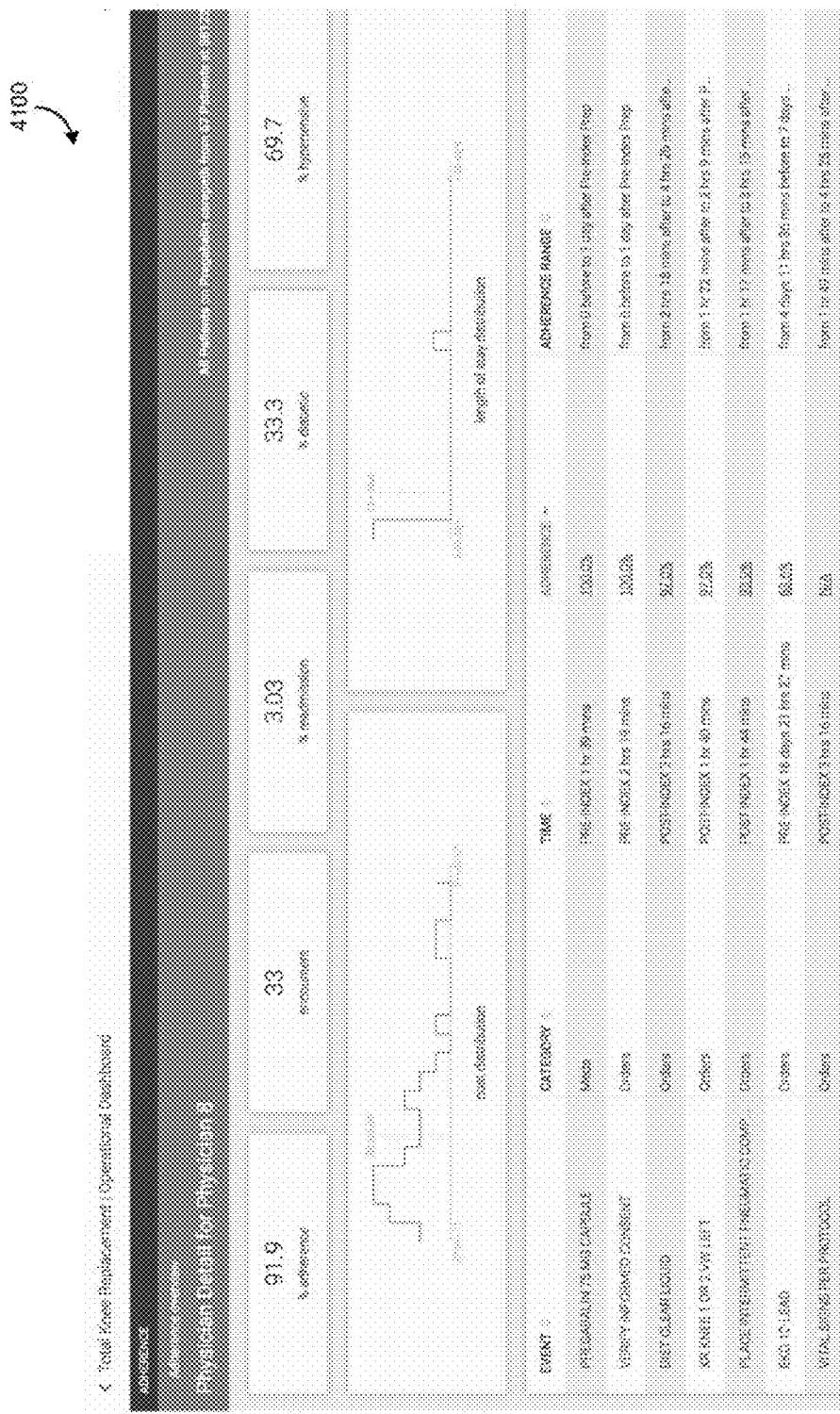
FIG. 40 depicts a physician dashboard of a particular medical professional identified in FIG. 39 in some embodiments.

FIG. 40 depicts a physician dashboard 4000 of a particular medical professional identified in FIG. 39 in some embodiments. In various embodiments, the interface module 2120 may receive a selection of physician 8 from the physician operational dashboard 3900. In response, the may generate the physician dashboard 4000 for physician 8. The summary module 2118 may further summarize the medical information of the patients that was retrieved in generate the adherence score of the particular medical professional for the physician dashboard 4000. The interface module 2120 may then generate the physician dashboard 4000.

In this example, the physician dashboard 4000 includes the adherence score, number of patients of that physician that received treatment for a particular medical condition (e.g., total knee replacement), and that physician's medical adherence score related to those patients. The physician dashboard 4000 may further include the percent of those patients that were readmitted and percentage of those with other conditions (e.g., diabetic and hypertensive). There may be any number of graphs, including, in the example of physician dashboard 4000, cost distribution for the cost of treatment of the patients and length of stay distribution. The physician dashboard 4000 may also include a list of adherence objects that may be ordered in any way (e.g., time, adherence, or other information. The list of adherence objects may be in a table that identifies a category of the type of adherence object, time frame, percent adherence to that particular adherence object across the patients (e.g., the thirty three patients for physician 8), and adherence range.

Figure 41:
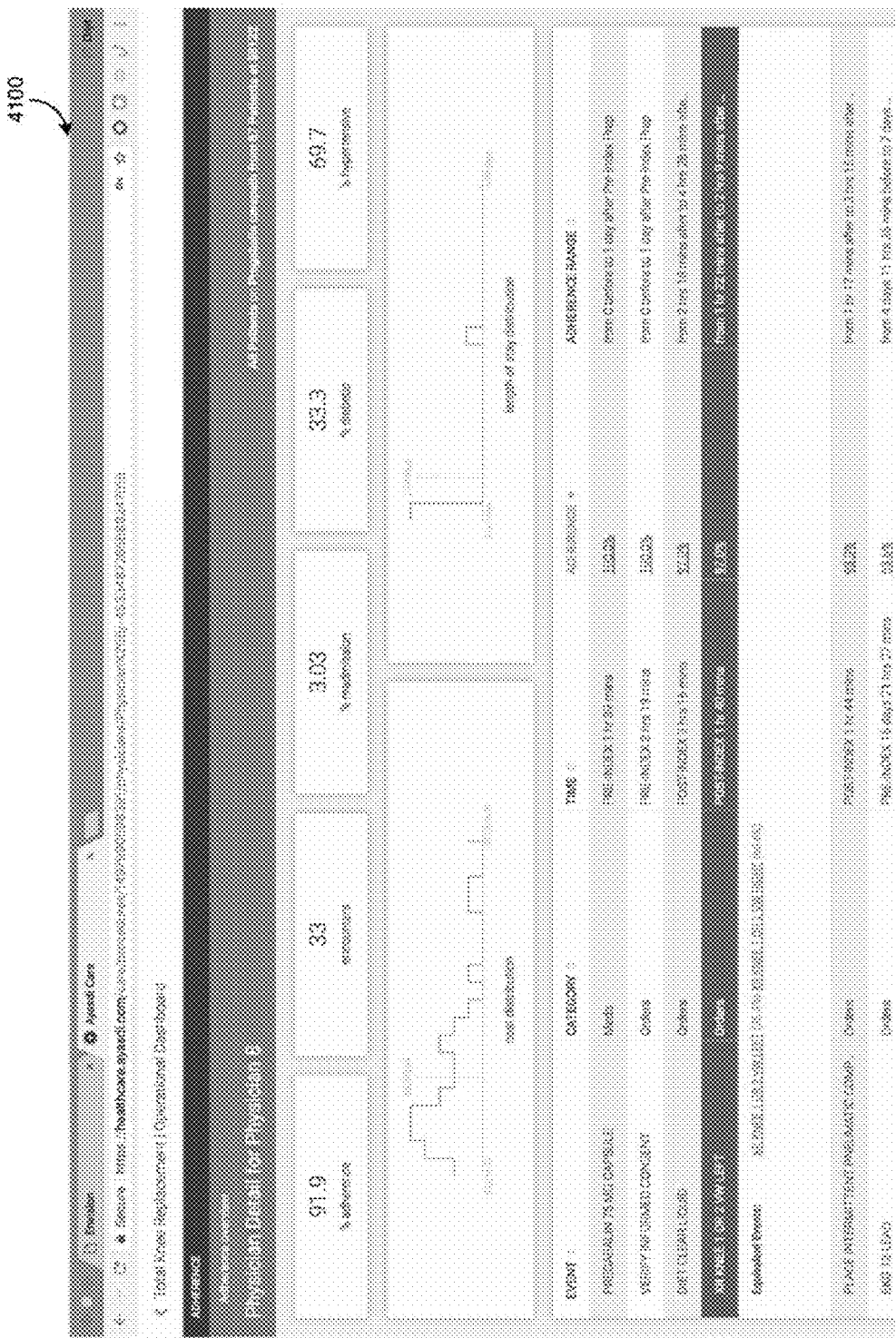
FIG. 41 depicts a physician dashboard of a particular medical professional identified in FIG. 40 in some embodiments.

FIG. 41 depicts a physician dashboard 4100 of a particular medical professional identified in FIG. 40 in some embodiments. In various embodiments, the interface module 2120 may receive a selection of an adherence object in the table of the physician operational dashboard 3900. In response, the interface module 2120 may generate an expanded discussion regarding that adherence object including, for example, equivalent events that may be satisfied to satisfy the adherence object (and improve the score of the adherence object).

Figure 42:
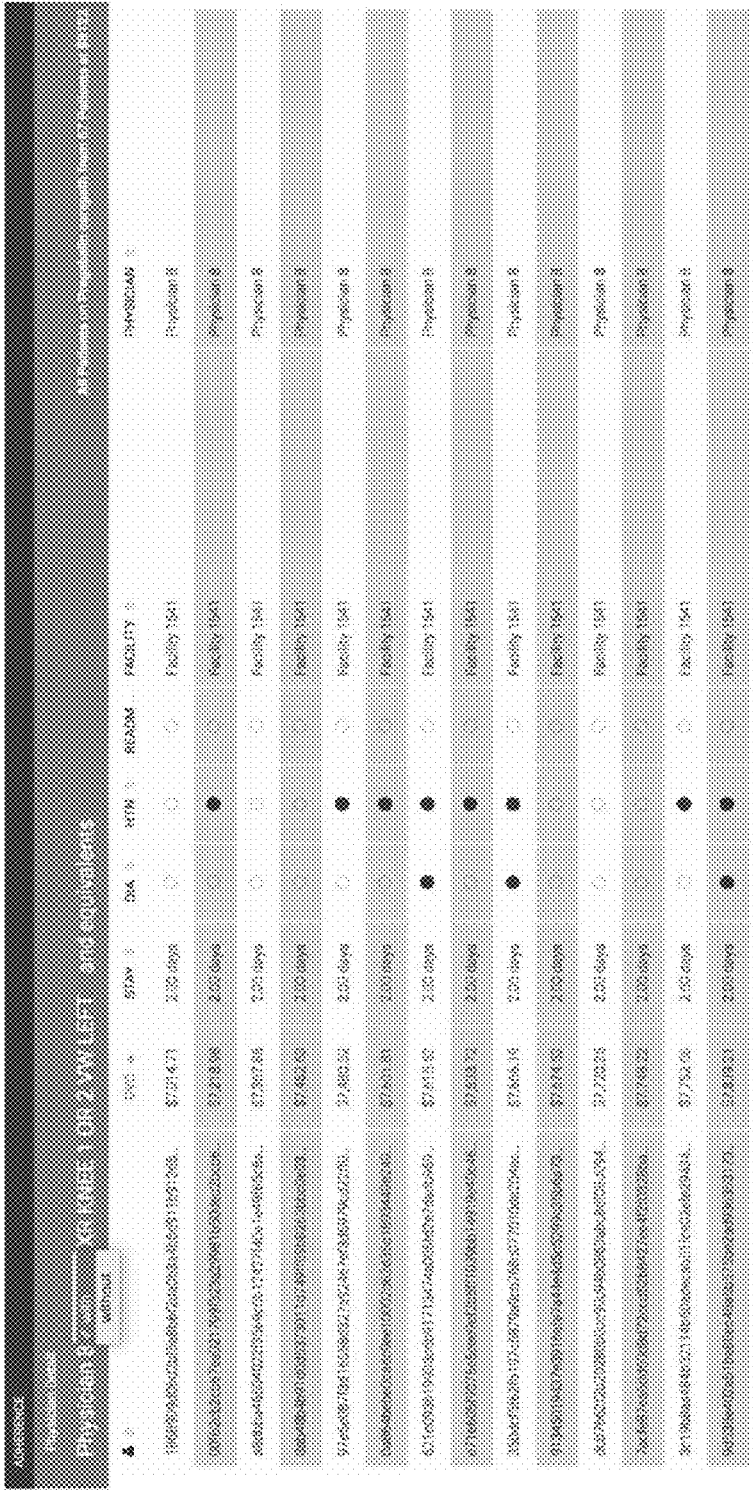
FIG. 42 depicts a physician detail interface of the particular physician of FIGS. 40-41 in some embodiments.

FIG. 42 depicts a physician detail interface 4200 of the particular physician of FIGS. 40-41 in some embodiments. The physician detail interface 4200 may include a table with information identifying the relevant patients that received the treatment including compliance with a particular adherence object, that particular patient's DVC, length of stay, facility, and the like. For example, the user may engage or select the expanded discussion of a particular adherence object in the physician dashboard 4100. The interface module 2120 may generate the physician detail interface 4200 detailing the patients that received that particular treatment (e.g., XR knee 1 or 2 VW left or XR knee 1 or 2 VW right).

Figure 43:
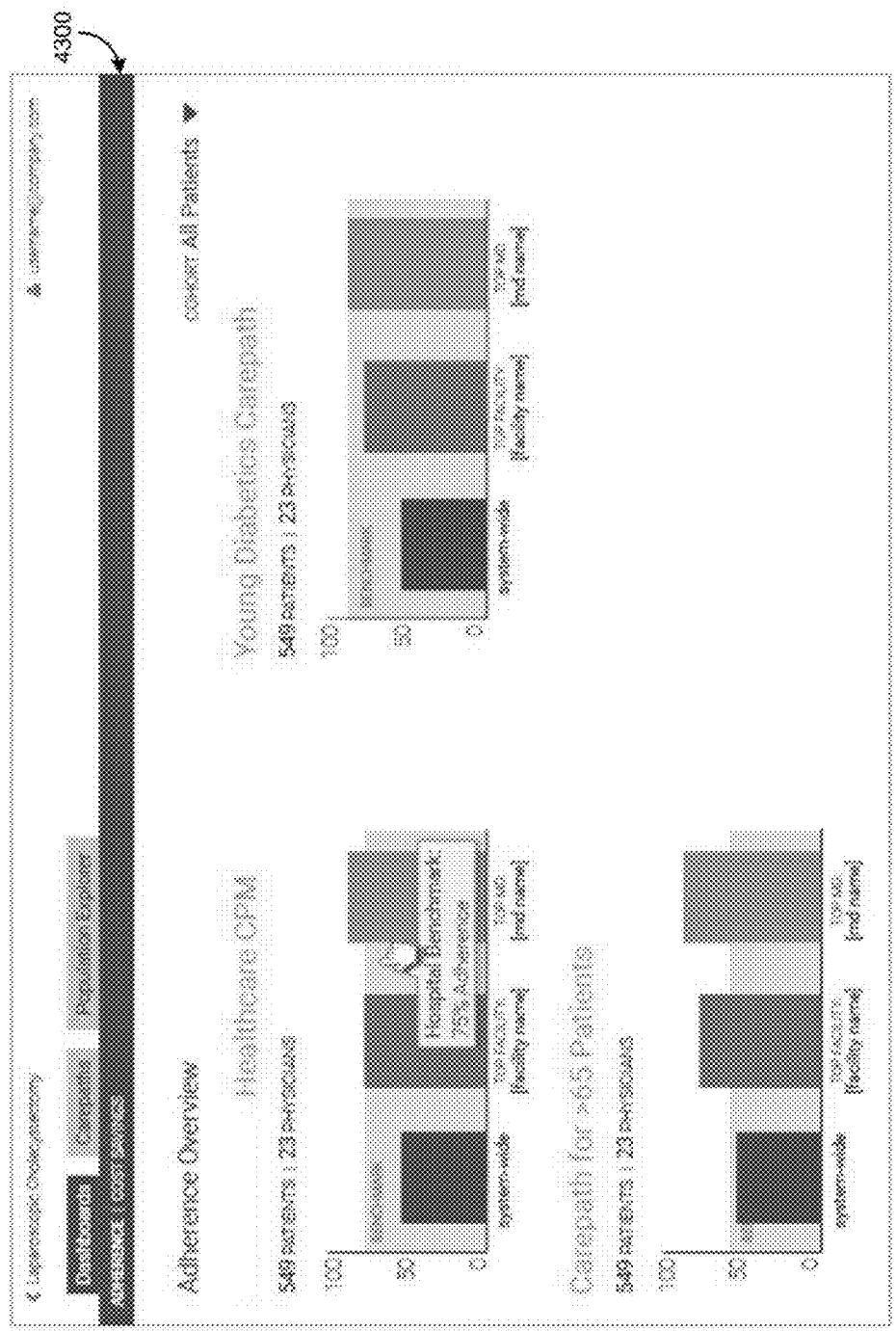
FIG. 43 depicts an adherence overview dashboard in some embodiments.

FIG. 43 depicts an adherence overview dashboard 4300 in some embodiments. The summary module 2118 may generate information for the adherence overview dashboard 4300. In various embodiments, the interface module 2120 may generate the adherence overview dashboard 4300. The adherence overview dashboard 4300 may include options to access different facilities, systems, and/or types of carepaths. In this example, the adherence overview dashboard 4300 includes bar graphs regarding a system's overall adherence overview and different types of deployed carepaths.

Figure 44:
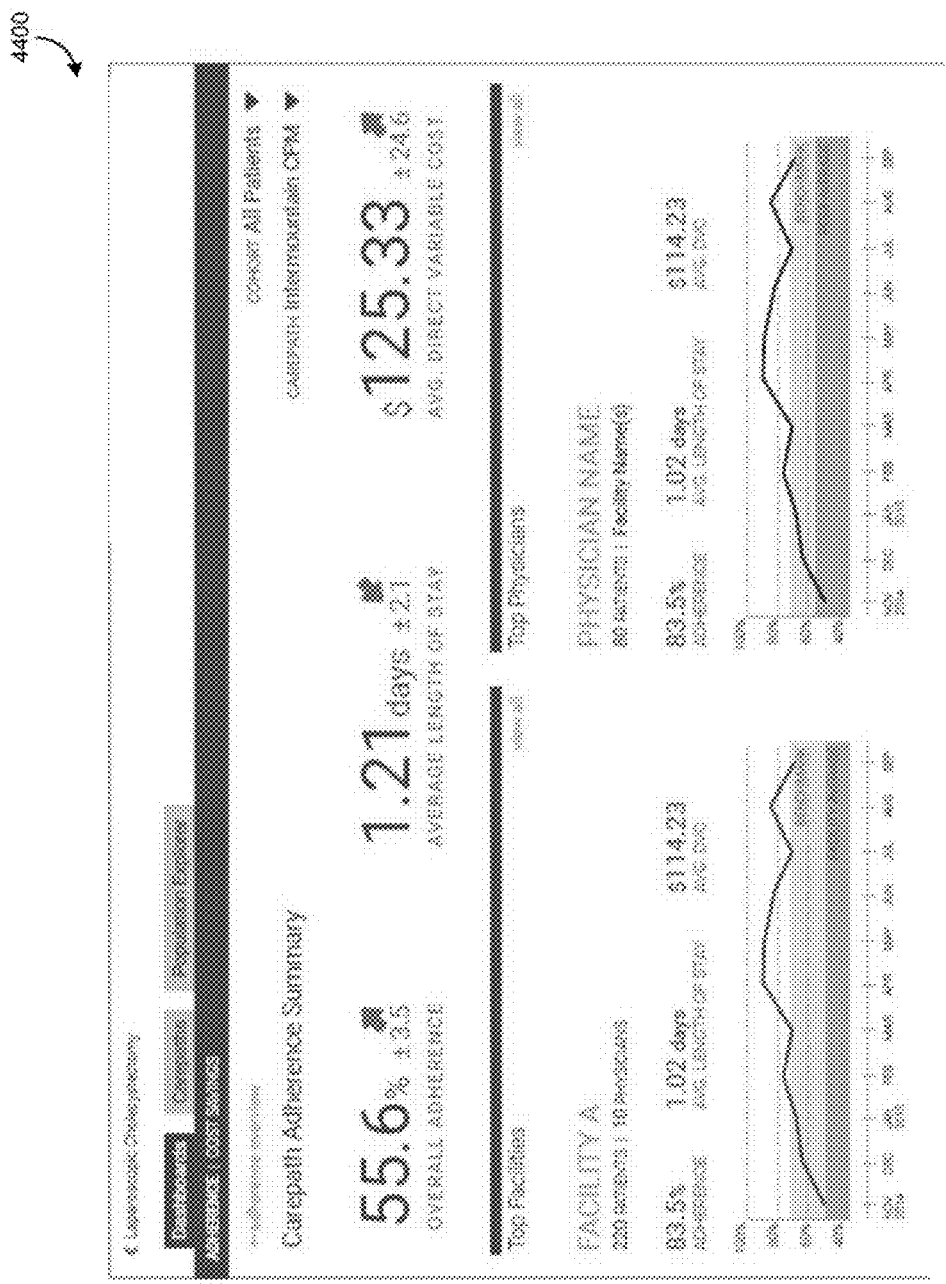
FIG. 44 depicts a system adherence overview dashboard in some embodiments.

FIG. 44 depicts a system adherence overview dashboard 4400 in some embodiments. In various embodiments, a user may interact or click on a system adherence overview in the adherence overview dashboard 4300. In response, the interface module 2120 may generate the system adherence overview dashboard 4400. The system adherence overview dashboard 4400 may include overall adherence scores (e.g., a system adherence score based on adherence scores of patients that received treatment related to medical conditions of any number of carepaths in the system), average length of stay for all such patients, and DVC for all such patients. The system adherence overview dashboard 4400 also includes charts for top facilities and top physicians (e.g., those facilities and physicians with highest adherence).

Figure 45:
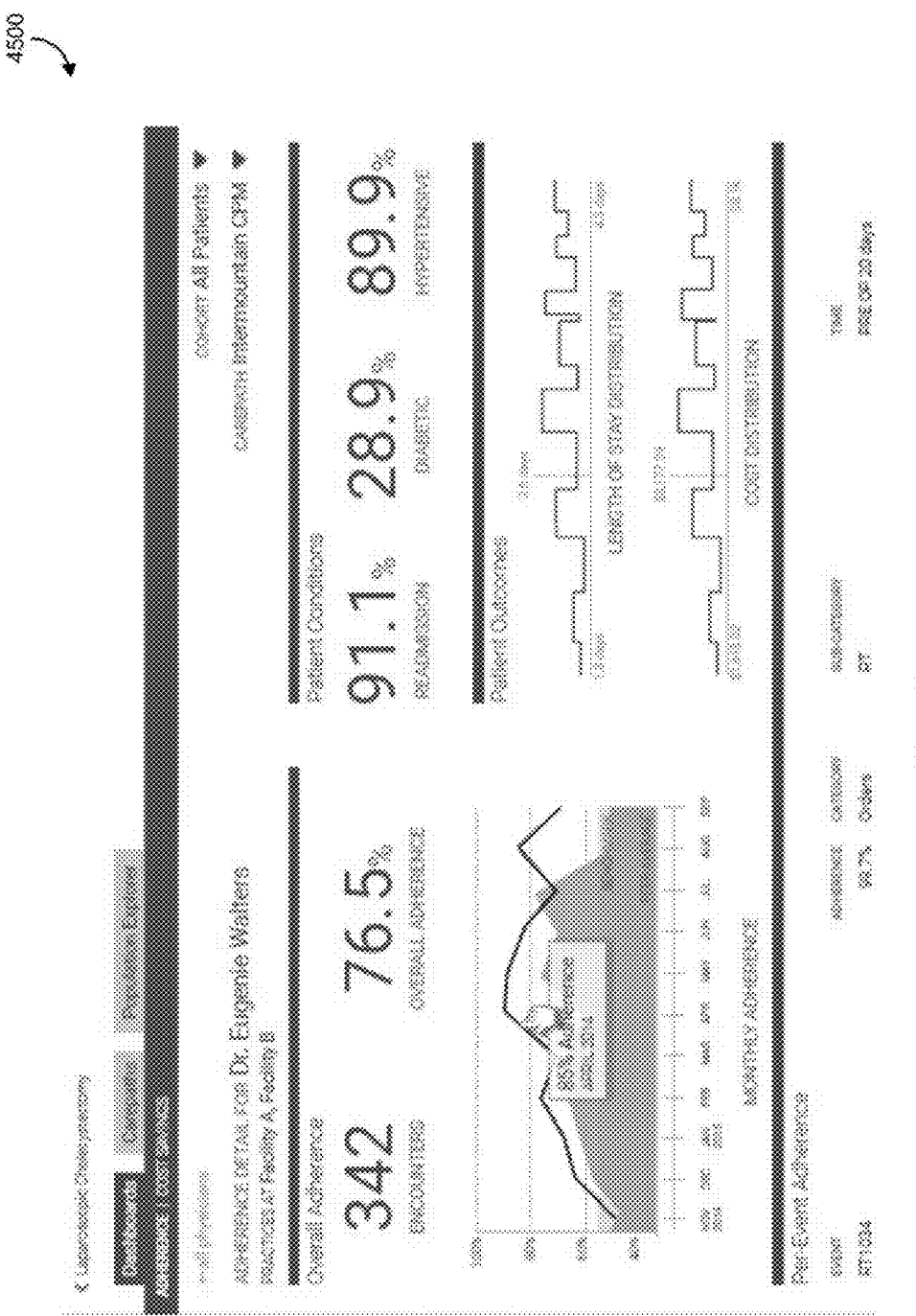
FIG. 45 depicts a physician detail overview dashboard in some embodiments.

FIG. 45 depicts a physician detail overview dashboard 4500 in some embodiments. In various embodiments, a user may interact or click on a particular physician adherence overview in the adherence overview dashboard 4300. In response, the interface module 2120 may generate the physician detail overview dashboard 4500. The physician detail overview dashboard 4500 for the physician with the highest adherence of the system may include overall adherence patients of that physician (e.g., with medical conditions related to carepaths), the total overall adherence score across any number (e.g., all) applicable carepaths of the system, patient conditions (e.g., percent readmission, diabetic, and hypertensive), patient outcomes (e.g., line graphs of length of stay distribution cost distribution and the like) and so forth. It will be appreciated that the physician detail overview dashboard 4500 may include physician details for any medical professional (e.g., the medical professional with the least adherence score(s) of any number of carepaths relative to other medical professionals of the system).

Figure 46:
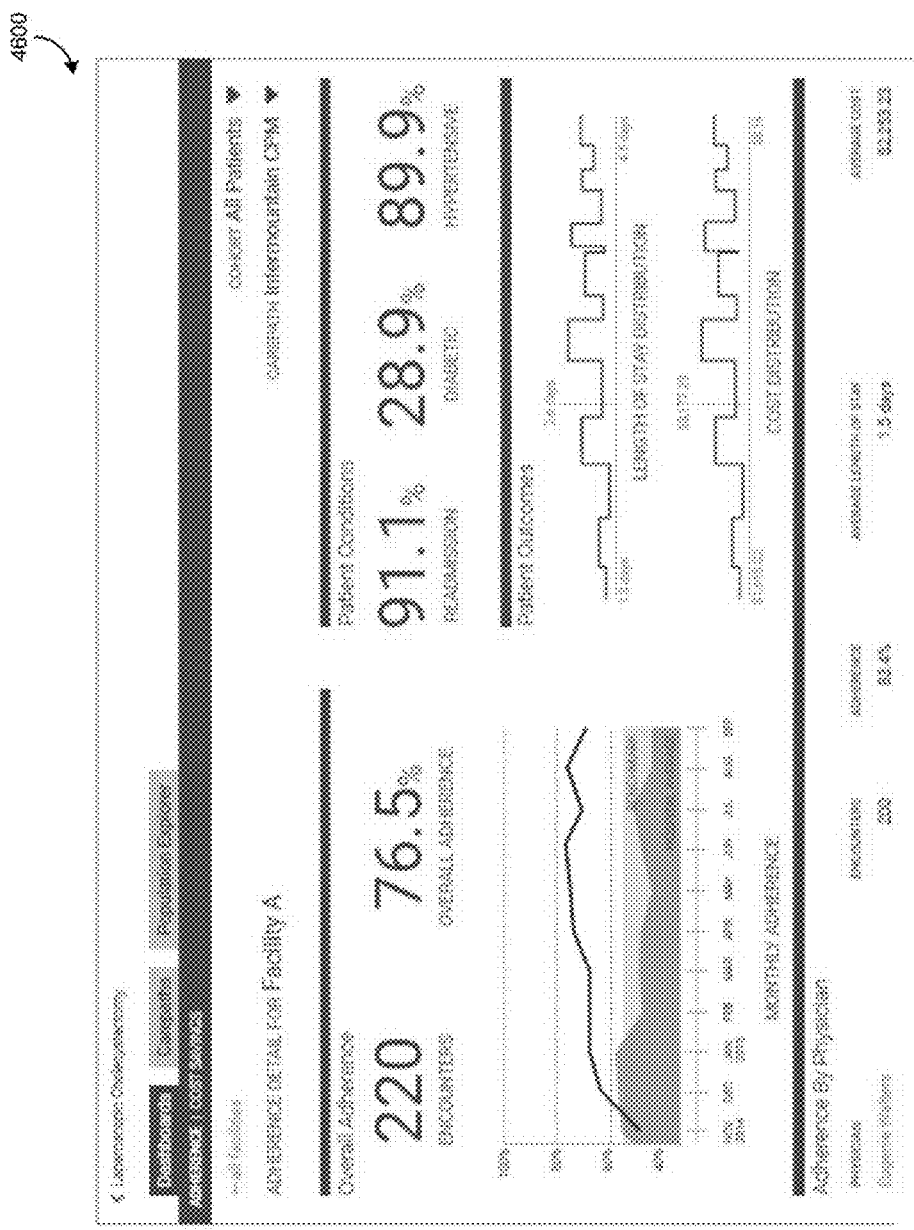
FIG. 46 depicts a facility detail overview dashboard in some embodiments.

FIG. 46 depicts a facility detail overview dashboard 4600 in some embodiments. In various embodiments, a user may interact or click on a particular facility in the adherence overview dashboard 4300. In response, the interface module 2120 may generate the facility detail overview dashboard 4600. The facility detail overview dashboard 4600 for the facility with the highest adherence of the system may include overall adherence patients of that facility, the total overall adherence score across any number (e.g., all) applicable carepaths of the system, patient conditions (e.g., percent readmission, diabetic, and hypertensive), patient outcomes (e.g., line graphs of length of stay distribution cost distribution and the like) and so forth. It will be appreciated that the facility detail overview dashboard 4600 may include facility details for any facility of the system (e.g., the facility detail overview dashboard 4600 of the facility with the least adherence score(s) of any number of carepaths relative to other facilities of the system).

Figure 47:
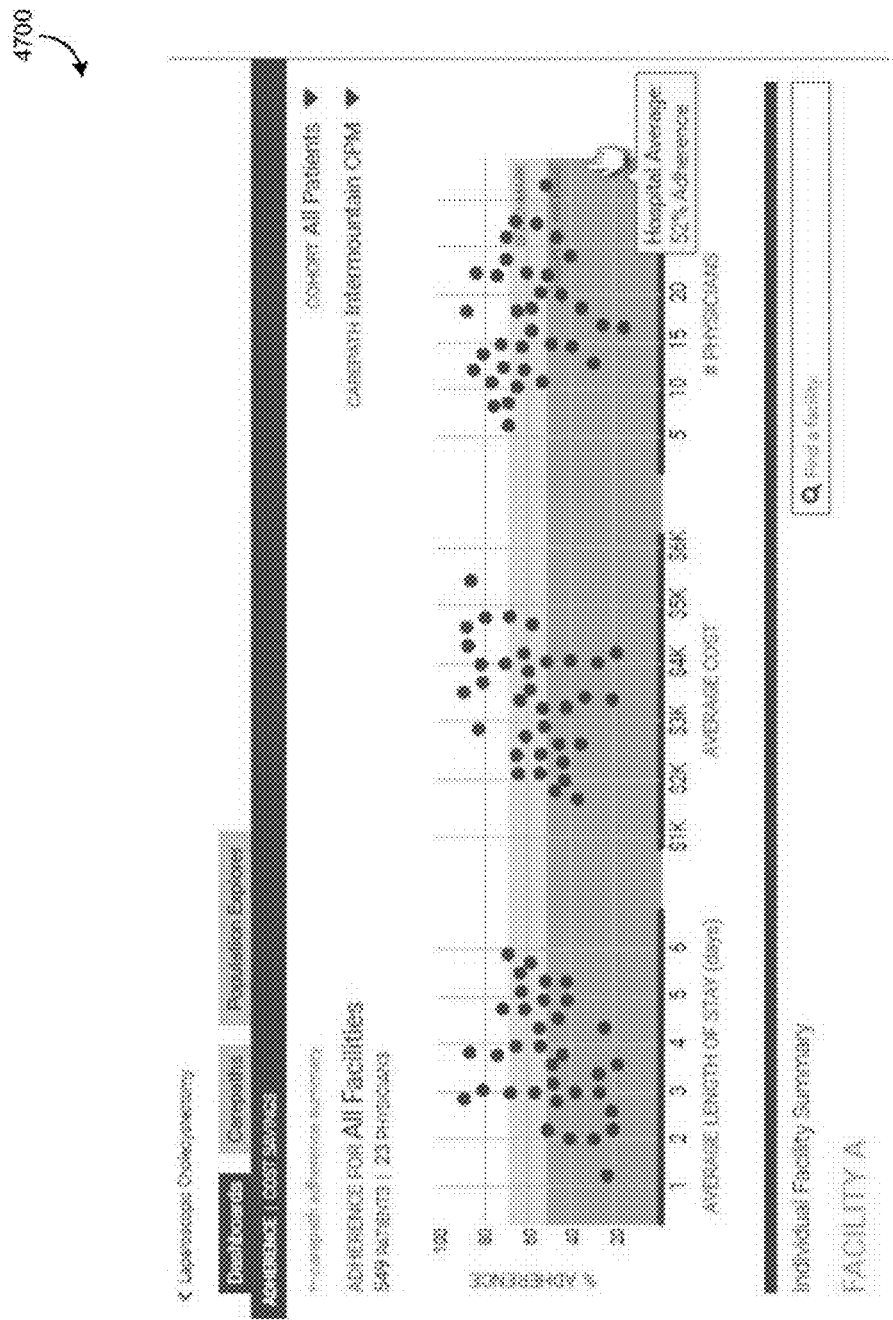
FIG. 47 depicts a facility dashboard in some embodiments.

FIG. 47 depicts a facility dashboard 4700 in some embodiments. In various embodiments, the facility dashboard 4700 may provide charts related to patients of any number of facilities of the system. The user may interact or click on a particular facility in the adherence overview dashboard 4300 and request the facility dashboard 4700. In response, the interface module 2120 may generate the facility dashboard 4700. The facility dashboard 4700 may include any number of charts including, but not limited to average length of stay against percentage of adherence, average cost against percentage of adherence, and number of physicians against percentage of adherence. The facility dashboard 4700 for the facilities may assist in assessment of the impact of adherence to adherence paths of a carepaths in general (e.g., in terms of length of hospital stay, average cost, and number of medical professionals that are in compliance). The charts may further be used to provide averages and/or benchmarks. For example, the darker grey indicates hospital average and the lighter grey indicates benchmark.

Figure 48:
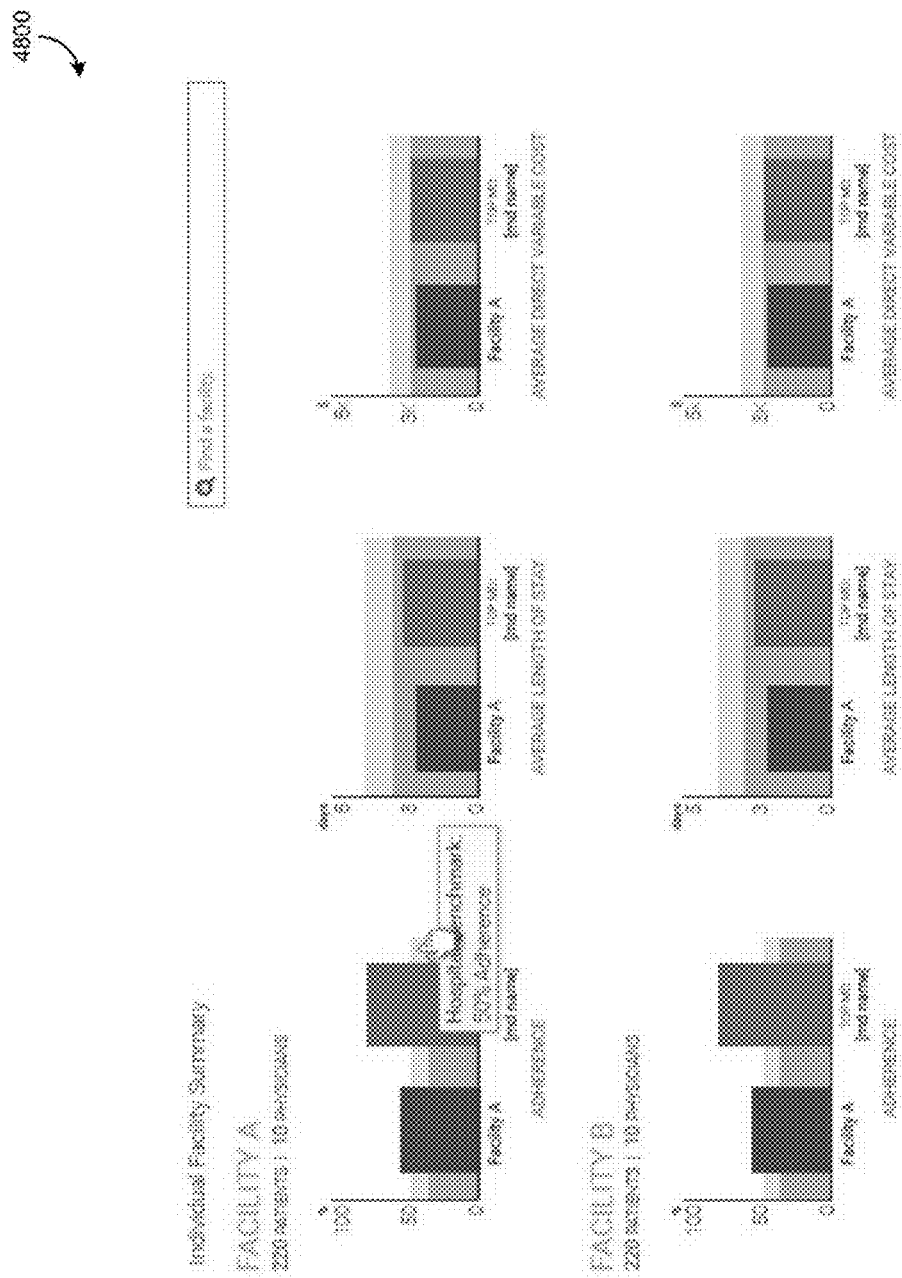
FIG. 48 depicts individual facility bar graphs interface in some embodiments.

FIG. 48 depicts individual facility bar graphs interface 4800 in some embodiments. In various embodiments, the individual facility bar graphs interface 4800 may provide bar graphs related to each facility of the system. The individual facility bar graphs interface 4800 may indicate the total number of patients for a given time frame that received treatment related to at least one carepath. In this example, facility A of the system had 220 patients of 10 physicians that received treatment for a medical treatment related to a carepath during a given time frame. The bar graphs can include any information related to that facility. For example, facility A may include bar graphs indicate the total adherence for the facility and the best physician (with the highest adherence score(s)), the average length of hospital stay for patients of the facility and the average length of hospital stay for patients of the best physician, average direct variable cost for patient treatment of the facility and the average direct variable for patients of the best physician, and so on. This information may be generated for each facility.

Figure 49:
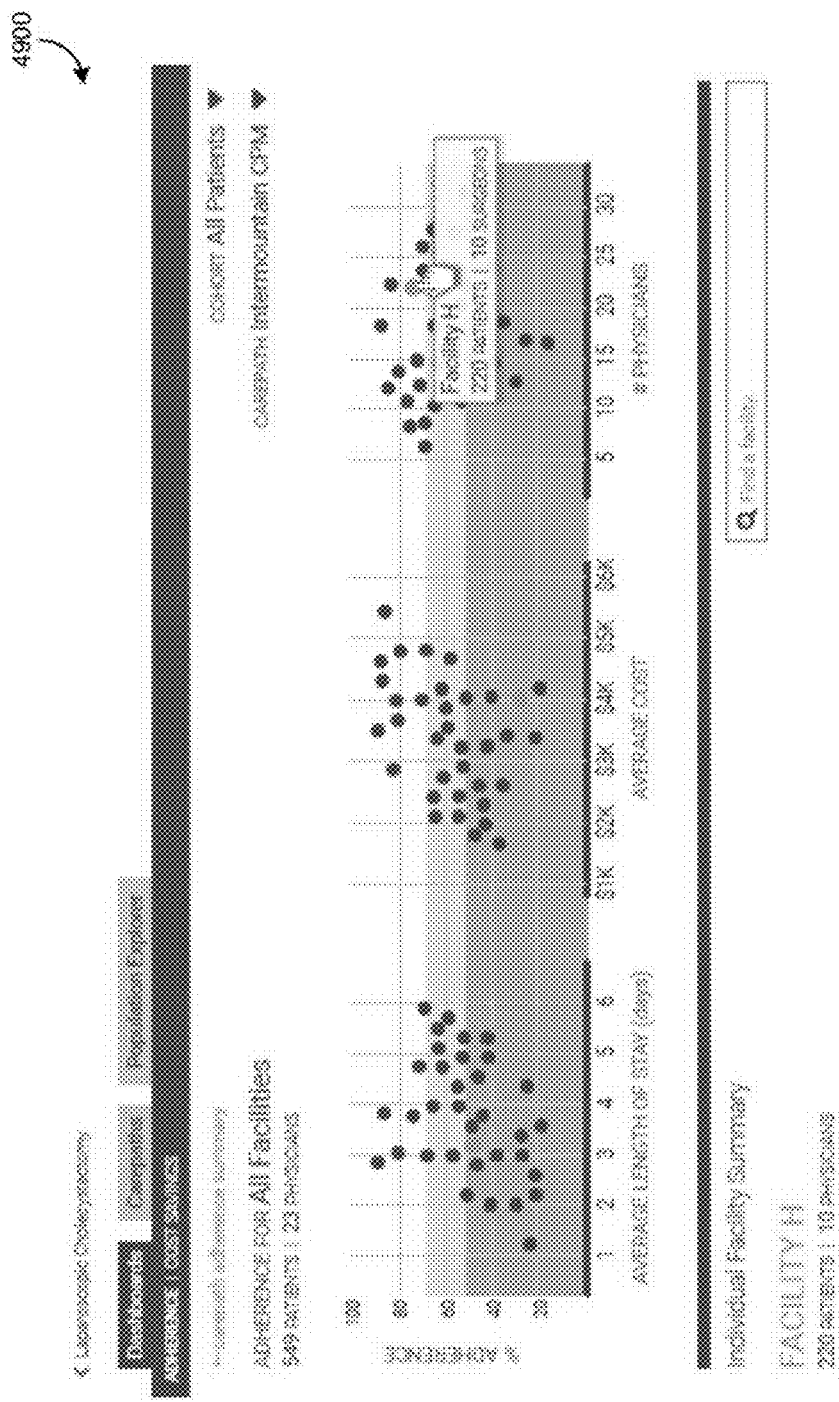
FIG. 49 depicts a facility dashboard in some embodiments.

FIG. 49 depicts a facility dashboard 4900 in some embodiments. The facility dashboard 4900 may be similar to the facility dashboard 4700. In various embodiments, the interface module 2120 may enable a user to select one of the dots of the charts to bring up an individual facility chart (e.g., bar graphs as described in FIG. 47 but for only the selected facility). In this example, the user selected the dot corresponding to facility H. the interface module 2120 may display information related to facility H below the charts.

Figure 50:
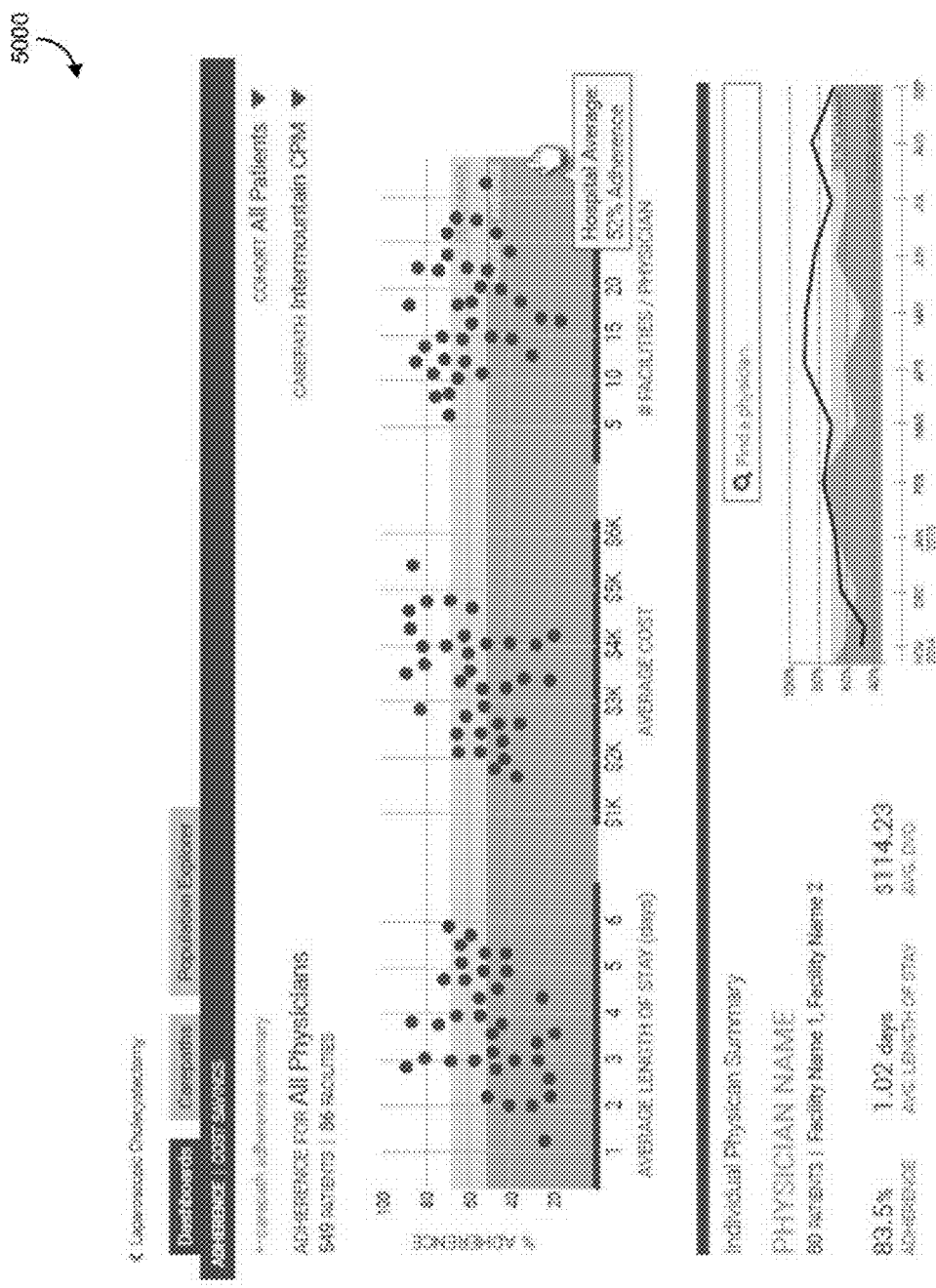
FIG. 50 depicts a medical professional dashboard in some embodiments.

FIG. 50 depicts a medical professional dashboard 5000 in some embodiments. In various embodiments, the medical professional dashboard 5000 may provide charts related to patients of any number of medical professionals of the system. The user may interact or click on a particular medical professional in the adherence overview dashboard 4300 and request the medical professional dashboard 5000. In response, the interface module 2120 may generate the medical professional dashboard 5000. The medical professional dashboard 5000 may include any number of charts including, but not limited to average length of stay against percentage of adherence, average cost against percentage of adherence, and number of physicians against percentage of adherence. The medical professional dashboard 5000 for the facilities may assist in assessment of the impact of adherence to adherence paths of a carepaths in general (e.g., in terms of length of hospital stay, average cost, and number of medical professionals that are in compliance). The charts may further be used to provide averages and/or benchmarks.

For example, the darker grey indicates hospital average and the lighter grey indicates benchmark.

The medical professional dashboard 5000 may also depict individual medical professional charts and information related to each medical professional of the system. The individual medical professional charts and information may indicate the total number of patients for a given time frame that received treatment related to at least one carepath. In this example, medical professional A of the system had 80 patients, had an adherence score of 83.5%, the average length of stay for those patients was 1.02 days, and the average DVC was $114.23. There may be charts demonstrating adherence of the medical professional over time.

The present invention(s) are described above with reference to exemplary embodiments. Various modifications may be made and other embodiments may be used without departing from the broader scope of the present invention. Therefore, these and other variations upon the exemplary embodiments are intended to be covered by the present invention.

The invention claimed is:

1. A method comprising:
   receiving a protocol associated with a particular medical condition, the protocol comprising a set of events to occur in treatment of the medical condition;
   selecting a subset of the events of the protocol to be adherence objects of an adherence path;
   determining a time frame predicate for each adherence object of the adherence path, the time frame predicate indicating a time frame during which an event related to the adherence object is to be performed;
   determining an object predicate for each adherence object of the adherence path, the object predicate indicating one or more codes of an electronic health record system associated with an event related to the adherence object, the electronic health record system storing medical information related to a medical entity, wherein a protocol specific adherence object is an adherence object of the adherence path of the protocol that was performed for treatment related to the protocol during the time frame indicated in the time frame predicate;
   receiving a medical condition identifier indicating a medical condition, a treatment time frame identifier indicating a time frame during which treatment is to be performed, and a medical entity identifier identifying the medical entity;
   retrieving patient information from medical records of patients of the medical entity, the patients having received treatment related to the medical condition during the treatment time frame, the patient information indicating events related to treatment, the events being at least a sub-subset of the subset of the events of the protocol;
   for each patient, using that patient's patient information;
   for each protocol specific adherence object that includes at least one code from the patient's patient information in the object predicate, generating a patient adherence object score, the patient adherence object score indicating whether the adherence object was performed;
   generating a medical entity adherence score for the medical entity based on the patient adherence object scores, the medical entity adherence score indicating that medical entity's compliance with the adherence path; and
   generating a report indicating the medical entity adherence score.

2. The method of claim 1, wherein the medical entity is a medical professional, group of medical professionals, facility, or system.

3. The method of claim 1, further comprising generating, for each patient, a patient adherence path score based on a number of adherence objects that were performed relative to that particular patient in comparison to all adherence objects of the adherence path, wherein the medical entity adherence score for the medical entity is based on an average of the patient adherence path scores.

4. The method of claim 1, wherein the medical entity is a group of medical professionals and the method further comprises, for each medical professional of the group, generating, for each patient of that particular medical professional of the group, a patient adherence path score based on a number of adherence objects that were performed relative to that particular patient in comparison to all adherence objects of the adherence path, wherein the medical entity adherence score for the medical entity is based on an average of the patient adherence path scores.

5. The method of claim 1, wherein the medical entity is a group of medical professionals and the medical entity adherence score for the medical entity is based on the patient adherence object scores of patients of any of the group of medical professionals.

6. The method of claim 1, wherein the object predicate of a particular adherence object indicates two or more codes that are equivalents, wherein the object predicate of the particular adherence object may be satisfied by events corresponding to any of the two or more codes.

7. The method of claim 1, wherein the object predicate of a particular adherence object indicates two or more codes that must be completed to satisfy the object predicate, wherein the object predicate of the particular adherence object may be satisfied by all events corresponding to each of the two or more codes.

8. The method of claim 1, further comprising generating an interactive carepath interface enabling a user to view and add adherence objects to the adherence path or change the object predicate or time frame predicate to at least one adherence object of the adherence path.

9. The method of claim 1, further comprising, based on the patient adherence object scores, identifying a particular adherence object, and comparing outcomes of patients with treatments that did not comply with the particular adherence object with outcomes of patients with treatments that did comply with the particular adherence object.

10. The method of claim 9, further comprising removing the particular adherence object from the adherence path based on the comparison.

11. A non-transitory computer readable medium comprising executable instructions that are executable by a processor to perform a method, the method comprising:
    receiving a protocol associated with a particular medical condition, the protocol comprising a set of events to occur in treatment of the medical condition;
    selecting a subset of the events of the protocol to be adherence objects of an adherence path;
    determining a time frame predicate for each adherence object of the adherence path, the time frame predicate indicating a time frame during which an event related to the adherence object is to be performed;
    determining an object predicate for each adherence object of the adherence path, the object predicate indicating one or more codes of an electronic health record system associated with an event related to the adherence object, the electronic health record system storing medical information related to a medical entity, wherein a protocol specific adherence object is an adherence object of the adherence path of the protocol that was performed for treatment related to the protocol during the time frame indicated in the time frame predicate;

receiving a medical condition identifier indicating a medical condition, a treatment time frame identifier indicating a time frame during which treatment is to be performed, and a medical entity identifier identifying the medical entity;

retrieving patient information from medical records of patients of the medical entity, the patients having received treatment related to the medical condition during the treatment time frame, the patient information indicating events related to treatment, the events being at least a sub-subset of the subset of the events of the protocol;

for each patient, using that patient's patient information for each protocol specific adherence object that includes at least one code from the patient's patient information in the object predicate, generating a patient adherence object score, the patient adherence object score indicating whether the adherence object was performed;

generating a medical entity adherence score for the medical entity based on the patient adherence object scores, the medical entity adherence score indicating that medical entity's compliance with the adherence path; and generating a report indicating the medical entity adherence score.

12. The computer readable medium of claim 11, wherein the medical entity is a medical professional, group of medical professionals, facility, or system.

13. The computer readable medium of claim 11, the method further comprising generating, for each patient, a patient adherence path score based on a number of adherence objects that were performed relative to that particular patient in comparison to all adherence objects of the adherence path, wherein the medical entity adherence score for the medical entity is based on an average of the patient adherence path scores.

14. The computer readable medium of claim 11, wherein the medical entity is a group of medical professionals and the method further comprises, for each medical professional of the group, generating, for each patient of that particular medical professional of the group, a patient adherence path score based on a number of adherence objects that were performed relative to that particular patient in comparison to all adherence objects of the adherence path, wherein the medical entity adherence score for the medical entity is based on an average of the patient adherence path scores.

15. The computer readable medium of claim 11, wherein the medical entity is a group of medical professionals and the medical entity adherence score for the medical entity is based on the patient adherence object scores of patients of any of the group of medical professionals.

16. The computer readable medium of claim 11, wherein the object predicate of a particular adherence object indicates two or more codes that are equivalents, wherein the object predicate of the particular adherence object may be satisfied by events corresponding to any of the two or more codes.

17. The computer readable medium of claim 11, wherein the object predicate of a particular adherence object indicates two or more codes that must be completed to satisfy the object predicate, wherein the object predicate of the particular adherence object may be satisfied by all events corresponding to each of the two or more codes.

18. The computer readable medium of claim 11, the method further comprising generating an interactive care-path interface enabling a user to view and add adherence objects to the adherence path or change the object predicate or time frame predicate to at least one adherence object of the adherence path.

19. The computer readable medium of claim 11, the method further comprising, based on the patient adherence object scores, identifying a particular adherence object, and comparing outcomes of patients with treatments that did not comply with the particular adherence object with outcomes of patients with treatments that did comply with the particular adherence object.

20. The computer readable medium of claim 19, further comprising removing the particular adherence object from the adherence path based on the comparison.

21. A system comprising:
one or more processors; and
memory comprising instructions to configure the one or more processors to:
receive a protocol associated with a particular medical condition, the protocol comprising a set of events to occur in treatment of the medical condition;
select a subset of the events of the protocol to be adherence objects of an adherence path;
determine a time frame predicate for each adherence object of the adherence path, the time frame predicate indicating a time frame during which an event related to the adherence object is to be performed;
determine an object predicate for each adherence object of the adherence path, the object predicate indicating one or more codes of an electronic health record system associated with an event related to the adherence object, the electronic health record system storing medical information related to a medical entity, wherein a protocol specific adherence object is an adherence object of the adherence path of the protocol that was performed for treatment related to the protocol during the time frame indicated in the time frame predicate;
receive a medical condition identifier indicating a medical condition, a treatment time frame identifier indicating a time frame during which treatment is to be performed, and a medical entity identifier identifying the medical entity;
retrieve patient information from medical records of patients of the medical entity, the patients having received treatment related to the medical condition during the treatment time frame, the patient information indicating events related to treatment, the events being at least a sub-subset of the subset of the events of the protocol;
for each patient, use that patient's patient information;
for each protocol specific adherence object that includes at least one code from the patient's patient information in the object predicate, generate a patient adherence object score, the patient adherence object score indicating whether the adherence object was performed;
generate a medical entity adherence score for the medical entity based on the patient adherence object scores, the medical entity adherence score indicating that medical entity's compliance with the adherence path; and
generate a report indicating the medical entity adherence score.

* * * * *